United States Patent
Saltarelli et al.

(12)

(10) Patent No.: US 6,642,007 B1
(45) Date of Patent: *Nov. 4, 2003

(54) ASSAYS FOR MEASUREMENT OF TYPE II COLLAGEN FRAGMENTS IN URINE

(75) Inventors: Mary J. Saltarelli, Mystic, CT (US); Kimberly S. Johnson, Gales Ferry, CT (US); Ivan G. Otterness, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/504,262

(22) Filed: Feb. 15, 2000

Related U.S. Application Data

(63) Continuation-in-part of application No. 09/184,658, filed on Nov. 2, 1998, now Pat. No. 6,030,792.

(51) Int. Cl.$^7$ ............................................. G01N 33/53
(52) U.S. Cl. ..................... 435/7.1; 435/7.9; 435/7.91; 435/7.92; 435/7.93; 435/7.94; 435/7.95; 435/971; 436/524; 436/525; 436/526; 436/532; 436/538; 436/541; 530/356; 530/388.85; 530/391.1; 530/391.5; 530/391.9
(58) Field of Search ..................... 435/7.1, 7.9, 7.91, 435/7.92, 7.93, 7.94, 7.95, 971; 436/524, 525, 526, 532, 538, 541; 530/356, 388.85, 391.1, 391.5, 91.9

(56) References Cited

U.S. PATENT DOCUMENTS

| | | | | |
|---|---|---|---|---|
| 4,659,678 A | * | 4/1987 | Forrest et al. | 436/512 |
| 4,935,339 A | * | 6/1990 | Zahradnik | 435/5 |
| 5,320,970 A | | 6/1994 | Eyre | 436/536 |
| 5,532,169 A | * | 7/1996 | Eyre | 436/518 |
| 6,030,792 A | * | 2/2000 | Otterness et al. | 435/7.1 |
| 6,143,511 A | * | 11/2000 | Eyre | 435/7.94 |

FOREIGN PATENT DOCUMENTS

| | | | | |
|---|---|---|---|---|
| WO | WO 9414070 | 6/1994 | ......... | G01N/33/68 |
| WO | WO 9835235 | 8/1998 | ......... | G01N/33/577 |

OTHER PUBLICATIONS

Harris et al., *N. Engl. J. Med.*, 291:557–63, 605–09, 652–61 (1974).
Nagai et al., *Biochemistry*, 5:3123–3130 (1966).
Sakai et al., *Biochemistry*, 6:518–528 (1967).
Pendas et al., *Genomics*, 26:615–18 (1995).
Mitchell et al., *J. Clin. Invest.*, 97:761–68 (1996).
Maciewicz et al., *FEBS Lett.*, 269:189–93 (1990).
van Noorden et al., *Bioc. Biop. Res. Comm.*, 178:178–84 (1991).
Kivirikko, *Int. Rev. Connect. Tissue Res.*, 5:93–163 (1970).
Timpl, *Methods Enzymol.*, 82:472–98 (1982).
Holmdahl et al., *Immunology*, 61:369–74 (1987).
Punjabi et al., *J. Immunol.*, 141:3819–22 (1988).
Jasin et al., *J. Clin. Invest.*, 87:1531–36 (1991).
Norlund et al., *Trans. Orthoped. Res. Assoc.*, 22:313 (1997).
Dodge et al., *J. Clin. Invest.*, 83:647–61 (1989).
Dodge et al., *Matrix*, 11:330–38 (1991).
Hollander et al., *J. Clin. Invest.*, 93:1722–32 (1994).
Hollander et al., *J. Clin. Invest.*, 96:2859–69 (1995).
Billinghurst et al., *J. Clin. Invest.*, 99:1534–45 (1997).
Srinivas et al., *J. Immunol. Meth.*, 159:53–62 (1993).
Srinivas et al., *Agents Actions*, 41:193–99 (1994).
Srinivas et al., *Immunol. Invest.*, 23:85–98 (1994).
Chichester et al., *Pharm. Pharmacol.*, 48:694–98 (19.
Baydanoff et al., *Atherosclerosis*, 66:163–68 (1987).
Hamaoki et al., *Hybridoma*, 9:63–69 (1990).
Knudsen et al., *Eur. J. Pharmacol.*, 318:429–35 (1996).
Sato et al., *FEBS Lett*, 393, 101–104 (1996).
Otterness et al., *Matrix Biol*, 18:331–341 (1999).

* cited by examiner

Primary Examiner—Jeffrey Stucker
(74) *Attorney, Agent, or Firm*—Peter C. Richardson; Gregg C. Benson; Gregory P. Raymer

(57) ABSTRACT

This invention provides novel methods for monitoring urine for type II collagen fragment using a combination of a capture antibody and a detection antibody, such that type II collagen is distinguished from other collagen fragments.

35 Claims, 5 Drawing Sheets

Figure 1. Standard curve of peptide 130 (SEQ ID NO: 20) and resulting optical density reading determined 9A4 Capture/Bt-5109 Sandwich ELISA.
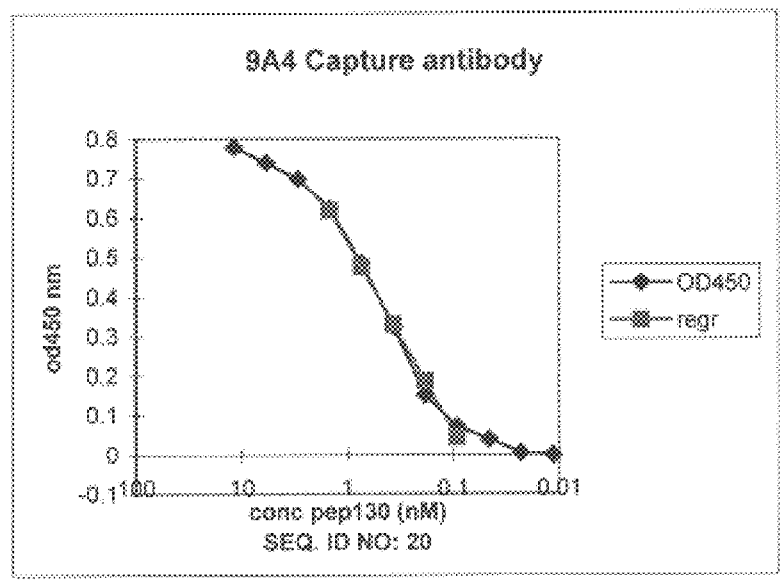
Figure 2. Standard curve for 5109 capture/Bt-9A4 detection sandwich assay.
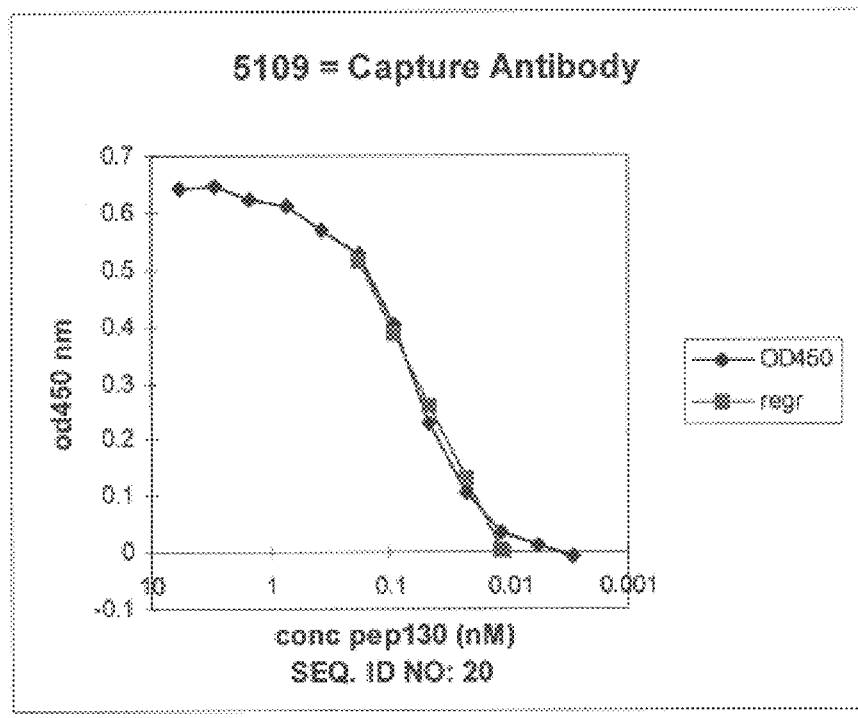

Collagen Fragments in Urine

- C4 extraction, C18 HPLC, capture 5109
- By size exclusion circa 6 kD

SEQUENCE LISTING

<160> NUMBER OF SEQ ID NOS: 70

<210> SEQ ID NO 1
<211> LENGTH: 7
<212> TYPE: PRT
<213> ORGANISM: Homo sapiens

<400> SEQUENCE: 1

Gly Pro Pro Gly Pro Gln Gly
1               5

<210> SEQ ID NO 2
<211> LENGTH: 7

```
<212> TYPE: PRT
<213> ORGANISM: Homo sapiens
<220> FEATURE:
<221> NAME/KEY: MOD_RES
<222> LOCATION: (1)..(7)
<223> OTHER INFORMATION: Type II Collagen Fragment with 4Hyp
<220> FEATURE:
<221> NAME/KEY: MISC_FEATURE
<222> LOCATION: (1)..(7)
<223> OTHER INFORMATION: Xaa is any amino acid.

<400> SEQUENCE: 2

Gly Pro Xaa Gly Pro Gln Gly
 1               5

<210> SEQ ID NO 3
<211> LENGTH: 10
<212> TYPE: PRT
<213> ORGANISM: Homo sapiens

<400> SEQUENCE: 3

Gly Glu Pro Gly Asp Asp Gly Pro Ser Gly
 1               5                  10

<210> SEQ ID NO 4
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Type II Collagen Fragment with 4Hyp
<220> FEATURE:
<221> NAME/KEY: MISC_FEATURE
<222> LOCATION: (1)..(10)
<223> OTHER INFORMATION: Xaa is any amino acid.

<400> SEQUENCE: 4

Gly Glu Xaa Gly Asp Asp Gly Pro Ser Gly
 1               5                  10

<210> SEQ ID NO 5
<211> LENGTH: 408
<212> TYPE: DNA
<213> ORGANISM: Mus musculus

<400> SEQUENCE: 5
ttcctgatgg cagctgccca aagtatccaa gcacagatcc agttggtgca gtctggtcct      60
gagctgaaga agcctggaga gacagtcaag atctcctgca aggcttctgg ttataccttc     120
acagactatt caatacactg ggtgaagcag gctccaggaa agggtttaaa gtggatgggc     180
tggataaaca ctgagactgg tgagccaaca tatgcagatg acttcaaggg acggtttgcc     240 ttctcttttgg aaacctctgc cagcactgcc tatttgcaga tcaacaacct caaaaatgag     300
gacacggcta catatttctg tgctaggggc ggtagccttg actactgggg ccaaggcacc     360
actctcacag tctcctcagc caaaacgaca ccccatctg tctatcca                   408

<210> SEQ ID NO 6
<211> LENGTH: 359
<212> TYPE: DNA
<213> ORGANISM: Mus musculus

<400> SEQUENCE: 6
cctcagtcat actgtccaga ggacaaattg ttctcaccca gtctccagta ttcatgtctg      60
catctccagg ggagaaggtc accatgacct gcagtgccag ctcaagtgta agttacatgt     120
```

```
actggtacca gcagaagcca ggatcctccc ccagactcct gattcatgcc acatccaacc      180
tggcttctgg agtccctgtt cgcttcagtg gcggtgggtc tgggacctct tactctctca      240
caatcagccg aatggaggct gaagatgctg ccacttatta ctgtcagcag tggagaagtt      300
atacacggac gttcggtgga ggcaccaagc tggaaatcat acgggctgat gctgcacca      359
```

<210> SEQ ID NO 7
<211> LENGTH: 883
<212> TYPE: DNA
<213> ORGANISM: Artificial Sequence
<220> FEATURE:
<223> OTHER INFORMATION: 9A4 scFv from clone p9A4ICAT7-1

<400> SEQUENCE: 7

```
aagctttgga gccttggaga ttttcaacgt gaaaaaatta ttattcgcaa ttcctttagt       60
tgttcctttt tatgcggccc agccggccat ggcccagatc cagttggtgc agtctggtcc      120
tgagctgaag aagcctggag agacagtcaa gatcctgc aaggcttctg gttataccett       180 cacagactat tcaatacact gggtgaagca ggctccagga aagggtttaa agtggatggg      240
ctggataaac actgagactg gtgagccaac atatgcagat gacttcaagg gacggtttgc      300
cttctctttg gaaacctctg ccagcactgc ctatttgcag atcaacaacc tcaaaaatga      360
ggacacggct acatatttct gtgctagggg cggtagcctt gactactggg gccaaggcac      420
cactctcaca gtctcctcag gtggaggcgg ttcaggcgga ggtggcagcg gcggtggcgg      480
atcgcaaatt gttctcaccc agtctccagt attcatgtct gcatctccag gggagaaggt      540
caccatgacc tgcagtgcca gctcaagtgt aagttacatg tactggtacc agcagaagcc      600
aggatcctcc cccagactcc tgattcatgc acatccaaac ctggcttctg gagtccctgt      660
tcgcttcagt ggcggtgggt ctgggacctc ttactctctc acaatcagcc gaatggaggc      720
tgaagatgct gccacttatt actgtcagca gtggagaagt tatacacgga cgttcggtgg      780
aggcaccaag ctggaaatca tagcggccgc acatcatcat caccatcacg ggccgcaga      840 acaaaaactc atctcagaag aggatctgaa tggggccgca tag                        883
```

<210> SEQ ID NO 8
<211> LENGTH: 1340
<212> TYPE: DNA
<213> ORGANISM: Artificial Sequence
<220> FEATURE:
<223> OTHER INFORMATION: 9A4 scFv from clone p9A4IF-5

<400> SEQUENCE: 8

```
ctcatgtttg acagcttatc atcgatgaat tccatcactt ccctccgttc atttgtcccc       60
ggtggaaacg aggtcatcat ttccttccga aaaacggtt gcatttaaat cttacatata       120
taatactttc aaagactaca tttgtaagat ttgatgtttg agtcggctga agatcgtac       180 gtaccaatta ttgtttcgtg attgttcaag ccataacact gtagggatag tggaaagagt      240
gcttcatctg gttacgatca atcaaatatt caaacgagg gagacgattt tgatgaaata      300
cctattgcct acggcagccg ctggattgtt attactcgct gcccaaccag ccatggccca      360
aattgttctc acccagtctc cagtattcat gtctgcatct ccaggggaga aggtcaccat      420
gacctgcagt gccagctcaa gtgtaagtta catgtactgg taccagcaga agccaggatc      480
ctcccccaga ctcctgattc atgccacatc aacctggct ctggagtcc ctgttcgctt       540 cagtggcggt gggtctggga cctcttactc tctcacaatc agccgaatgg aggctgaaga      600
```

-continued

```
tgctgccact tattactgtc agcagtggag aagttataca cggacgttcg gtggaggcac      660
caagctggaa atcatactta gtgcggacga tgcgaaaaag gatgctgcga agaaggatga      720
cgctaagaaa gacgatgcta aaaaggacct cgagatccag ttggtgcagt ctggtcctga      780
gctgaagaag cctggagaga cagtcaagat ctcctgcaag gcttctggtt ataccttcac      840
agactattca atacactggg tgaagcaggc tccaggaaag ggtttaaagt ggatgggctg      900
gataaacact gagactggtg agccaacata tgcagatgac ttcaagggac ggtttgcctt      960
ctctttggaa acctctgcca gcactgccta tttgcagatc aacaacctca aaatgagga     1020 cacggctaca tatttctgtg ctaggggcgg tagccttgac tactggggcc aaggcaccac     1080
tctcacagtc tcctcagcta gcgactacaa ggacgatgat gacaaataaa acctagcga     1140 tgaatccgtc aaaacatcat cttacataaa gtcacttggt gatcaagctc atatcattgt     1200
ccggcaatgg tgtgggcttt ttttgttttc tatctttaaa gatcatgtga agaaaaacgg     1260
gaaaatcggt ctgcgggaaa ggaccgggtt tttgtcgaaa tcataggcga atgggttgga     1320
ttgtgacaaa attcggatcc                                                 1340
```

<210> SEQ ID NO 9
<211> LENGTH: 907
<212> TYPE: DNA
<213> ORGANISM: Artificial Sequence
<220> FEATURE:
<223> OTHER INFORMATION: 5109 scFv from clone p5109scFv7

<400> SEQUENCE: 9

```
aagctttgga gccttggaga ttttcaacgt gaaaaaatta ttattcgcaa ttcctttagt       60
tgttcctttt tatgcggccc agccggccat ggccgaagtg cagctggtgg agtctggggg      120
aggctcagtg cagcctggag ggtccctgaa actctcctgt gcagcctctg gattcacttt      180 caataccctac ggcatgtctt gggttcgcca gactccagac aagaggctgg agtgggtcgc      240
aaccattaat agtaatggtg gtctcacctt ttatgcagac agtgtgaagg gccgattcac      300
catttccaga gacaatgcca aaaacaccct gtatctgcaa atgaacaggc tgaagtctgg      360
ggactcaggc atgtattact gtgtaagagg atatagtaat tacgctcgct ggggccaagg      420
ggcgctggtc actgtctcga gtggtggagg cggttcaggc ggaggtggca gcggcggtgg      480
cggatcgtct gatgttgtga tgacccaaac tccactcact ttgtcggtta ccattggaca      540
atcagcctcc atctcttgca agtcaagtca gagcctctta ggtagtgatg gattgacata      600
tttgatttgg ttgttgcaga ggccaggcca gtctccaaag cgcctaatct ttctggtgtc      660
tgaattggac tctggagtcc ctgacaggtt cactggcagt ggatcaggga cagatttcac      720
actgaaaatc agcagagcgg aggctgaaga tttgggagtt tattattgct gccaaggtac      780 acatttttcct cacacgttcg gtgctgggac caagctggag ctgaaagcgg ccgcagaact      840
aaaactcatc tcagaagagg atctgaatgg ggccgcacat caccaccatc accattaata      900
agaattc                                                                907
```

<210> SEQ ID NO 10
<211> LENGTH: 348
<212> TYPE: DNA
<213> ORGANISM: Mus musculus

<400> SEQUENCE: 10

```
gaagtgcagc tggtggagtc tgggggaggc tcagtgcagc ctggagggtc cctgaaactc       60
tcctgtgcag cctctggatt cactttcaat acctacggca tgtcttgggt tcgccagact      120
```

```
ccagacaaga ggctggagtg ggtcgcaacc attaatagta atggtggtct caccttttat    180
gcagacagtg tgaagggccg attcaccatt tccagagaca atgccaaaaa caccctgtat    240
ctgcaaatga acaggctgaa gtctggggac tcaggcatgt attactgtgt aagaggatat    300
agtaattacg ctcgctgggg ccaagggcg ctggtcactg tctctgca                  348
```

<210> SEQ ID NO 11
<211> LENGTH: 336
<212> TYPE: DNA
<213> ORGANISM: Mus musculus

<400> SEQUENCE: 11

```
gatgttgtga tgacccaaac tccactcact ttgtcggtta ccattggaca atcagcctcc     60
atctcttgca agtcaagtca gagcctctta ggtagtgatg gattgacata tttgatttgg    120
ttgttgcaga ggccaggcca gtctccaaag cgcctaatct ttctggtgtc tgaattggac    180
tctggagtcc ctgacaggtt cactggcagt ggatcaggga cagatttcac actgaaaatc    240
agcagagtgg aggctgaaga tttgggagtt tattattgct gccaaggtac acattttcct    300
cacacgttcg gtgctgggac caagctggag ctgaaa                              336
```

<210> SEQ ID NO 12
<211> LENGTH: 13
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Type II Collagen Fragment with 4Hyp
<220> FEATURE:
<221> NAME/KEY: MISC_FEATURE
<222> LOCATION: (1)..(13)
<223> OTHER INFORMATION: Xaa is any amino acid.
<220> FEATURE:
<221> NAME/KEY: MOD_RES
<222> LOCATION: (1)..(11)
<223> OTHER INFORMATION: Type II Collagen Fragment with 4Hyp.
<220> FEATURE:
<221> NAME/KEY: MOD_RES
<222> LOCATION: (1)..(8)
<223> OTHER INFORMATION: Type II Collagen Fragment with 4Jyp.

<400> SEQUENCE: 12

```
Ala Xaa Gly Glu Asp Gly Arg Xaa Gly Pro Xaa Gly Pro
1               5                   10
```

<210> SEQ ID NO 13
<211> LENGTH: 20
<212> TYPE: PRT
<213> ORGANISM: Homo sapiens
<220> FEATURE:
<221> NAME/KEY: MOD_RES
<222> LOCATION: (1)..(9)
<223> OTHER INFORMATION: Type II Collagen Fragment with 4Hyp.
<220> FEATURE:
<221> NAME/KEY: MISC_FEATURE
<222> LOCATION: (1)..(20)
<223> OTHER INFORMATION: Xaa is any amino acid.
<220> FEATURE:
<221> NAME/KEY: MOD_RES
<222> LOCATION: (1)..(15)
<223> OTHER INFORMATION: Type II Collagen Fragment with 4Hyp.
<220> FEATURE:
<221> NAME/KEY: MOD_RES
<222> LOCATION: (1)..(18)
<223> OTHER INFORMATION: Type II Collagen Fragment with 4Hyp.

<400> SEQUENCE: 13

-continued

Gly Lys Val Gly Pro Ser Gly Ala Xaa Gly Glu Asp Gly Arg Xaa Gly
1               5                   10                  15

Pro Xaa Gly Pro
            20

<210> SEQ ID NO 14
<211> LENGTH: 9
<212> TYPE: PRT
<213> ORGANISM: Homo sapiens
<220> FEATURE:
<221> NAME/KEY: DOMAIN
<222> LOCATION: (1)..(9)
<223> OTHER INFORMATION: Type II collagen fragment.

<400> SEQUENCE: 14

Ala Glu Gly Pro Pro Gly Pro Gln Gly
1               5

<210> SEQ ID NO 15
<211> LENGTH: 10
<212> TYPE: PRT
<213> ORGANISM: Homo sapiens
<220> FEATURE:
<221> NAME/KEY: MOD_RES
<222> LOCATION: (1)..(3)
<223> OTHER INFORMATION: Type II collagen fragment with 4Hyp.
<220> FEATURE:
<221> NAME/KEY: MISC_FEATURE
<222> LOCATION: (1)..(10)
<223> OTHER INFORMATION: Xaa is any amino acid.
<220> FEATURE:
<221> NAME/KEY: SITE
<222> LOCATION: (1)..(7)
<223> OTHER INFORMATION: Collagenase cleaves on the - COOH side of
      residue.

<400> SEQUENCE: 15

Gly Pro Xaa Gly Pro Gln Gly Leu Ala Gly
1               5                   10

<210> SEQ ID NO 16
<211> LENGTH: 7
<212> TYPE: PRT
<213> ORGANISM: Homo sapiens
<220> FEATURE:
<221> NAME/KEY: DOMAIN
<222> LOCATION: (1)..(7)
<223> OTHER INFORMATION: Type I collagen fragment.

<400> SEQUENCE: 16

Gly Thr Pro Gly Pro Gln Gly
1               5

<210> SEQ ID NO 17
<211> LENGTH: 10
<212> TYPE: PRT
<213> ORGANISM: Artificial Sequence
<220> FEATURE:
<223> OTHER INFORMATION: antigenic fragment for immunization

<400> SEQUENCE: 17

Cys Ala Glu Gly Pro Pro Gly Pro Gln Gly
1               5                   10

<210> SEQ ID NO 18
<211> LENGTH: 10
<212> TYPE: PRT
<213> ORGANISM: Artificial Sequence -continued

```
<220> FEATURE:
<223> OTHER INFORMATION: antigenic fragment for immunization

<400> SEQUENCE: 18

Cys Gly Glu Pro Gly Asp Asp Gly Pro Ser
1               5                   10

<210> SEQ ID NO 19
<211> LENGTH: 9
<212> TYPE: PRT
<213> ORGANISM: Homo sapiens
<220> FEATURE:
<221> NAME/KEY: DOMAIN
<222> LOCATION: (1)..(9)
<223> OTHER INFORMATION: Type II collagen fragment.

<400> SEQUENCE: 19

Gly Glu Pro Gly Asp Asp Gly Pro Ser
1               5

<210> SEQ ID NO 20
<211> LENGTH: 19
<212> TYPE: PRT
<213> ORGANISM: Homo sapiens
<220> FEATURE:
<221> NAME/KEY: DOMAIN
<222> LOCATION: (1)..(19)
<223> OTHER INFORMATION: Type II collagen fragment.

<400> SEQUENCE: 20

Gly Glu Pro Gly Asp Asp Gly Pro Ser Gly Ala Glu Gly Pro Pro Gly
1               5                   10                  15

Pro Gln Gly

<210> SEQ ID NO 21
<211> LENGTH: 20
<212> TYPE: DNA
<213> ORGANISM: Mus musculus

<400> SEQUENCE: 21
ggtgaagttg atgtcttgtg                                          20

<210> SEQ ID NO 22
<211> LENGTH: 23
<212> TYPE: DNA
<213> ORGANISM: Mus musculus

<400> SEQUENCE: 22
gaccttgcat ttgaactcct tgc                                      23

<210> SEQ ID NO 23
<211> LENGTH: 20
<212> TYPE: DNA
<213> ORGANISM: Mus musculus

<400> SEQUENCE: 23
ggctgtggaa cttgctattc                                          20

<210> SEQ ID NO 24
<211> LENGTH: 20
<212> TYPE: DNA
<213> ORGANISM: Mus musculus

<400> SEQUENCE: 24
gggtgtggac cttgccattc                                          20
```

<210> SEQ ID NO 25
<211> LENGTH: 20
<212> TYPE: DNA
<213> ORGANISM: Mus musculus

<400> SEQUENCE: 25
gggtgtggac cttgctattc                                            20

<210> SEQ ID NO 26
<211> LENGTH: 20
<212> TYPE: DNA
<213> ORGANISM: Artificial Sequence
<220> FEATURE:
<223> OTHER INFORMATION: primer for cloning
<220> FEATURE:
<221> NAME/KEY: misc_feature
<223> OTHER INFORMATION: Description of Artificial Sequence:  Mixed
      oligonucleotide set a s PCR primers for murine VH signal peptide
      region.

<400> SEQUENCE: 26
ggstgtggam cttgcyattc                                            20

<210> SEQ ID NO 27
<211> LENGTH: 18
<212> TYPE: DNA
<213> ORGANISM: Artificial Sequence
<220> FEATURE:
<223> OTHER INFORMATION: primer for cloning
<220> FEATURE:
<221> NAME/KEY: misc_feature
<223> OTHER INFORMATION: Description of Artificial Sequence:  Mixed
      oligonucleotideset as PCR primers for murine VL signal peptide
      region.

<400> SEQUENCE: 27
gcttcctgct aatcaktg                                              18

<210> SEQ ID NO 28
<211> LENGTH: 21
<212> TYPE: DNA
<213> ORGANISM: Mus musculus

<400> SEQUENCE: 28
ggcagcagat ccaggggcca g                                          21

<210> SEQ ID NO 29
<211> LENGTH: 33
<212> TYPE: DNA
<213> ORGANISM: Artificial Sequence
<220> FEATURE:
<223> OTHER INFORMATION: primer for cloning
<220> FEATURE:
<221> NAME/KEY: misc_feature
<223> OTHER INFORMATION: Description of Artificial Sequence:  Murine
      light chain Kappa region primer with Hind III site.

<400> SEQUENCE: 29
gggaaagctt gttaactgct cactggatgg tgg                             33

<210> SEQ ID NO 30
<211> LENGTH: 22
<212> TYPE: DNA
<213> ORGANISM: Erwinia carotovora

<400> SEQUENCE: 30

```
ctattgccta cggcagccgc tg                                              22
```

<210> SEQ ID NO 31
<211> LENGTH: 20
<212> TYPE: DNA
<213> ORGANISM: Bacillus licheniformis

<400> SEQUENCE: 31

```
cacatgatct ttaaagatag                                                 20
```

<210> SEQ ID NO 32
<211> LENGTH: 136
<212> TYPE: PRT
<213> ORGANISM: Mus musculus
<220> FEATURE:
<221> NAME/KEY: SIGNAL
<222> LOCATION: (1)..(11)
<223> OTHER INFORMATION: Portion of 9A4 VH signal peptide.
<220> FEATURE:
<221> NAME/KEY: DOMAIN
<222> LOCATION: (12)..(126)
<223> OTHER INFORMATION: Mature 9A4 VH.
<220> FEATURE:
<221> NAME/KEY: DOMAIN
<222> LOCATION: (127)..(136)
<223> OTHER INFORMATION: Portion of murine IgG1 CH1 constant domain.

<400> SEQUENCE: 32

```
Phe Leu Met Ala Ala Ala Gln Ser Ile Gln Ala Gln Ile Gln Leu Val
1               5                   10                  15

Gln Ser Gly Pro Glu Leu Lys Lys Pro Gly Glu Thr Val Lys Ile Ser
            20                  25                  30

Cys Lys Ala Ser Gly Tyr Thr Phe Thr Asp Tyr Ser Ile His Trp Val
        35                  40                  45

Lys Gln Ala Pro Gly Lys Gly Leu Lys Trp Met Gly Trp Ile Asn Thr
    50                  55                  60

Glu Thr Gly Glu Pro Thr Tyr Ala Asp Asp Phe Lys Gly Arg Phe Ala
65                  70                  75                  80

Phe Ser Leu Glu Thr Ser Ala Ser Thr Ala Tyr Leu Gln Ile Asn Asn
                85                  90                  95

Leu Lys Asn Glu Asp Thr Ala Thr Tyr Phe Cys Ala Arg Gly Gly Ser
            100                 105                 110

Leu Asp Tyr Trp Gly Gln Gly Thr Thr Leu Thr Val Ser Ser Ala Lys
        115                 120                 125

Thr Thr Pro Pro Ser Val Tyr Pro
    130                 135
```

<210> SEQ ID NO 33
<211> LENGTH: 119
<212> TYPE: PRT
<213> ORGANISM: Mus musculus
<220> FEATURE:
<221> NAME/KEY: SIGNAL
<222> LOCATION: (1)..(7)
<223> OTHER INFORMATION: Portion of 9A4 VL signal peptide.
<220> FEATURE:
<221> NAME/KEY: DOMAIN
<222> LOCATION: (8)..(113)
<223> OTHER INFORMATION: Mature 9A4 VL.
<220> FEATURE:
<221> NAME/KEY: DOMAIN
<222> LOCATION: (114)..(119)
<223> OTHER INFORMATION: Portion of murine C kappa constant domain.

<400> SEQUENCE: 33

```
Ser Val Ile Leu Ser Arg Gly Gln Ile Val Leu Thr Gln Ser Pro Val
1               5                   10                  15

Phe Met Ser Ala Ser Pro Gly Glu Lys Val Thr Met Thr Cys Ser Ala
            20                  25                  30

Ser Ser Ser Val Ser Tyr Met Tyr Trp Tyr Gln Gln Lys Pro Gly Ser
        35                  40                  45

Ser Pro Arg Leu Leu Ile His Ala Thr Ser Asn Leu Ala Ser Gly Val
    50                  55                  60

Pro Val Arg Phe Ser Gly Gly Ser Gly Thr Ser Tyr Ser Leu Thr
65                  70                  75                  80

Ile Ser Arg Met Glu Ala Glu Asp Ala Ala Thr Tyr Tyr Cys Gln Gln
                85                  90                  95

Trp Arg Ser Tyr Thr Arg Thr Phe Gly Gly Gly Thr Lys Leu Glu Ile
                100                 105                 110

Ile Arg Ala Asp Ala Ala Pro
            115
```

<210> SEQ ID NO 34
<211> LENGTH: 47
<212> TYPE: DNA
<213> ORGANISM: Artificial Sequence
<220> FEATURE:
<223> OTHER INFORMATION: primer for cloning
<220> FEATURE:
<221> NAME/KEY: misc_feature
<223> OTHER INFORMATION: Description of Artificial Sequence: PCR - SOE primer for 5' 9A4 VH region, including an Sfi I restriction endonuclease site.

<400> SEQUENCE: 34
gaggaggccc agccggccat ggcccagatc cagttggtgc agtctgg         47

<210> SEQ ID NO 35
<211> LENGTH: 61
<212> TYPE: DNA
<213> ORGANISM: Artificial Sequence
<220> FEATURE:
<223> OTHER INFORMATION: primer for cloning
<220> FEATURE:
<221> NAME/KEY: misc_feature
<223> OTHER INFORMATION: Description of Artificial Sequence: PCR - SOE primer for 3' 9A4 VH region, including linker segment of scFv for assembly PCR reaction with 9A4 VL.

<400> SEQUENCE: 35
gccgctgcca cctccgcctg aaccgcctcc accactcgag actgtgagag tggtgccttg     60
g                                                                    61

<210> SEQ ID NO 36
<211> LENGTH: 56
<212> TYPE: DNA
<213> ORGANISM: Artificial Sequence
<220> FEATURE:
<223> OTHER INFORMATION: primer for cloning

<400> SEQUENCE: 36
ggttcaggcg gaggtggcag cggcggtggc ggatcgcaaa ttgttctcac ccagtc         56

<210> SEQ ID NO 37
<211> LENGTH: 38
<212> TYPE: DNA
<213> ORGANISM: Artificial Sequence
<220> FEATURE:
<223> OTHER INFORMATION: primer for cloning

```
<220> FEATURE:
<221> NAME/KEY: misc_feature
<223> OTHER INFORMATION: Description of Artificial Sequence:  PCR - SOE
      primer for 3' 9A4 VL region, including a Not I restriction
      endonuclease site.

<400> SEQUENCE: 37
gaaggacgcc ggcgtatgat ttccagcttg gtgcctcc                             38

<210> SEQ ID NO 38
<211> LENGTH: 36
<212> TYPE: DNA
<213> ORGANISM: Artificial Sequence
<220> FEATURE:
<223> OTHER INFORMATION: primer for cloning
<220> FEATURE:
<221> NAME/KEY: misc_feature
<223> OTHER INFORMATION: Description of Artificial Sequence:  9A4 scFv
      PCR primer, including a Not 1 restriction endonuclease site.

<400> SEQUENCE: 38
aagaagcggc cgctatgatt tccagcttgg tgcctc                               36

<210> SEQ ID NO 39
<211> LENGTH: 23
<212> TYPE: DNA
<213> ORGANISM: Escherichia coli

<400> SEQUENCE: 39
agcggataac aatttcacac agg                                             23

<210> SEQ ID NO 40
<211> LENGTH: 284
<212> TYPE: PRT
<213> ORGANISM: Artificial Sequence
<220> FEATURE:
<223> OTHER INFORMATION: 9A4 scFv from clone p9A4ICAT7-1
<220> FEATURE:
<221> NAME/KEY: misc_feature
<223> OTHER INFORMATION: Description of Artificial Sequence:  9A4 scFv
      VH - VL.
<220> FEATURE:
<221> NAME/KEY: SIGNAL
<222> LOCATION: (1)..(22)
<223> OTHER INFORMATION: pCANTAB6 signal peptide; Val at position 1 is
      most likely the initiator Met.
<220> FEATURE:
<221> NAME/KEY: DOMAIN
<222> LOCATION: (23)..(137)
<223> OTHER INFORMATION: 9A4 VH domain.
<220> FEATURE:
<221> NAME/KEY: DOMAIN
<222> LOCATION: (138)..(152)
<223> OTHER INFORMATION: 15 amino acid linker.
<220> FEATURE:
<221> NAME/KEY: DOMAIN
<222> LOCATION: (153)..(258)
<223> OTHER INFORMATION: 9A4 VL domain.
<220> FEATURE:
<221> NAME/KEY: SITE
<222> LOCATION: (262)..(267)
<223> OTHER INFORMATION: His tag.
<220> FEATURE:
<221> NAME/KEY: SITE
<222> LOCATION: (271)..(280)
<223> OTHER INFORMATION: myc tag.

<400> SEQUENCE: 40

Met Lys Lys Leu Leu Phe Ala Ile Pro Leu Val Val Pro Phe Tyr Ala
1               5                   10                  15

Ala Gln Pro Ala Met Ala Gln Ile Gln Leu Val Gln Ser Gly Pro Glu
```

```
                20                  25                  30
Leu Lys Lys Pro Gly Glu Thr Val Lys Ile Ser Cys Lys Ala Ser Gly
            35                  40                  45

Tyr Thr Phe Thr Asp Tyr Ser Ile His Trp Val Lys Gln Ala Pro Gly
 50                  55                  60

Lys Gly Leu Lys Trp Met Gly Trp Ile Asn Thr Glu Thr Gly Glu Pro
 65                  70                  75                  80

Thr Tyr Ala Asp Asp Phe Lys Gly Arg Phe Ala Phe Ser Leu Glu Thr
                85                  90                  95

Ser Ala Ser Thr Ala Tyr Leu Gln Ile Asn Asn Leu Lys Asn Glu Asp
            100                 105                 110

Thr Ala Thr Tyr Phe Cys Ala Arg Gly Gly Ser Leu Asp Tyr Trp Gly
            115                 120                 125

Gln Gly Thr Thr Leu Thr Val Ser Ser Gly Gly Gly Ser Gly Gly
        130                 135                 140

Gly Gly Ser Gly Gly Gly Ser Gln Ile Val Leu Thr Gln Ser Pro
145                 150                 155                 160

Val Phe Met Ser Ala Ser Pro Gly Glu Lys Val Thr Met Thr Cys Ser
                165                 170                 175

Ala Ser Ser Ser Val Ser Tyr Met Tyr Trp Tyr Gln Gln Lys Pro Gly
            180                 185                 190

Ser Ser Pro Arg Leu Leu Ile His Ala Thr Ser Asn Leu Ala Ser Gly
            195                 200                 205

Val Pro Val Arg Phe Ser Gly Gly Ser Gly Thr Ser Tyr Ser Leu
    210                 215                 220

Thr Ile Ser Arg Met Glu Ala Glu Asp Ala Ala Thr Tyr Tyr Cys Gln
225                 230                 235                 240

Gln Trp Arg Ser Tyr Thr Arg Thr Phe Gly Gly Gly Thr Lys Leu Glu
                245                 250                 255

Ile Ile Ala Ala Ala His His His His His His Gly Ala Ala Glu Gln
                260                 265                 270

Lys Leu Ile Ser Glu Glu Asp Leu Asn Gly Ala Ala
            275                 280

<210> SEQ ID NO 41
<211> LENGTH: 21
<212> TYPE: DNA
<213> ORGANISM: Bacteriophage fd

<400> SEQUENCE: 41
gtcgtctttc cagacgttag t                                          21

<210> SEQ ID NO 42
<211> LENGTH: 25
<212> TYPE: PRT
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence: Single
      chain antibody linker sequence.

<400> SEQUENCE: 42

Leu Ser Ala Asp Asp Ala Lys Lys Asp Ala Ala Lys Lys Asp Asp Ala
1               5                   10                  15

Lys Lys Asp Asp Ala Lys Lys Asp Leu
            20                  25
```

<210> SEQ ID NO 43
<211> LENGTH: 34
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence: PCR - SOE primer for 5' 9A4 VL region, including an Nco I restriction endonuclease site.

<400> SEQUENCE: 43
gaggagccat ggcccaaatt gttctcaccc agtc        34

<210> SEQ ID NO 44
<211> LENGTH: 79
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence: PCR - SOE primer for 3' 9A4 VL region, including linker segment of scFv for assembly PCR reaction with 9A4 VH.

<400> SEQUENCE: 44
ctttcttagc gtcatccttc ttcgcagcat cctttttcgc atcgtccgca ctaagcttga        60
tttccagctt ggtgcctcc        79

<210> SEQ ID NO 45
<211> LENGTH: 70
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence: PCR - SOE primer for 5' 9A4 VH region, including linker segment of scFv for assembly PCR reaction with 9A4 VL.

<400> SEQUENCE: 45
ctgcgaagaa ggatgacgct aagaaagacg atgctaaaaa ggacctcgag atccagttgg        60
tgcagtctgg        70

<210> SEQ ID NO 46
<211> LENGTH: 36
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence: PCR - SOE primer for 3' 9A4 VH region, including an Nhe 1 restriction endonuclease site.

<400> SEQUENCE: 46
gaggaagcta gctgaggaga ctgtgagagt ggtgcc        36

<210> SEQ ID NO 47
<211> LENGTH: 278
<212> TYPE: PRT
<213> ORGANISM: Artificial Sequence
<220> FEATURE:

```
<223> OTHER INFORMATION: 9A4 scFv from clone p9A4IF-5
<220> FEATURE:
<221> NAME/KEY: misc_feature
<223> OTHER INFORMATION: Description of Artificial Sequence:   9A4 scFv
      VL - VH.
<220> FEATURE:
<221> NAME/KEY: SIGNAL
<222> LOCATION: (1)..(22)
<223> OTHER INFORMATION: pel B signal peptide in pATDFLAG.
<220> FEATURE:
<221> NAME/KEY: DOMAIN
<222> LOCATION: (23)..(128)
<223> OTHER INFORMATION: 9A4 VL domain.
<220> FEATURE:
<221> NAME/KEY: DOMAIN
<222> LOCATION: (129)..(153)
<223> OTHER INFORMATION: 25 amino acid linker.
<220> FEATURE:
<221> NAME/KEY: DOMAIN
<222> LOCATION: (154)..(268)
<223> OTHER INFORMATION: 9A4 VH domain.
<220> FEATURE:
<221> NAME/KEY: SITE
<222> LOCATION: (271)..(278)
<223> OTHER INFORMATION: FLAG tag.

<400> SEQUENCE: 47
```

Met Lys Tyr Leu Leu Pro Thr Ala Ala Ala Gly Leu Leu Leu Leu Ala
1               5                   10                  15

Ala Gln Pro Ala Met Ala Gln Ile Val Leu Thr Gln Ser Pro Val Phe
            20                  25                  30

Met Ser Ala Ser Pro Gly Glu Lys Val Thr Met Thr Cys Ser Ala Ser
        35                  40                  45

Ser Ser Val Ser Tyr Met Tyr Trp Tyr Gln Gln Lys Pro Gly Ser Ser
    50                  55                  60

Pro Arg Leu Leu Ile His Ala Thr Ser Asn Leu Ala Ser Gly Val Pro
65                  70                  75                  80

Val Arg Phe Ser Gly Gly Gly Ser Gly Thr Ser Tyr Ser Leu Thr Ile
                85                  90                  95

Ser Arg Met Glu Ala Glu Asp Ala Ala Thr Tyr Tyr Cys Gln Gln Trp
            100                 105                 110

Arg Ser Tyr Thr Arg Thr Phe Gly Gly Gly Thr Lys Leu Glu Ile Ile
        115                 120                 125

Leu Ser Ala Asp Asp Ala Lys Lys Asp Ala Ala Lys Lys Asp Asp Ala
    130                 135                 140

Lys Lys Asp Asp Ala Lys Lys Asp Leu Glu Ile Gln Leu Val Gln Ser
145                 150                 155                 160

Gly Pro Glu Leu Lys Lys Pro Gly Glu Thr Val Lys Ile Ser Cys Lys
                165                 170                 175

Ala Ser Gly Tyr Thr Phe Thr Asp Tyr Ser Ile His Trp Val Lys Gln
            180                 185                 190

Ala Pro Gly Lys Gly Leu Lys Trp Met Gly Trp Ile Asn Thr Glu Thr
        195                 200                 205

Gly Glu Pro Thr Tyr Ala Asp Asp Phe Lys Gly Arg Phe Ala Phe Ser
    210                 215                 220

Leu Glu Thr Ser Ala Ser Thr Ala Tyr Leu Gln Ile Asn Asn Leu Lys
225                 230                 235                 240

Asn Glu Asp Thr Ala Thr Tyr Phe Cys Ala Arg Gly Gly Ser Leu Asp
                245                 250                 255

Tyr Trp Gly Gln Gly Thr Thr Leu Thr Val Ser Ser Ala Ser Asp Tyr
            260                 265                 270

```
Lys Asp Asp Asp Asp Lys
        275

<210> SEQ ID NO 48
<211> LENGTH: 116
<212> TYPE: PRT
<213> ORGANISM: Mus musculus
<220> FEATURE:
<221> NAME/KEY: DOMAIN
<222> LOCATION: (1)..(116)
<223> OTHER INFORMATION: Mature 5109 VH.

<400> SEQUENCE: 48

Glu Val Gln Leu Val Glu Ser Gly Gly Gly Ser Val Gln Pro Gly Gly
1               5                   10                  15

Ser Leu Lys Leu Ser Cys Ala Ala Ser Gly Phe Thr Phe Asn Thr Tyr
            20                  25                  30

Gly Met Ser Trp Val Arg Gln Thr Pro Asp Lys Arg Leu Glu Trp Val
        35                  40                  45

Ala Thr Ile Asn Ser Asn Gly Gly Leu Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Arg Leu Lys Ser Gly Asp Ser Gly Met Tyr Tyr Cys
                85                  90                  95

Val Arg Gly Tyr Ser Asn Tyr Ala Arg Trp Gly Gln Gly Ala Leu Val
            100                 105                 110

Thr Val Ser Ala
        115

<210> SEQ ID NO 49
<211> LENGTH: 112
<212> TYPE: PRT
<213> ORGANISM: Mus musculus
<220> FEATURE:
<221> NAME/KEY: DOMAIN
<222> LOCATION: (1)..(112)
<223> OTHER INFORMATION: Mature 5109 VL.

<400> SEQUENCE: 49

Asp Val Val Met Thr Gln Thr Pro Leu Thr Leu Ser Val Thr Ile Gly
1               5                   10                  15

Gln Ser Ala Ser Ile Ser Cys Lys Ser Ser Gln Ser Leu Leu Gly Ser
            20                  25                  30

Asp Gly Leu Thr Tyr Leu Ile Trp Leu Leu Gln Arg Pro Gly Gln Ser
        35                  40                  45

Pro Lys Arg Leu Ile Phe Leu Val Ser Glu Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Cys Gln Gly
                85                  90                  95

Thr His Phe Pro His Thr Phe Gly Ala Gly Thr Lys Leu Glu Leu Lys
            100                 105                 110

<210> SEQ ID NO 50
<211> LENGTH: 24
<212> TYPE: DNA
<213> ORGANISM: Mus musculus

<400> SEQUENCE: 50
```

```
gaagtgcagc tggtggagtc tggg                                          24

<210> SEQ ID NO 51
<211> LENGTH: 20
<212> TYPE: DNA
<213> ORGANISM: Mus musculus

<400> SEQUENCE: 51
gatgttgtga tgacccaaac                                               20

<210> SEQ ID NO 52
<211> LENGTH: 24
<212> TYPE: DNA
<213> ORGANISM: Mus musculus

<400> SEQUENCE: 52
ctgatcagtc caactgttca ggac                                          24

<210> SEQ ID NO 53
<211> LENGTH: 16
<212> TYPE: DNA
<213> ORGANISM: Artificial Sequence
<220> FEATURE:
<223> OTHER INFORMATION: sequencing primer
<220> FEATURE:
<221> NAME/KEY: misc_feature
<223> OTHER INFORMATION: Description of Artificial Sequence: Sequencing
      oligonucleotide.

<400> SEQUENCE: 53
gtaaaacgac ggccag                                                   16

<210> SEQ ID NO 54
<211> LENGTH: 17
<212> TYPE: DNA
<213> ORGANISM: Artificial Sequence
<220> FEATURE:
<223> OTHER INFORMATION: sequencing primer
<220> FEATURE:
<221> NAME/KEY: misc_feature
<223> OTHER INFORMATION: Description of Artificial Sequence: Sequencing
      oligonucleotide.

<400> SEQUENCE: 54
caggaaacag ctatgac                                                  17

<210> SEQ ID NO 55
<211> LENGTH: 49
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence: PCR - SOE
      primer for 5' 5109 VH region, including an Sfi I restriction
      endonuclease site.

<400> SEQUENCE: 55
gaagagcggc ccagccggcc atggccgaag tgcagctggt ggagtctgg               49

<210> SEQ ID NO 56
<211> LENGTH: 74
<212> TYPE: DNA
<213> ORGANISM: Artificial Sequence
<220> FEATURE:
<223> OTHER INFORMATION: primer for PCR-SEO
```

```
<220> FEATURE:
<221> NAME/KEY: misc_feature
<223> OTHER INFORMATION: Description of Artificial Sequence:  PCR - SOE
      primer for 3' 5109 VH region including linker segment of scFv for
      assembly PCR reaction with 5109 VL.

<400> SEQUENCE: 56
cgatccgcca ccgccgctgc cacctccgcc tgaaccgcct ccaccactcg agacagtgac    60
cagcgcccct tggc                                                      74

<210> SEQ ID NO 57
<211> LENGTH: 66
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence:  PCR - SOE
      primer for 5' 5109 VL region, including overlap into scFv linker
      segment.

<400> SEQUENCE: 57
ggttcaggcg gaggtggcag cggcggtggc ggatcgtctg atgttgtgat gacccaaact    60
ccactc                                                               66

<210> SEQ ID NO 58
<211> LENGTH: 87
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence:  PCR - SOE
      primer for 3' 5109 VL region, Ser version, including a Not I
      restriction endonuclease site.

<400> SEQUENCE: 58
ggaaggagcg gccgctttca gctccagctt ggtcccagca ccgaacgtgt gaggaaaatg    60
tgtaccttgg gagcaataat aaactcc                                        87

<210> SEQ ID NO 59
<211> LENGTH: 36
<212> TYPE: DNA
<213> ORGANISM: Artificial Sequence
<220> FEATURE:
<223> OTHER INFORMATION: primer for PCR-SOE
<220> FEATURE:
<221> NAME/KEY: misc_feature
<223> OTHER INFORMATION: Description of Artificial Sequence:  PCR - SOE
      primer for 3' 5109 VL region, Cys version, including a Not I
      restriction endonuclease site.

<400> SEQUENCE: 59
ggaaggagcg gccgctttca gctccagctt ggtagc                              36

<210> SEQ ID NO 60
<211> LENGTH: 21
<212> TYPE: DNA
<213> ORGANISM: Homo sapiens

<400> SEQUENCE: 60
ctcttctgag atgagttttt g                                              21

<210> SEQ ID NO 61
```

```
<211> LENGTH: 18
<212> TYPE: DNA
<213> ORGANISM: Artificial Sequence
<220> FEATURE:
<223> OTHER INFORMATION: sequencing primer
<220> FEATURE:
<221> NAME/KEY: misc_feature
<223> OTHER INFORMATION: Description of Artificial Sequence: Sequencing
      oligonucleotide. Primes in Gly4Ser linker region.

<400> SEQUENCE: 61
gaggcggttc aggcggag                                                       18

<210> SEQ ID NO 62
<211> LENGTH: 18
<212> TYPE: DNA
<213> ORGANISM: Artificial Sequence
<220> FEATURE:
<223> OTHER INFORMATION: sequencing primer
<220> FEATURE:
<221> NAME/KEY: misc_feature
<223> OTHER INFORMATION: Description of Artificial Sequence: Sequencing
      oligonucleotide. Primes in Gly4Ser linker region.

<400> SEQUENCE: 62
gatccgccac cgccgctg                                                       18

<210> SEQ ID NO 63
<211> LENGTH: 289
<212> TYPE: PRT
<213> ORGANISM: Artificial Sequence
<220> FEATURE:
<223> OTHER INFORMATION: 5109 scFv from clone p5109C scFv7
<220> FEATURE:
<221> NAME/KEY: misc_feature
<223> OTHER INFORMATION: Description of Artificial Sequence: 5109
      VH - VL scFv.
<220> FEATURE:
<221> NAME/KEY: SIGNAL
<222> LOCATION: (1)..(22)
<223> OTHER INFORMATION: pCANTAB6 signal peptide; Val at position 1 is
      most likely initiat or Met.
<220> FEATURE:
<221> NAME/KEY: DOMAIN
<222> LOCATION: (23)..(138)
<223> OTHER INFORMATION: 5109 VH domain.
<220> FEATURE:
<221> NAME/KEY: DOMAIN
<222> LOCATION: (139)..(154)
<223> OTHER INFORMATION: 16 amino acid linker.
<220> FEATURE:
<221> NAME/KEY: DOMAIN
<222> LOCATION: (155)..(266)
<223> OTHER INFORMATION: 5109 VL domain.
<220> FEATURE:
<221> NAME/KEY: SITE
<222> LOCATION: (270)..(279)
<223> OTHER INFORMATION: myc tag.
<220> FEATURE:
<221> NAME/KEY: SITE
<222> LOCATION: (284)..(289)
<223> OTHER INFORMATION: His tag.

<400> SEQUENCE: 63

Met Lys Lys Leu Leu Phe Ala Ile Pro Leu Val Val Pro Phe Tyr Ala
1               5                   10                  15

Ala Gln Pro Ala Met Ala Glu Val Gln Leu Val Glu Ser Gly Gly Gly
            20                  25                  30

Ser Val Gln Pro Gly Gly Ser Leu Lys Leu Ser Cys Ala Ala Ser Gly
        35                  40                  45

Phe Thr Phe Asn Thr Tyr Gly Met Ser Trp Val Arg Gln Thr Pro Asp
```

-continued

```
                50                  55                  60
Lys Arg Leu Glu Trp Val Ala Thr Ile Asn Ser Asn Gly Gly Leu Thr
 65                  70                  75                  80

Phe Tyr Ala Asp Ser Val Lys Gly Arg Phe Thr Ile Ser Arg Asp Asn
                 85                  90                  95

Ala Lys Asn Thr Leu Tyr Leu Gln Met Asn Arg Leu Lys Ser Gly Asp
            100                 105                 110

Ser Gly Met Tyr Tyr Cys Val Arg Gly Tyr Ser Asn Tyr Ala Arg Trp
            115                 120                 125

Gly Gln Gly Ala Leu Val Thr Val Ser Ser Gly Gly Gly Ser Gly
        130                 135                 140

Gly Gly Gly Ser Gly Gly Gly Ser Ser Asp Val Val Met Thr Gln
145                 150                 155                 160

Thr Pro Leu Thr Leu Ser Val Thr Ile Gly Gln Ser Ala Ser Ile Ser
                165                 170                 175

Cys Lys Ser Ser Gln Ser Leu Leu Gly Ser Asp Gly Leu Thr Tyr Leu
            180                 185                 190

Ile Trp Leu Leu Gln Arg Pro Gly Gln Ser Pro Lys Arg Leu Ile Phe
        195                 200                 205

Leu Val Ser Glu Leu Asp Ser Gly Val Pro Asp Arg Phe Thr Gly Ser
    210                 215                 220

Gly Ser Gly Thr Asp Phe Thr Leu Lys Ile Ser Arg Ala Glu Ala Glu
225                 230                 235                 240

Asp Leu Gly Val Tyr Tyr Cys Cys Gln Gly Thr His Phe Pro His Thr
                245                 250                 255

Phe Gly Ala Gly Thr Lys Leu Glu Leu Lys Ala Ala Ala Glu Gln Lys
            260                 265                 270

Leu Ile Ser Glu Glu Asp Leu Asn Ala Ala Ala His His His His His
        275                 280                 285

His
```

<210> SEQ ID NO 64
<211> LENGTH: 21
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Type II human collagen fragment with 4Hyp.
<220> FEATURE:
<221> NAME/KEY: MISC_FEATURE
<222> LOCATION: (1)..(21)
<223> OTHER INFORMATION: Xaa is any amino acid.

<400> SEQUENCE: 64

```
Glu Lys Gly Glu Pro Gly Asp Asp Ala Pro Ser Gly Ala Glu Gly Pro
 1               5                  10                  15

Xaa Gly Pro Gln Gly
            20
```

<210> SEQ ID NO 65
<211> LENGTH: 62
<212> TYPE: DNA
<213> ORGANISM: Artificial Sequence
<220> FEATURE:
<223> OTHER INFORMATION: primer for PCR
<220> FEATURE:
<221> NAME/KEY: misc_feature
<223> OTHER INFORMATION: Description of Artificial Sequence: PCR spiking oligonucleotide.

```
<220> FEATURE:
<221> NAME/KEY: misc_difference
<222> LOCATION: (25)..(51)
<223> OTHER INFORMATION: 9A4 scFv PCR spiking oligonucleotide.  Level of
      spiking = 10% with nucleotide other than shown in this segment.
      Sequence shown represents original.

<400> SEQUENCE: 65
gactgtgaga gtggtgcctt ggccccagta gtcaaggcta ccgcccctag cacagaaata      60
tg                                                                    62

<210> SEQ ID NO 66
<211> LENGTH: 26
<212> TYPE: DNA
<213> ORGANISM: Mus musculus
<220> FEATURE:
<221> NAME/KEY: V_region
<222> LOCATION: (1)..(26)
<223> OTHER INFORMATION: Portion of the JH segment of the 9A4 VH used
      as a PCR primer.

<400> SEQUENCE: 66
gccaaggcac cactctcaca gtctcc                                          26

<210> SEQ ID NO 67
<211> LENGTH: 21
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Type II Collagen Fragment with 4Hyp.
<220> FEATURE:
<221> NAME/KEY: MISC_FEATURE
<222> LOCATION: (1)..(21)
<223> OTHER INFORMATION: Xaa is any amino acid.
<220> FEATURE:
<221> NAME/KEY: MOD_RES
<222> LOCATION: (6)..(6)
<223> OTHER INFORMATION: Type II Collagen Fragment with 4Hyp.
<220> FEATURE:
<221> NAME/KEY: MOD_RES
<222> LOCATION: (9)..(9)
<223> OTHER INFORMATION: Type II Collagen Fragment with 4Hyp.
<220> FEATURE:
<221> NAME/KEY: MOD_RES
<222> LOCATION: (18)..(18)
<223> OTHER INFORMATION: Type II Collagen Fragment with 4Hyp.

<400> SEQUENCE: 67

Gly Pro Xaa Gly Pro Xaa Gly Lys Xaa Gly Asp Asp Gly Glu Ala Gly
1               5                   10                  15

Lys Xaa Gly Lys Ala
            20

<210> SEQ ID NO 68
<211> LENGTH: 21
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Type II Collagen Fragment with 4Hyp.
<220> FEATURE:
<221> NAME/KEY: MISC_FEATURE
<222> LOCATION: (1)..(21)
<223> OTHER INFORMATION: Xaa is any amino acid.
<220> FEATURE:
<221> NAME/KEY: MOD_RES
<222> LOCATION: (18)..(18)
<223> OTHER INFORMATION: Type II Collagen Fragment with 4Hyp.
```

```
<220> FEATURE:
<221> NAME/KEY: MOD_RES
<222> LOCATION: (21)..(21)
<223> OTHER INFORMATION: Type II Collagen Fragment with 4Hyp.

<400> SEQUENCE: 68

Gly Pro Xaa Gly Pro Arg Gly Arg Ser Gly Glu Thr Gly Pro Ala Gly
1               5                   10                  15

Pro Xaa Gly Asn Xaa
            20

<210> SEQ ID NO 69
<211> LENGTH: 22
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Type II Collagen Fragment with 4Hyp.
<220> FEATURE:
<221> NAME/KEY: MISC_FEATURE
<222> LOCATION: (1)..(22)
<223> OTHER INFORMATION: Xaa is any amino acid.
<220> FEATURE:
<221> NAME/KEY: MOD_RES
<222> LOCATION: (12)..(12)
<223> OTHER INFORMATION: Type II Collagen Fragment with 4Hyp.
<220> FEATURE:
<221> NAME/KEY: MOD_RES
<222> LOCATION: (15)..(15)
<223> OTHER INFORMATION: Type II Collagen Fragment with 4Hyp.
<220> FEATURE:
<221> NAME/KEY: MOD_RES
<222> LOCATION: (18)..(18)
<223> OTHER INFORMATION: Type II Collagen Fragment with 4Hyp.

<400> SEQUENCE: 69

Gly Ala Xaa Gly Pro Gln Gly Phe Gln Gly Asn Xaa Gly Glu Xaa Gly
1               5                   10                  15

Glu Xaa Gly Val Ser Tyr
            20

<210> SEQ ID NO 70
<211> LENGTH: 20
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Type II Collagen Fragment with 4Hyp.
<220> FEATURE:
<221> NAME/KEY: MISC_FEATURE
<222> LOCATION: (1)..(20)
<223> OTHER INFORMATION: Xaa is any amino acid.
<220> FEATURE:
<221> NAME/KEY: MOD_RES
<222> LOCATION: (12)..(12)
<223> OTHER INFORMATION: Type II Collagen Fragment with 4Hyp.
<220> FEATURE:
<221> NAME/KEY: MOD_RES
<222> LOCATION: (15)..(15)
<223> OTHER INFORMATION: Type II Collagen Fragment with 4Hyp.
```

-continued

```
<220> FEATURE:
<221> NAME/KEY: MOD_RES
<222> LOCATION: (18)..(18)
<223> OTHER INFORMATION: Type II Collagen Fragment with 4Hyp.

<400> SEQUENCE: 70

Gly Glu Pro Gly Asp Asp Ala Gly Pro Ser Gly Ala Glu Gly Pro Xaa
1               5                   10                  15

Gly Pro Gln Gly
            20
```

ASSAYS FOR MEASUREMENT OF TYPE II COLLAGEN FRAGMENTS IN URINE

REFERENCE TO RELATED APPLICATION

This application is a continuation-in-part of U.S. patent application Ser. No. 09/184,658, filed Nov. 2, 1998 now U.S. Pat. No. 6,030,792, the entirety of which is hereby incorporated by reference herein.

FIELD OF THE INVENTION

This invention relates to methods for detecting type II collagen fragments in biological media. More specifically, it relates to methods for quantifying protein fragments found in urine resulting from cleavage of type II collagen.

BACKGROUND OF THE INVENTION

The physiological turnover of articular cartilage represents a fine balance between synthesis and degradation. It is a feature of normal growth and development and maintenance of cartilage in the adult. Net cartilage loss is a feature of arthritis. It is strongly associated with disability and a low quality of life. Cartilage destruction in rheumatoid arthritis and osteoarthritis is currently diagnosed based on combined clinical symptoms and radiological findings. Damage to articular cartilage occurs early in the disease, long before it can be detected radiologically; damage is detected radiologically only after there is extensive and probably irreversible cartilage loss. Therefore, it is of critical importance that clinicians have biochemical markers for early diagnosis of cartilage damage so therapy can be initiated early, before extensive damage is done. Furthermore, such markers can be used in the design of clinical trials in the selection of subjects for enrollment who have a higher likelihood of rapid progression. In addition, treatment effects could be monitored in a timely manner. TIINE analysis may also provide information by which compound effectiveness may be measured.

Type II collagen constitutes the bulk of the fibrillar backbone of the cartilage matrix, just as type I collagen forms the fibrillar organization of the extracellular matrix of most other tissues such as skin, bone, ligaments and tendons.The destruction of articular cartilage during arthritic disease is due, in part, to the degradation of the extracellular matrix, which is composed primarily of fibrillar type II collagen and aggregating proteoglycans. In articular cartilage, type II collagen fibrils are responsible for the tensile strength and structure whereas the proteoglycans provide the compressive stiffness necessary for normal articulation and function. The precise mechanisms by which these connective tissue components are degraded are not fully understood. In mammals, an important mechanism involves the collagenases, MMP-1, MMP-8, MMP-13 and MT1-MMP, which are a group of enzymes capable of site-specific cleavage of helical (native) collagen. All three type of collagen are composed of a tightly wound triple helix, which in man, are cleaved extracellularly by the collagenases to produce ¾ and ¼ length cc-chain fragments that are identifiable by polyacrylamide gel electrophoresis.

SUMMARY OF THE INVENTION

In a first aspect, the present invention provides a method for monitoring urine for type II collagen fragments, said method comprising contacting said urine with a capture antibody, wherein said capture antibody binds specifically to type II collagen fragments, to the substantial exclusion of any binding to type I or III collagen fragments, contacting said urine with a detection antibody, wherein said detection antibody binds specifically to collagenase-generated collagen fragments, and detecting the amount of type II collagen fragments bound to said capture and detection antibodies.

In a preferred embodiment of the first aspect, the detection antibody is active against the sequences set forth in SEQ ID NOS: 1 and 2.

In another preferred embodiment of the first aspect, the detection antibody has a $V_H$ sequence at least 95% homologous to that set forth in SEQ ID NO: 32, and a $V_L$ sequence at least 95% homologous to that set forth in SEQ ID NO: 33.

In another preferred embodiment of the first aspect, the detection antibody has the same CDRs as the $V_H$ sequence set forth in SEQ ID NO: 32, and the same CDRs as the $V_L$ sequence set forth in SEQ ID NO: 33.

In another preferred embodiment of the first aspect, the capture antibody is active against the sequences set forth in SEQ ID NOS: 3 and 4.

In another preferred embodiment of the first aspect, the capture antibody has a $V_H$ sequence at least 95% homologous to that set forth in SEQ ID NO: 48, and a $V_L$ sequence at least 95% homologous to that set forth in SEQ ID NO: 49.

In another preferred embodiment of the first aspect, the capture antibody has the same CDRs as the $V_H$ sequence set forth in SEQ ID NO: 48, and the same CDRs as the $V_L$ sequence set forth in SEQ ID NO: 49.

Those skilled in this art will recognize that the order of contacting the antibodies with the biological media may be reversed.

Furthermore, in certain embodiments, this aspect of the invention comprises a method for monitoring urine for type II collagen fragments as described above, wherein said contacting steps occur simultaneously.

In another preferred embodiment of the first aspect, the antibody contacting steps occur sequentially, and after the contacting step involving the capture antibody, and prior to the contacting step involving the detection antibody, said capture antibody is immobilized onto a magnetic material.

In another preferred embodiment of the first aspect, the method as described above includes the further steps of contacting a series of control samples with said capture antibody, contacting said control samples with said detection antibody, and detecting the amount of type II collagen fragments in said control samples bound to said capture and detection antibodies.

In a second aspect of the present invention, there is provided a kit for monitoring urine for type II collagen fragments, said kit comprising a capture antibody, wherein said capture antibody binds specifically to type II collagen fragments, to the substantial exclusion of any binding to type I or III collagen fragments, a detection antibody, wherein said detection antibody binds specifically to collagenase-generated collagen fragments, a container, and instructions describing a method of using said first antibody and said second antibody to monitor biological media for type II collagen fragments.

In a preferred embodiment of the second aspect, said detection antibody has a $V_H$ sequence at least 95% homologous to that set forth in SEQ ID NO: 32, and a $V_L$ sequence at least 95% homologous to that set forth in SEQ ID NO: 33, and said capture antibody has a $V_H$ sequence at least 95% homologous to that set forth in SEQ ID NO: 48, and a $V_L$ sequence at least 95% homologous to that set forth in SEQ ID NO: 49.

In another preferred embodiment of the second aspect, said detection antibody has the same CDRs as the $V_H$ sequence set forth in SEQ ID NO: 32, and the same CDRs as the $V_L$ sequence set forth in SEQ ID NO: 33, and said capture antibody has the same CDRs as the $V_H$ sequence set forth in SEQ ID NO: 48, and the same CDRs as the $V_L$ sequence set forth in SEQ ID NO: 49.

In another preferred embodiment of the second aspect, said kit further comprises a positive control fluid comprising control urine containing a known amount of type II collagen fragments, and a dilution fluid comprising control urine for diluting samples being tested with said kit.

In a third aspect of the present invention there is provided a biosensor chip for detecting the presence of an immunological binding event, wherein said chip comprises a first antibody active against the sequences set forth in SEQ ID NOS: 1 or 2, or a second antibody active against the sequences set forth in SEQ ID NOS: 3 or 4.

In a fourth aspect of the present invention there is provided a method of diagnosing a patient for a disease state associated with the degradation of type II collagen, said method comprising the step of detecting the presence of atypically large amounts of type II collagen fragments in urine collected from said patient.

In a fifth aspect of the present invention there is provided a method of performing a clinical trial to evaluate a drug believed to be useful in treating a disease state associated with the degradation of type II collagen, said method comprising measuring the level of type II collagen fragments in urine collected from a set of patients, administering said drug to a first subset of said patients, and a placebo to a second subset of said patients, repeating said measuring step after the administration of said drug or said placebo, and determining if said drug is reducing the amount of type II collagen fragments present in said urine of said first subset of patients to a degree that is statistically significant as compared to any reduction occurring in said second subset of patients, wherein a statistically significant reduction indicates that said drug is useful in treating said disease state.

Useful in the present invention is a hybridoma cell line or *E. coli* culture that produces a monoclonal antibody that binds to peptides consisting essentially of the structure as set forth in the Sequence Listing as SEQ ID NO: 1 or SEQ ID NO: 2, the cell line having the identifying characteristics of ATCC HB-12436.

Also useful in the present invention is a hybridoma cell line or *E. coli* culture that produces a monoclonal antibody that binds to peptides consisting essentially of the structure as set forth in the Sequence Listing as SEQ ID NOS: 3 or 4, the cell line having the identifying characteristics of ATCC HB-12435.

FIG. 1 is a standard curve of peptide 130 concentrations from the 9A4 capture/Bt-5109 detection sandwich assay, with 9A4 as the capture antibody.

FIG. 2 is a standard curve of peptide 130 concentrations from the 9A4 capture/Bt-5109 detection sandwich assay, with 5109 as the capture antibody.

DETAILED DESCRIPTION OF THE INVENTION

Figure 3:
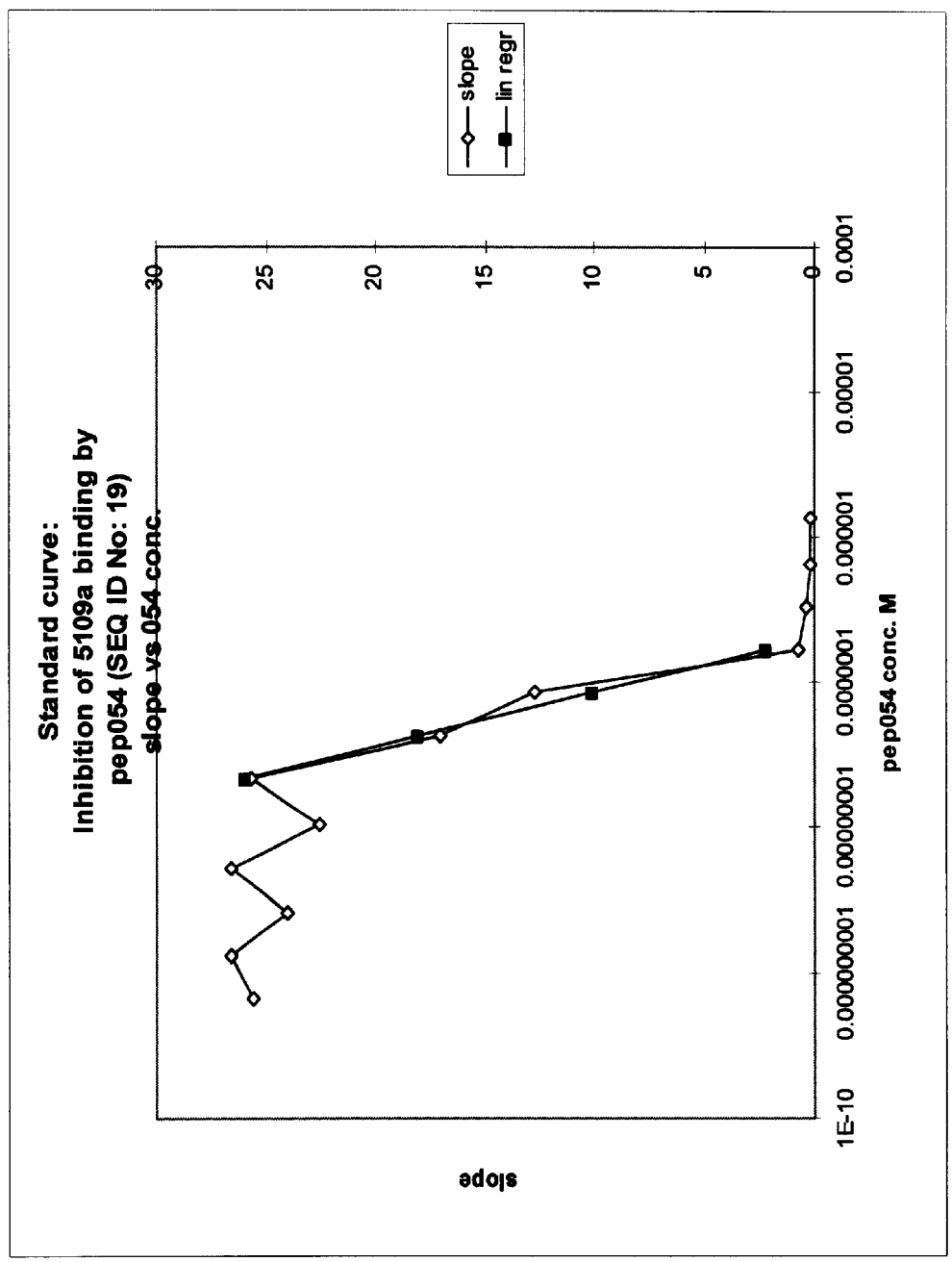
FIG. 3 is a standard curve for inhibition of 5109a binding by peptide 054 (SEQ ID NO: 19).

Type II collagen is the structural protein that gives articular cartilage its tensile strength and shear resistance. It also provides the structural basis for the containment of proteoglycan that imparts compressive resistance and in doing so directly determines the form of the osmotically pressurized cartilage. Thus the structural integrity of type II collagen is a major determinant of the physical properties and the durability of articular cartilage.

The progressive failure of articular cartilage is one of the hallmarks of arthritic disease. Where that failure is based on changes in the type II collagen structure, it would be advantageous to have methodology to measure specifically the breakdown of type II collagen. Fragments of type II collagen from articular cartilage are released into the synovial fluid, then transported through the lymph, blood, and released in the urine. Measurement of released fragments would provide a method for monitoring type II collagen breakdown to detect the onset of arthritic disease and measure disease progression. Moreover, it would also be useful to measure the effect of disease modifying therapy on type II collagen breakdown during disease.

A variety of methods have been utilized to monitor collagen breakdown. In mammalian tissues, collagenase appears to be the rate-limiting extracellular enzyme involved in extracellular breakdown of type II collagen (1). Collagenase fragmentation of collagen into ¾ and ¼ size pieces was identified as early as 1967 (2,3). Currently, there are four identified mammalian collagenases (MMP-1, MMP-8, MMP-13, and MT1-MMP) involved in the initial cleavage of type II collagen (4,5,29). Other enzymes are involved in further fragmentation of type II collagen. Lysosomal breakdown of the fibrillar collagens is known to occur in bone and liver (6,7). Since collagen is one of the few proteins characterized by a high hydroxyproline content, measurement of urinary hydroxyproline has been examined as a measure of collagen turnover (8). However, the method has not been found useful for measuring breakdown of type II collagen, since most of the signal is derived from type I and type III collagens that are found in large amounts in skin, bone, and connective tissues. Therefore, it is of no value for monitoring type II collagen since it provides only an extremely small portion of the daily urinary secretion of hydroxyproline (8). Thus, efforts to monitor collagen or breakdown products of collagen have focused on immunological detection methods.

Antibodies can discriminate collagen fragments unique to a collagen type and cleavage site and potentially monitor the specific mode of collagen breakdown (9). Polyclonal and monoclonal antibodies have been prepared against type I and III collagen or their fragments, and assays have been prepared for the collagen breakdown products of type I and type III collagens, for example, see Eyre (10). In fact, these assays are routinely used in the clinic to monitor bone resorption. Relatively few methods have been reported using antibodies against breakdown products of type II collagen.

Polyclonal and monoclonal antibodies have been prepared against type II collagen (9,11–13). These antibodies have been utilized for the detection of intact type II collagen rather than the quantitative determination of collagen fragments. Eyre, however, (14) has prepared monoclonal antibodies against type II collagen fragments containing the crosslinking residues. He developed an assay for breakdown of type II collagen based on the crosslink fragment containing a type II collagen-specific sequence similar to his issued patent (10). Dodge and Poole prepared polyclonal antibodies against denatured type II collagen that were unreactive with native type II or other collagens (15,16). The epitope was sequenced and later Hollander and Poole (17,18,19,) prepared a competitive antibody assay against the type II collagen fragments having the sequences set forth in the Sequence Listing as SEQ ID NOS: 12 and 13 using a monoclonal antibody. Hollander and Croucher (20) also made a capture ELISA using antibodies directed against peptides outlined in the Sequence Listing as SEQ ID NO: 67, 68, or 69. Billinghurst et al. (21) have prepared polyclonal antibody against the collagen cleavage site neoepitope of type II collagen (having the sequence set forth in the Sequence Listing as SEQ ID NO: 2) and have prepared a competitive type II collagen assay. Srinivas, Barrach, and Chichester (22–24) have prepared multiple monoclonal antibodies for a type II collagen assay using the cyanogen bromide fragments of type II collagen as antigen. Although the epitopes reactive with the antibody have not been identified (25), they too are able to assay type II collagen.

A capture ELISA is a reliable method for obtaining high specificity since it is based on two antibodies coordinately recognizing two different amino acid epitopes in the same molecule. As the antibody binding site contains as few as six amino acids, sequences as small as 15 to 20 amino acids can be recognized by two antibodies in a capture assay. Competitive assays use a single antibody and thus allow measurement of polypeptides as small as 6–8 amino acids, but they lack the specificity of the dual antibody measurement. In addition, competitive assays lack the sensitivity of capture ELISAs which often have a 100–10,000 times lower limit of detection. Thus capture ELISAs provide a preferred method for measuring metabolic fragments of proteins. For example, a capture ELISA has been used to measure breakdown fragments of the structural protein elastin in blood (26). A capture ELISA has been used to measure the 21 amino acid biologically active peptide endothelin (27). A pair of capture ELISAs have been used to measure different metabolic fragments of the 28 amino acid glucagon peptide (28). Based on such results, a minimal 22 amino acid peptide fragment was selected that could be used to construct a capture ELISA to measure collagenase-dependent metabolism of type II collagen.

This invention provides two types of assays of type II collagen metabolism. Both assays are based on an antibody (polyclonal, monoclonal, or genetically engineered antibody) against a defined sequence of type II collagen against which antibodies have not been previously prepared. The sequence is rich in acidic residues, i.e., the sequence set forth in the Sequence Listing as SEQ ID NO: 3 from which a deletion has been made at the C-terminus by 1 residue. As no mammalian extracellular aspartyl or glutamyl endopeptidases have been yet described, collagen fragments rich in acidic residues are expected to survive further metabolism. Such fragments should therefore be measurable in the body fluids. Antibody against those residues or a collagen fragment containing those residues would provide a general method of detection of type II fragments in body fluids independent of the method of generation of the collagen metabolite. This invention provides monoclonal antibody 5109 and genetically engineered variants of 5109 that are specific for the type II collagen sequence and bind to collagen fragments containing the sequence.

The first assay is a general method for assessing the breakdown of type II collagen. This assay provides a general competitive method for quantitating the amount of the sequence set forth in the Sequence Listing as SEQ ID NO: 3 from which a deletion has been made at the C-terminus by 1 residue, and its closely related congeners.

For the second assay, an additional antibody was made against the sequence set forth in the Sequence Listing as SEQ ID NO: 14. There is a free C-terminal carboxyl group on the glycine (residue 9 of SEQ ID NO: 14). This sequence is obtained when collagenase cleaves type II collagen and therefore it is classified as a neoepitope, i.e., it is not present in the native sequence (the sequence set forth in the Sequence Listing as SEQ ID NO: 15, continues -GPOGPQG/LAG-where collagenase cleaves at the vertical bar), but arises when collagen is cleaved by collagenase. Polyclbnal antibodies against that sequence have been previously reported (22). Monoclonal antibody 9A4 and genetically engineered derivatives therefrom react with the neoepitope sequence set forth in the Sequence Listing as SEQ ID NO: 2, but fail to react with uncleaved type II collagen or type I collagen. While the neoepitope sequence is unique to type II collagen when cleaved by collagenase, a homologous and weakly cross-reactive sequence is generated in type I collagen when cleaved by collagenase (SEQ ID NO: 16 as set forth in the Sequence Listing). This is also true for type III collagen; it generates the sequence set forth in the Sequence Listing as SEQ ID NO: 2 when cleaved by collagenase. Thus the neoepitope antibody lacks full specificity for type II collagen and would fail to selectively detect cleavage of type II collagen by collagenase if used alone. However, when antibody 5109 and antibody 9A4 are combined in a sandwich assay the two antibodies together can selectively detect type II collagen metabolites generated by collagenase. Moreover, an advantage that the sandwich type of assay provides in this invention is a 100 fold lower limit of detection compared to a simple competitive assay based on 9A4 alone. The sandwich assay format with the antibodies described in this invention thus provides a unique method for monitoring type If collagen metabolism by collagenase in normal and pathological conditions, which has not been previously described.

Alone, antibody 9A4 is a novel monoclonal antibody that has use for the detection of collagenase cleaved fragments of type I or type II or type III collagen, so long as it is not necessary to distinguish the collagen type.

REFERENCES

1. Harris et al., *N. Engl. J. Med.*, 291:557–63, 605–09, 652–61 (1974).
2. Nagai et al., *Biochemistry*, 5:3123–3130 (1966).
3. Sakai et al., *Biochemistry*, 6:518–528 (1967).
4. Pendas et al., *Genomics*, 26:615–18 (1995).
5. Mitchell et al., *J. Clin. Invest.*, 97:761–68 (1996).
6. Maciewicz et al., *FEBS Lett.*, 269:189–93 (1990).
7. van Noorden et al., *Bioc. Biop. Res. Comm.*, 178:178–84 (1991).
8. Kivirikko, Int. Rev. *Connect. Tissue Res.*, 5:93–163 (1970).
9. Timpl, *Methods Enzymol.*, 82:472–98 (1982).
10. Eyre, U.S. Pat. No. 5,320,970 (1994).
11. Holmdahl et al., *Immunology*, 61:369–74 (1987).
12. Punjabi et al., *J. Immunol.*, 141:3819–22 (1988).
13. Jasin et al., *J. Clin. Invest.*, 87:1531–36 (1991).
14. Norlund et al., *Trans. Orthoped. Res. Assoc.*, 22:313 (1997).
15. Dodge et al., *J. Clin. Invest.*, 83:647–61 (1989).

16. Dodgeetal., *Matrix*, 11:330–38(1991).
17. Poole, PCT Publication WO 94/14070 (1994).
18. Hollander et al., *J. Clin. Invest.*, 93:1722–32 (1994).
19. Hollander et al., *J. Clin. Invest.*, 96:2859–69 (1995).
20. Hollander et al., PCT Publication WO 98/3523520 (1998).
21. Billinghurst et al., *J. Clin. Invest.*, 99:153445 (1997).
22. Srinivas et al., *J. Immunol. Meth.*, 159:53–62 (1993).
23. Srinivas et al., *Agents Actions*, 41:193–99 (1994).
24. Srinivas et al., *Immunol. Invest.*, 23:85–98 (1994).
25. Chichester et al., *Pharm. Pharmacol.*, 48:694–98 (19
26. Baydanoff et al., *Atherosclerosis*, 66:163–68 (1987).
27. Hamaoki et al., *Hybridoma*, 9:63–69 (1990).

DEFINITIONS

Immunoglobulin (Ig): A natural tetrameric protein composed of two light chains of circa 23 kD and two heavy chains of circa 53–70 kD depending on the amino acid sequence and degree of glycosylation. Multimers of the tetrameric protein are also formed (IgM and IgA). There are two classes of light chains, kappa (κ) and lambda (λ), and several classes of heavy chains gamma (γ), mu (μ), alpha (α), delta (δ), and epsilon (ε). There are also subclasses. Each chain, whether a light chain or heavy chain, is made up of two parts. The first part, beginning from the N-terminus of either chain, is called the variable domain. The C-terminal half of the light chain is called the constant region of the light chain and it is the primary determinant whether the light chain is a κ or λ type. The constant region of the heavy chain comprise approximately the C-terminal three-fourths of the heavy chain and determines the class of the immunoglobulin molecule ($IgG_1$, IgM, etc.), i.e., a γ heavy chain corresponds to an IgG and a μ heavy chain corresponds to an IgM, etc.

$V_L$ and $V_H$: The amino acid sequence of the variable domain of the light chain ($V_L$) and the variable domain of the heavy chain ($V_H$) together determine the binding specificity and the binding constant of the immunoglobulin molecule. The variable domain comprises circa half the length of the light chain and circa a quarter of the length of the heavy chain and for both chains, begins at the N-terminus of the chain. The variable regions each contain three (3) hypervariable segments known as the complementarity determining regions or CDRs.

CDR and FR: Each variable domain, $V_L$ or $V_H$, is comprised of three CDRs: CDR1, CDR2, and CDR3. The intervening sequence segments before, between, and after the CDRs are known as framework segments (FR). Each $V_L$ and $V_H$ is comprised of four FR segments FR1, FR2, FR3, and FR4.

$V_κ$ and $V_λ$: The $V_L$ domain is either κ or λ, depending on which constant region ($C_κ$ or $C_λ$) is used during the productive rearrangement of the light chain ($VJC_κ$ or $VJC_λ$).

Antibody: Antibodies are specific immunoglobulin molecules produced by B-cells of the immune system in response to challenges by proteins, glycoproteins, virus cells, chemicals coupled to carriers, and other substances. An antibody is simply an immunoglobulin molecule for which its binding partner is known. The substance to which the antibody binds is called an antigen. The binding of such antibodies to its antigen is highly refined and the multitude of specificities capable of being generated by changes in amino acid sequence in the variable domains of the heavy and light chains is remarkable.

Polyclonal antibody: Normal immunization leads to a wide variety of antibodies against the same antigen. Although each B lymphocyte normally produces one immunoglobulin molecule of a defined amino acid sequence, in an immune response, many B lymphocytes are stimulated to make immunoglobulin molecules that react with the antigen, i.e., antibodies. These different antibodies are characterized by different amino acid sequences in the variable regions of the immunoglobulin molecule which result in differences in the fine specificity and affinity of binding. Such antibodies are called polyclonal antibodies to emphasize the variety of binding specificities and binding constants which arise from the variety of amino acid sequences found in the different immunoglobulin molecules utilized in the immune response.

Monoclonal antibody (mAb): A B lymphocyte producing a single antibody molecule can be hybridized with an immortal B lymphocyte cell line, i.e., a myeloma, to derive an antibody producing immortal cell line, i.e., a hybridoma. The hybrids thus formed are segregated into single genetic strains by selection, dilution, subdloning, and regrowth, and each strain thus represents a single genetic line. It produces a single antibody of a unique sequence. The antibody produced by such a cell line is called "monoclonal antibody" or mAb, referencing its pure genetic parentage and differentiating it from polyclonal antibody, produced from a mixed genetic background, i.e., multiple B cells. Because a mAb is a pure chemical reagent it gives consistent, uniform results in immune tests. Moreover, because the mAb is produced by an immortal cell line, reagent supply is not limiting. For these reasons, a mAb is much preferred over polyclonal antibodies for diagnostic purposes.

Genetically engineered antibody: As the binding specificity of an antibody resides in the variable regions of the light and heavy chains, antibodies can be genetically engineered to change or remove the constant regions and, if done properly, it can result in an antibody molecule with different properties and molecular weight, but with the same or very similar antigen binding properties. For example, the $V_L$ and $V_H$ genes can be cloned and assembled (or $V_H$ and $V_L$) with an appropriate linker between them. Such a new genetically engineered molecule is called a single chain antibody (abbreviated scFv) and typically has a molecular weight of 25–28 kD depending on the design of the linker and the addition of other sequences to help in purification, stability, trafficking, detection, etc. Multimers of the single chain antibody can also be made by appropriate use of linkers in which the order of each $V_H/N_L$ pair may vary. In addition, some changes in the amino acid sequence of the $V_L$ and $V_H$ region can be made while retaining desirable antigen binding properties. It can be seen that an infinite variety of genetically engineered antibodies can be derived from the original antibody sequence which retain binding specificity to the antigen, but which are tailored to fulfill specific requirements. Other examples of genetically engineered antibodies include, but are not limited to: Fab, $F(ab')_2$, chimeric antibodies, humanized antibodies, etc. For a review, see Winter and Milstein, *Nature*, 349:243–299 (1991).

Bispecific antibody: Normally an IgG antibody has two identical light chains and two identical heavy chains. There are therefore two identical antibody binding sites in the immunoglobulin molecule. By contrast, a bispecific antibody is a single immunoglobulin molecule that has two different specificities. It can be made by fusion of two monoclonal antibody producing hybridoma cell lines, where each hybridoma has a different antigen specificity, and selection for a cell line (a quadroma) that produces an antibody whose composition is a tetramer composed of one light chain and one heavy chain from each hybridoma fusion partner. The antibody produced by the quadroma has only one light and one heavy chain of each parental specificity and has one binding site for each heavy/light chain pair and is bispecific, i.e., it has two binding sites of different specificities. A bispecific antibody can also be made by genetic engineering. It can comprise the $V_L$-linker-$V_H$ of one antibody linked through an additional linker to a $V_L$-linker-$V_H$ of another antibody molecule. The order of $V_L$ and $V_H$ can be altered, but the end result is a bispecific antibody.

Epitope: Depending on the size, structure and conformation of the antigen, an antibody may bind only to a small part of the entire structure. The part of the antigen molecule to which the antibody binds is called its epitope. Different antibodies may be mapped to different epitopes on the same antigen.

Neoepitope: The antigen may have an epitope which is hidden so that it cannot bind to a specific antibody. However, a conformational change in the antigen may cause the appearance of the epitope by unfolding or uncovering part of the surface of the molecule. This now allows the antibody to bind to the epitbpe. In another aspect, the action of an enzyme on the antigen may cause the appearance of a new epitope to which the antibody can bind. For example, after cleavage by a proteolytic enzyme, new N-terminal and new C-terminal sequences are generated. Because the epitope is not observed in the parent molecule and because, after some change in the parent molecule, the epitope is revealed and now can bind antibody, it is called a neoepitope.

TuINE: Abbreviation for the phrase "type II collagen neoepitope", this term is used to refer to the specific collagen neoepitope recognized by the 9A4 antibody.

Biological media: This may be defined as any biological fluid that might contain the antigen and be of interest to assay by this procedure. These include: blood, syhovial fluid, urine, feces, sperm, saliva, spinal fluid, bronchiolar lavage fluid, lymph, the vitreous humor of the eye, extracts of tissues, tissue culture supernatants, extracts of cartilage, etc. Biological media need not be limited to human samples, but may also be obtained from a similar variety of animal media (mouse, rat, hamster, guinea pig, dog, and bovine have been tested) in a fashion similar to the examples above.

Immunoassay: An assay for a substance (complex biological such as a protein or a simple chemical) based on using the binding properties of antibody to recognize the substance which may be a specific molecule or set of homologous molecules. The assay may involve one or more antibodies.

Direct assay: The antibody binds directly to an antigen such as in a biological specimen (cells, tissues, histological section, etc.) or to antigen adsorbed or chemically coupled to a solid surface. The antibody itself is usually labeled to enable the determination of the amount of antibody bound to the antigen. Alternatively, the antibody (now termed primary antibody) is detected with a secondary labeled antibody that will demonstrate that binding of the primary antibody had occurred.

Competitive assay: An assay based on the binding properties of a single antibody molecule. Typically, a labeled antigen is used to compete with an unknown antigen and the amount of unknown antigen is determined in terms of how much of the labeled antigen is displaced by the unknown antigen. The label may be radioactive, optical, enzymatic, fluorescent polarizing, fluorescent quenching, or other label. The antibody may be monospecific or bispecific.

Sandwich assay: This is a double antibody assay in which both antibodies bind to the antigen, forming a trimeric immune complex or sandwich containing the two antibodies with the antigen between them. One antibody is utilized to localize the immune complex to the detection surface or chamber. This antibody is termed the capture antibody. The other antibody bears a label that will allow the immune complex to be detected. It is called the detection antibody. If an immune complex is not formed (no antigen is present), then the capture antibody is unable to bring the detection antibody to the detector. If antigen is present, then an immune complex will form and the capture antibody will be joined with the detection antibody such that the amount of detection antibody in the immune complex is quantitatively related to the amount of antigen present.

The assay can be formatted in many ways. For example, the capture antibody can be chemically coupled to a solid surface, or non-specifically adsorbed to a surface, attached via biotinylation to an avidin-like molecule (e.g., avidin, streptavidin, neutravidin, etc.) or avidin-coated surface, or coupled to magnetic particles or beads, each as a means of localizing the immune complex to the measurement device.

The detection antibody may be radiolabeled, or it may have a variety of possible enzymatic amplification systems such as horse radish peroxidase (HRP), alkaline phosphatase (AP), urease, etc., when formatted as an ELISA (Enzyme-Linked ImmunoSorbent Assay). It may use an electrochemical, optical, fluorescent, or other detection method to determine the amount of detection antibody in the immune complexes.

It may immediately be seen that many examples can be derived in which the two antibodies are paired in a sandwich assay using a variety of methods to capture the immune complex in a detection device and a variety of detection systems to measure the amount of immune complex.

Molecular biology techniques: Because the nucleotide sequences of $V_L$- and $V_H$-encoding regions are now provided for the antibodies of the present invention, a skilled artisan could in vitro produce a complete gene coding for the $V_H$ and $V_L$ regions and a completely functional antibody. It can be produced as an immunoglobulin molecule of any given class with constant regions of the heavy chain and light chain added or it can be produced as a scFv with $V_L$ and $V_H$ joined by a linker with tags added as appropriate; The constructed gene may be engineered by conventional recombinant techniques, for example, to provide a gene insert in a plasmid capable of expression. Thereafter, the plasmids may be expressed in host cells where the host cells may be bacteria such as *E. coli* or a Bacillus species, yeast cells such as *Pichia pastoris*, or in mammalian cell lines such as Sp2/0, Ag8, or CHO cells.

Homology: Throughout the present application, whenever reference is made to amino acid or nucleic acid homology, BLASTP, BLASTN, and FASTA (Atschul et al., *J. Mol. Biol.*, 215:403–10 (1990)) have been used to calculate homology, unless otherwise specified. The BLAST X program is publicly available from NCBI and other sources (BLAST Manual, Altschul et al., NCBI NLM NIH Bethesda, Md. 20894; and Altschul et al., Id.).

Abbreviations

Nucleic acids, amino acids, peptides, protective groups, active groups and similar moieties, when abbreviated are abbreviated according to the IUPACIUB (Commission on Biological Nomenclature) or the practice in the fields concerned. The following are examples.

| Standard Abbreviations | |
|---|---|
| HPLC | High pressure liquid chromatography |
| SDS-PAGE | Sodium dodecyl sulfate polyacrylamide gel electrophoresis |
| PCR | Polymerase chain reaction |
| Oligo | Oligonucleotide |
| RT | Room temperature, circa 22° C. |

-continued

Standard Abbreviations

Reagents:

| | |
|---|---|
| EDTA | Ethylenediamine tetraacetic acid |
| SDS | Sodium dodecyl sulfate |
| TW-20 | Tween-20 |
| NFDM | Non-fat dry milk |
| DPBS | Dulbecco's phosphate buffered saline |
| Bt | Biotinylated |
| HAT | Hypoxanthine, aminopterin, thymidine containing media |
| HT | Hypoxanthine, thymidine containing media |
| HRP | Horseradish peroxidase |

Immunoglobulin-like molecules or chains

| | |
|---|---|
| $V_H$ or VH | Variable region of the heavy chain |
| $V_L$ or VL | Variable region of the light chain |
| scFv | Single chain antibody containing a $V_L$ and $V_H$ |

Nucleic Acids

| | |
|---|---|
| RNA | Ribonucleic acid |
| DNA | Deoxyribonucleic acid |
| cDNA | Complimentary DNA |
| mRNA | Messenger RNA |

Nucleic acid bases

| Purines | Pyrimidines |
|---|---|
| A: Adenine | T: Thymine |
| G: Guanine | C: Cytosine |
| | U: Uracil |

Amino Acids-Single letter codes: Three letter codes: Full names.

| | | |
|---|---|---|
| G: Gly: glycine | V: Val: valine | L: Leu: leucine |
| A: Ala: alanine | I: Ile: isoleucine | S: Ser: serine |
| D: Asp: aspartic acid | K: Lys: lysine | R: Arg: arginine |
| H: His: histidine | F: Phe: phenylalanine | Y: Tyr: tyrosine |
| T: Thr: threonine | C: Cys: cysteine | M: Met: methionine |
| E: Glu: glutamic acid | W: Trp: tryptophan | P: Pro: proline |
| O: Hyp: hydroxyproline | N: Asn: asparagine | Q: Gln: glutamine |

EXAMPLES

Example 1

Generation and Characterization of Monoclonal Antibody 9A4

Balb/c mice (Jackson Laboratories, Bar Harbor, Me.) were immunized initially with the peptide having the sequence set forth in the Sequence Listing as SEQ ID NO: 17 (Anaspec, San Jose, Calif.) covalently linked to the KLH maleimide (Pierce Chemical, Rockford, Ill.) and administered in complete Freund's adjuvant (DIFCO Detroit, Mich.). The mice were boosted monthly for about 5 months using incomplete Freund's adjuvant (DIFCO, Detroit, Mich.) until the titers were 1:100,000. Mice were boosted i.v. 10 days prior to fusion. Splenocytes were collected and fused with a non-Ig secreting cell-line derived from P3X63Ag8.653 (American Type Culture Collection, Bethesda, Md.) using 50% PEG-1450 (ATCC). They were plated at $10^6$ cells/well in 96 well microtiter plates in HAT media (Sigma, St. Louis, Mo.) with 15% fetal calf serum (Hyclone, Provo, Utah). Ten days later the wells were screened by a primary ELISA. For identification of positive antibody producing wells, 10 ng/ml biotinylated peptide (Bt-AEGPPGPQG) [biotinylated on residue 1 of SEQ ID NO: 14] was added to streptavidin (10 μg/ml) coated plates (Pierce Chemical) and 2 μl of each hybridoma supernatant added to 100 μl of DPBS (Gibco, Grand Island, N.Y.) with 0.05% TW-20 (Sigma). ELISA positive wells were detected by rabbit anti-mouse IgG-HRP (Jackson Immuno Research, West Grove, Pa.).

Positive wells in the ELISA were subjected to a second round of selection on the BIAcore™ system. Wells were sought that produced antibodies having slow off rates on the BIAcore™ system as determined using BIAevaluation™ version 2.1 software (Pharmacia Biosensor, Piscataway, N.J.). Streptavidin (Pierce Chemical) at 100 μg/ml was conjugated using the Pharmacia Amine Coupling Kit (Pharmacia Biosensor) to carboxylated dextran-coated biosensor chips (Pharmacia Biosensor) at a pH 4.0 using a flow rate of 5 μl/minute for 35 minutes. Typically, 2000 RU was added. Peptide (100 ng/ml) biotinylated on residue of 1 of SEQ ID NO: 14 as set forth in the Sequence Listing, was passed over the streptavidin chip at a flow rate of 100 μl/minute for 10 seconds. Candidate supernatants containing antibody were passed over the chip (2 μl/minute for 30 seconds) and the amount of added antibody noted. The buffer was changed to HBS (HEPES buffered saline, Pharmacia Biosensor), and the dissociation rate noted for the next 80 seconds. The chip was cleaned with 0.1 N HCl for 30 seconds between each run to remove residual antibody and to clear any nonspecific binding. The off-rates were determined using BIAevaluation™ kinetic analysis software version 2.1. Clones with the slowest off rates were selected for further analysis. These clones included 9A4, 11F2, and 3H10.

Further characterization of these clones was performed as follows: Four preparations consisting of type I collagen, type I collagen cleaved by collagenase, type II collagen, and type II collagen cleaved by collagenase were each coupled to a separate flow cell on a BIA 2000 instrument. They were conjugated using the Pharmacia Amine Coupling Kit (Pharmacia Biosensor) to carboxylated dextran coated biosensor chips (Pharmacia Biosensor) at pH 4.0 using a flow rate of 5 μl/minute for 35 minutes. The four flow cells added 8000, 7000, 4000, and 4000 RU, respectively. The cells were washed with 0.1 N HCl to clean them of any uncoupled material and to clean them of any residual antibody between runs. All antibody preparations were purified by Protein G chromatography (Pharmacia Biotechnology, Piscataway, N.J.) and were run at 10 μg/ml. The total binding to each of the four surfaces was recorded. Antibody 9A4 was selected because it showed selective binding to collagenase-cleaved type II collagen (type I=11 RU; type II=280 RU) and lacked significant binding to uncleaved collagen (type I=3 RU; type II=6 RU).

After three rounds of subcloning by limiting dilution in HT media (Sigma) with 5% fetal calf serum (Hyclone), a stable 9A4 monoclonal hybridoma was obtained. It has been deposited with the American Type Culture Collection as ATCC-HB-12436.

Example 2

Generation and Characterization of Monoclonal Antibody 5109

Balb/c mice were immunized initially with the peptide having the sequence set forth in the Sequence Listing as SEQ ID NO: 18 (Anaspec, San Jose, Calif.) covalently linked to the KLH maleimide (Pierce Chemical) and administered in complete Freund's adjuvant (DIFCO). The mice were boosted monthly for about 5 months using incomplete Freund's adjuvant (DIFCO) until the titers were 1:100,000. Mice were boosted i.v. 10 days prior to fusion. Splenocytes were collected and fused with a non-Ig secreting cell-line derived from P3X63Ag8.653 cells (ATCC) using 50% PEG-1450 (ATCC). They were plated at $10^6$ cells/well in 96 well microtiter plates in HAT media (Sigma) with 15% fetal calf serum (Hyclone). Ten days later the wells were screened by ELISA. For identification of positive antibody producing wells, 10 ng/ml biotinylated peptide (biotinylated on residue 1 of SEQ ID NO: 19 as set forth in the Sequence Listing) was added to streptavidin (10 µg/ml) coated plates (Pierce Chemical) and 2 µl of each hybridoma supernatant added to 100 µl of DPBS with 0.05% TW-20 (Sigma). ELISA positive wells were detected by rabbit anti-mouse IgG-HRP (Jackson ImmunoResearch).

Positive wells were subjected to a second round of selection on the BlAcore™ system for those which had antibodies giving the slowest off-rates. Streptavidin (Pierce Chemical) at 100 µg/ml was conjugated using the Pharmacia Amine Coupling Kit (Pharmacia Biosensor) to carboxylated dextran coated biosensor chips (Pharmacia Biosensor) at pH 4.0 using a flow rate of 5 µl/minute for 35 minutes. Typically, 2000 RU was added. Peptide (100 ng/ml), biotinylated on residue 1 of SEQ ID NO: 19 as set forth in the Sequence Listing, was passed over the streptavidin chip at a flow rate of 100 µl/minute for 10 seconds. Supernatants containing antibody were passed over the chip (2 µl/minute for 30 seconds) and the amount of added antibody noted. The buffer was changed to HBS (Pharmacia Biosensor), and the dissociation rate noted for the next 80 seconds. The chip was cleaned with 0.1 N HCl for 30 seconds between each run to remove antibody and to get rid of any nonspecific binding. The off-rates were determined using the BlAevaluation™ software version 2.1. Clones with slow off-rates were sought. mAb 5109 was selected for further analysis.

Four preparations consisting of type I collagen, type I collagen cleaved by collagenase, type II collagen, and type II collagen cleaved by collagenase were each coupled to a single channel of a four channel BlAcore ™ system. These were conjugated using the Pharmacia Amine Coupling Kit (Pharmacia Biosensor) to carboxylated dextran coated biosensor chips (Pharmacia Biosensor) at pH 4.0 using a flow rate of 5 µl/minute for 35 minutes. The four flow cells added 8000, 7000, 4000, and 4000 RU, respectively. The cells were washed with 0.1 N HCl to clear them of any uncoupled material and to clear them of any specific materials between runs. All antibody preparations were purified by Protein G chromatography (Pharmacia Biotech), and run at 10 µg/ml. The total binding to each of the four surfaces was recorded. Antibody 5109 was selected because it showed selective binding to collagenase cleaved collagen (cleaved type I=23 RU; cleaved type II=173 RU), but lacked significant binding to uncleaved collagen (type I=23 RU; type II=15 RU). After nine rounds of subcloning by limiting dilution in HT media (Sigma) with 5% fetal calf serum (Hyclone), a stable 5109 monoclonal hybridoma was obtained. It has been deposited with the American type culture collection as ATCC-HB-12435.

Example 3

Description of a Sandwich Assay Using 9A4 as the Capture Antibody and Monoclonal 5109 as the Detection Antibody Monoclonal antibody 9A4 (the capture antibody) was added to Nunc Maxisorp™ (VWR, Boston, Mass.) 96-well plates with 9A4 at 10 µg/ml in 0.05 M sodium borate buffer, pH 8.5 using 100 µl/well (except for control wells numbered 4, 5, and 6, see Table 1) and incubated for 18–48 hours at 4° C.

The plate was washed three times with DPBS containing 0.05% TW-20 (Sigma), (DPBS/TW-20); 200 µl/well was used.

Wells in the plate were blocked with 1% non-fat dry milk (NFDM) dissolved in DPBS (NFDM DPBS) prepared freshly, i.e., held on ice for no more than the day of use, using 100 µl/well incubated for 1 hour at RT.

The blocking solution was discarded, the wells rinsed one time with 200µl of DPBS/TW-20.

Peptide 130 was diluted in 0.1% NFDM DPBS to concentrations shown in Table 1. Peptide 130 has the sequence set forth in the Sequence Listing as SEQ ID NO: 20 and was synthesized and purified by Anaspec Inc (San Jose, Calif.).

The dilutions of peptide 130 (SEQ ID NO: 20), the specimens at appropriate dilutions, and the controls were placed into the specified wells of the microtiter plate as shown in Table 1.

TABLE 1

Outline of the microtiter plate and antibody coating scheme
Note that table 1

| | pep130 (SEQ ID NO: 20) ng/ml | | | | | | | | | | | |
|---|---|---|---|---|---|---|---|---|---|---|---|---|
| pep 130 | 2 | 1.33 | 0.889 | 0.59 | 0.4 | 0.26 | 0.18 | 0.12 | 0.08 | 0.05 | 0.03 | 0.02 |
| | " | " | " | " | " | " | " | " | " | " | " | " |
| | smpl | smpl | smpl | smpl | smpl | smpl | smpl | smpl | smpl | smpl | smpl | smpl |
| | " | " | " | " | " | " | " | " | " | " | " | " |
| | " | " | " | " | " | " | " | " | " | " | " | " |
| | " | " | " | " | " | " | " | " | " | " | " | " |
| cntrls. | 1 | 1 | 2 | 2 | 3 | 3 | 4 | 4 | 5 | 5 | 6 | 6 |

TABLE 2

| | Additions to the control wells | | | |
|---|---|---|---|---|
| Controls: | | Biotinylated | Anti-biotin antibody |
| | 9A4 | 130 | 5109 | HRP-labeled |
| 1 | + | − | − | + |
| 2 | + | + | − | + |
| 3 | + | − | + | + |
| 4 | − | + | + | + |
| 5 | − | + | − | + |
| 6 | − | − | + | + |

The wells were washed three times with 200 µl/well of DPBS TW-20.

Biotin-conjugated mAb 5109 (Bt-5109) was added to all peptide 130 (SEQ ID NO: 20) containing wells, all sample wells, and all control wells except 1,2, and 5. Bt-100 µl/well) at 1 µg/ml in 0.1% NFDM DPBS was added to each well and the ncubated for 40 min at 37° C.

Note: mAb 5109 was biotinylated using 37 μg of biotin-N-hydroxysuccinamide (Pierce Chemical) per mg of mAb 5109 for 2 hrs and then dialyzed overnight using a 10 kD cut-off dialysis cassette (Pierce Chemical).

The wells were washed three times with 200 μl/well of DPBS/TW-20.

Mouse monoclonal anti-biotin antibody conjugated with HRP (Jackson ImmunoResearch) was diluted 1/5000 in 0.1% NFDM DPBS and 100 μl/well was added to all wells and incubated for 30 minutes at RT.

The wells were washed three times with 200 μl/well of DPBS/TW-20.

100 μl/well of 1-step Turbo (ready to use 3,3',5,5'-tetramethylbenzidine; Pierce Chemical) was added to each well and incubated at RT for approximately 10 minutes. Color development was stopped with 2N $H_2SO_4$. The results were read on a spectrophotometer at 450 nm.

TABLE 3

Standard curve data for 9A4 capture/Bt-5109 detection sandwich assay

| E311 | pep 130 (SEQ ID NO: 20) ng/ml | nM | log nM | OD450 | lin regr | lin regression slope | intercept |
|---|---|---|---|---|---|---|---|
| 1 | 10 | 5.88 | 0.769 | 0.78 | | 0.029 | 0.024 |
| 2 | 5 | 2.94 | 0.468 | 0.74 | | | |
| 3 | 2.5 | 1.47 | 0.167 | 0.698 | | | |
| 4 | 1.25 | 0.735 | −0.134 | 0.623 | 0.618 | | |
| 5 | 0.625 | 0.368 | −0.435 | 0.483 | 0.474 | | |
| 6 | 0.313 | 0.184 | −0.736 | 0.326 | 0.331 | | |
| 7 | 0.156 | 0.092 | −1.037 | 0.151 | 0.187 | | |
| 8 | 0.078 | 0.046 | −1.338 | 0.072 | 0.044 | | |
| 9 | 0.039 | 0.023 | −1.639 | 0.039 | | | |
| 10 | 0.020 | 0.011 | −1.94 | 0.005 | | | |
| 11 | 0.010 | 0.006 | −2.241 | −5E−04 | | | |
| 12 | 0 | 0 | | −0.006 | | | |

From the concentrations of peptide 130 and the resulting optical density reading at 450 nm (Table 3), a standard curve was constructed (FIG. 1). Other appropriate peptides or collagen fragments can be substituted to prepare a standard curve analogous to FIG. 1. The units were expressed in terms of molar equivalents of standard. In this case, the units were nM equivalents of peptide 130 (SEQ ID NO: 20).

Over the linear portion of the curve, a regression line was used to fit the data. In the given case, the standard curve was linear between 0.735 nM and 0.46 nM when the concentrations are given in the log scale (as in the example, FIG. 1) and the regression curve is obtained using just the linear portion of the curve. For samples that fall outside of the linear portion, the concentrations can be read off the graph or the samples may be diluted to fall within the standard portion of the curve, or they may be below the limit of detection.

The regression between log (nM) and OD450 gives a slope of 0.029 OD450/log(nM) and an intercept of 0.024 OD450. When unknown samples are run, the calibration curve can be used to determine of concentration of collagenase-generated type II collagen fragments from the optical density of the sample. The following equation can be used:

Log(Concentration)=(Sample OD450−Intercept)/Slope

Sample:

In the given case, an unknown sample of synovial fluid had an OD450 of 0.229. Thus Log(Concentration)=(Sample OD450−0.024)/0.029=−0.949

Taking the anti-log, the concentration of fragment in synovial fluid=0.112 nM.

Example 4

Description of a Sandwich Assay Using Monoclonal Antibody 5109 as the Capture Antibody and 9A4 as the Detection Antibody Monoclonal antibody 5109 (the capture antibody) was added to Nunc Maxisorp™ (VWR, Boston, Mass.) 96-well plates with 5109 at 10 μg/ml in 0.05 M sodium borate buffer, pH 8.5, using 100 μl/well (except for control wells numbered 4, 5, and 6, see Table 4) and incubated for 18–48 hours at 4° C.

The plate was washed three times with 200 μl/well of DPBS/TW-20.

Wells in the plate were blocked with 100 μl/well of freshly prepared 1% NFDM dissolved in DPBS and incubated for 1 hour at room temperature.

The blocking solution was discarded, and the wells rinsed one time with 200 μl of DPBS/TW-20.

Peptide 130 (SEQ ID NO: 20) was diluted in 0.1% NFDM DPBS to concentrations shown in Table 4. The dilutions of peptide 130 (SEQ ID NO: 20), the unknown specimens at appropriate dilutions, and the controls were placed into the specified wells of the microtiter plate as shown in Table 4.

TABLE 4

Outline of the microtiter plate and antibody coating scheme

| | | pep130 (SEQ ID NO: 20) (ng/ml) | | | | | | | | | | |
|---|---|---|---|---|---|---|---|---|---|---|---|---|
| pep 130 | 2 | 1.33 | 0.889 | 0.59 | 0.4 | 0.26 | 0.18 | 0.12 | 0.08 | 0.05 | 0.03 | 0.02 |
| | " | " | " | " | " | " | " | " | " | " | " | " |
| | smpl | smpl | smpl | smpl | smpl | smpl | smpl | smpl | smpl | smpl | smpl | smpl |
| | " | " | " | " | " | " | " | " | " | " | " | " |
| | " | " | " | " | " | " | " | " | " | " | " | " |
| | " | " | " | " | " | " | " | " | " | " | " | " |
| | " | " | " | " | " | " | " | " | " | " | " | " |
| cntrls. | 1 | 1 | 2 | 2 | 3 | 3 | 4 | 4 | 5 | 5 | 6 | 6 |

TABLE 5

Additions to the control wells

| Controls | | Biotinylated | Anti-biotin antibody |
|---|---|---|---|
| 5109 | 130 | 9A4 | HRP-labeled |
| 1 | + | − | − | + |
| 2 | + | + | − | + |
| 3 | + | − | + | + |
| 4 | − | + | + | + |
| 5 | − | + | − | + |
| 6 | − | − | + | + |

The wells were washed three times with 200 μl/well of DPBS/TW-20.

Biotin conjugated monoclonal antibody 9A4 (Bt-9A4) was added to all peptide 130 (SEQ ID NO: 20) containing wells, all sample wells, and all control wells except 1, 2, and 5. 100 μl/well of Bt-9A4 at 1 μg/ml in 0.1% NFDM DPBS was added to each well and the plate incubated for 40 min at 37° C.

Note: 9A4 was biotinylated using 37 μg of biotin-N-hydroxysuccinamide (Pierce Chemical) per mg of monoclonal antibody 9A4 for 2 hrs and then dialyzed ON using a 10 kD cut-off dialysis cassette (Pierce Chemical).

The wells were washed three times with 200 μl/well of DPBS/TW-20.

Mouse monoclonal anti-biotin antibody conjugated with HRP (Jackson ImmunoResearch) was diluted 1/5000 in 0.1% NFDM DPBS and 100 μl/well was added to all wells and incubated for 30 minutes at RT.

The wells were washed three times with 200 μl/well of DPBS/TW-20.

One hundred microliters/well of 1-step Turbo™ (ready to use 3,3',5,5'-tetramethylbenzidine; Pierce Chemical) was added to each well and incubated at RT for approximately 10 minutes. Color development was stopped with 2N $H_2SO_4$. The results were read with a spectrophotometer at 450 nm.

TABLE 6

Standard curve data for 5109 capture/Bt-9A4 detection sandwich assay

| | pep 130 (SEQ ID NO: 20) | | log | lin | lin regression | |
|---|---|---|---|---|---|---|
| Cln | ng/ml | nM | nM | OD450 | regr slope | intercept |
| 1 | 10 | 5.88 | 0.769 | 0.64 | 0.42 | 0.70 |
| 2 | 5 | 2.94 | 0.468 | 0.65 | | |
| 3 | 2.5 | 1.47 | 0.167 | 0.62 | | |
| 4 | 1.25 | 0.735 | −0.134 | 0.61 | | |
| 5 | 0.625 | 0.368 | −0.435 | 0.57 | | |
| 6 | 0.313 | 0.184 | −0.736 | 0.52 | 0.52 | |
| 7 | 0.156 | 0.092 | −1.037 | 0.40 | 0.39 | |
| 8 | 0.078 | 0.046 | −1.338 | 0.23 | 0.26 | |
| 9 | 0.039 | 0.023 | −1.639 | 0.11 | 0.13 | |
| 10 | 0.020 | 0.011 | −1.94 | 0.04 | 0 | |
| 11 | 0.010 | 0.006 | −2.241 | 0.01 | | |
| 12 | 0 | 0 | | −0.01 | | |

From the concentrations of peptide 130 (SEQ ID NO: 20) and the resulting optical density reading at 450 nm, a standard curve was constructed. Again, other appropriate peptides or collagen fragments could be utilized to prepare a standard curve. The units needed were expressed in terms of equivalents of standard. In this case, the units were appropriate in terms of nM equivalents of peptide 130 (SEQ ID No: 20).

Over the linear portion of the curve, a regression line was used to fit the data. In given case, the standard curve was linear between 0.3125 nM and 0.0195 nM when the concentrations were given in the log scale (as in the example Figure) and the regression curve was obtained using just the linear portion of the curve. For samples that fall outside of the linear portion, the concentrations can be read off the gragh or the samples may be diluted to fall within the standard portion of the curve, or the concentration of collagen fragments in the samples may be below the detection limit.

The regression between log (nM) and OD450 nm gives a slope of 0.42 OD450/log(nM) and an intercept of 0.70 OD450 nm. When samples are run, the calibration curve can be used to determine the concentration of collagen fragment from the optical density of the sample.

Samples:

In the given case, the unknown sample of human urine from an arthritic patient has an OD450 of 0.124.

Log(Concentration)=(Sample OD450−0.70)/0.42=−1.36

Taking the anti-log, the concentration of fragment in urine= 0.44 nM.

In another case, the standard curve gave a slope of 0.249 and an intercept of 0.638. An unknown sample of human osteoarthritis plasma had an OD450 nm of 0.172. The sample of osteoarthritic plasma had a fragment concentration of 68 pM.

Example 5

Antibody 5109 can be used Directly to Measure the Amounts of Type II Collagen Fragment in a Competition Assay In an adaptation of concentration analysis (BIAapplications Handbook, Pharmacia Biosensor, June, 1994 Edition, p. 6–2 to 6–9), streptavidin (Pierce Chemical, Rockford, Ill.) at 100 μg/ml was conjugated with the Pharmacia Amine Coupling Kit (Pharmacia Biosensor) to carboxylated dextran coated biosensor chips (Pharmacia Biosensor) at pH 4.0 using a flow rate of 5 μl/minute for 35 minutes. Typically, 2000 RU was added. Biotinylated peptide (100 ng/ml) having the sequence set forth in the Sequence Listing as SEQ ID NO: 19 was passed over the streptavidin chip at a flow rate of 5 μl/minute for 2 minutes; 144 RU of peptide was added to the streptavidin surface. mAb 5109 at a concentration of 6.3 μg/ml either alone or in mixtures with standard concentrations of peptide 054 (SEQ ID NO: 19) or mixtures of 5109 and dilutions of samples with unknown amounts of collagen fragments were passed over the peptide surface for 1 minute at a flow rate of 10 μl/min. The slopes of the linear portions of the association phase for each curve were analyzed with BIAevaluation™ version 2.1 software. A standard curve of competing peptide 054 (SEQ ID NO: 19) vs. slope was constructed. The amount of collagen epitope in the samples was determined by comparison of a sample's slope to the slopes of the standard curve to calculate the amount of epitope. Between each injection, the chip was cleaned with 0.1 N HCl for 30 seconds to remove antibody.

TABLE 7

5109 mixed with standard amounts of peptide 054 (SEQ ID NO: 19).

| | Dil. of pep054 M | log M | r0 slope | linear regression values |
|---|---|---|---|---|
| 1 | 1.34E−06 | −5.87 | 0.187 | |
| 2 | 6.71E−07 | −6.17 | 0.208 | |
| 3 | 3.36E−07 | −6.47 | 0.375 | |
| 4 | 1.68E−07 | −6.78 | 0.729 | 2.16 |
| 5 | 8.39E−08 | −7.08 | 12.7 | 10.09 |
| 6 | 4.19E−08 | −7.38 | 17.1 | 18.03 |
| 7 | 2.10E−08 | −7.68 | 25.7 | 25.96 |
| 8 | 1.05E−08 | −7.98 | 22.5 | |
| 9 | 5.24E−09 | −8.28 | 26.6 | |
| 10 | 2.62E−09 | −8.58 | 24.0 | |
| 11 | 1.31E−09 | −8.88 | 26.6 | |
| 12 | 6.55E−10 | −9.18 | 25.6 | |
| 13 | 0 | | 23 | |

Linear regression slope = −26.36
y-intercept = −176

Sample:

Supernatant of a collagenase-3 MMP-13 digest of bovine nasal cartilage. The sample was run over the BlAcore™ chip diluted 2-fold, 4-fold, and 8-fold. The calculated amounts of collagen in terms of 054 peptide (SEQ ID NO: 19) were determined. The results are given in the fourth column of Table 8. After multiplying by the titer, a molar concentration (M) of collagen can be determined in terms of the peptide 054 (SEQ ID NO:19) standard.

TABLE 8

The titer and concentrations of the unknown sample in terms of peptide 054 (SEQ ID NO: 19) concentration.

| | titer | slope | M (054) | nM (054) |
|---|---|---|---|---|
| 5109 | alone | 6.648 | Background | |
| 5109 + | 1:2 | 3.539 | 4E−08 | 80 |
| 5109 + | 1:4 | 4.885 | 2E−08 | 80 |
| 5109 + | 1:8 | 5.825 | 8E−09 | 64 |

The consistency of the results (last column) after correction for dilution is shown by the agreement of the values calculated from the three separate dilutions (next to last column) of the unknown samples. An average value of 75 nM type II collagen fragments is obtained for the bovine nasal cartilage supernatant.

Example 6

Preparation of Genetically Engineered Antibodies Related to 9A4

The basis for generating engineered antibodies and their subsequent evaluation as biologically active or relevant molecules is the cloning (with assembly into the proper configuration) and characterization of the $V_L$ and $V_H$ domains of the parent antibody. We have determined the $V_L$ and $V_H$ structural sequences of the subject antibodies and the uniqueness of the particular $V_L$-$V_H$ combination that forms the active binding site to the antigens described in this invention. Before cloning the 9A4 variable region genes, it was necessary to determine the protein sequence of portions of the variable domains of the parent 9A4 IgG1 antibody so that when the variable domains were cloned, it could be ascertained that the correct variable domains were indeed obtained and not other ones derived from the myeloma fusion partner or an inactive pseudogene from the B-cell used in generating the hybridoma. Culture supernatant containing 9A4 IgG1 was generated by growing the 9A4 hybridoma in roller bottles. Supernatants were adjusted to pH 7.5 with dibasic sodium phosphate and the salt concentration adjusted with 3 M sodium chloride to a final concentration of 150 mM. Filtered (0.2μ) supernatant was passed through a 15 ml bed volume of Protein G (Pharmacia) at a flow rate of 20 ml/min. After further washing the column with 150 mM NaCl solution, the antibody was eluted with 100 mM glycine pH 3.1. The antibody was isotyped using anti-sera from the Mouse Immunoglobulin Isotyping Kit (Boehringer Mannheim, Indianapolis, Ind.) and found to be an IgG1 class murine antibody with a kappa light chain.

It has been observed that some isolated proteins are "blocked" at their amino terminus. By "blocked" it is meant that the amino acid residue at the amino terminus of the polypeptide chain has been chemically modified in its structure post-translationally by cellular action or some spontaneous chemical change in such a way that the polypeptide chain is resistant to Edman degradation. The Edman degradation method is the chemical procedure routinely used over the past 40 years for determining the amino acid sequence of proteins. Use of the Edman degradation technique, normally automated in a laboratory instrument known as a sequenator or protein sequencer, is a standard procedure well known to those skilled in the art of protein biochemistry.

A common mode of blocking is conversion of an amino-terminal glutaminyl residue into a pyroglutamyl residue. This occurs by cyclization of the glutaminyl residue to form a structure that is inaccessible to the Edman reaction because a new amide linkage is formed between the former alpha-amino group and the delta-carboxyl group. In such circumstances, the ability to obtain sequence information from the amino terminus of the protein depends on removal of the pyroglutamyl residue by a chemical or enzymatic method. An important method is to use an enzyme called pyroglutamate aminopeptidase (EC 3.4.19.3) to remove the pyroglutamyl residue. The blocked protein, which may be in solution or electroblotted to a membrane material such as PVDF (polyvinylidene difluoride), is treated with a solution of pyroglutamate aminopeptidase until a sufficient amount of the protein has been unblocked to allow successful determination of the amino acid sequence by automated Edman chemistry. Example methods for this are described in Fowler et al., "Removal of N-Terminal Blocking Groups from Proteins" in Current Protocols in Protein Science., pp.11.7.1–11.7.17 (Eds. Coligan et al.), John Wiley, New York (1995).

In the present work, the heavy and light chains of mAb 9A4 were separated by SDS-polyacrylamide gel electrophoresis with the use of a reducing agent (beta-mercaptoethanol) in the sample buffer. Following electrophoresis, polypeptides in the gel were electroblotted to a PVDF membrane and detected by staining with Coomassie Brilliant Blue R-250. Bands containing the heavy and light chains of 9A4 were then excised from the blot and separately treated with pyroglutamate aminopeptidase. In each case, it proved possible subsequent to this treatment to obtain amino-terminal sequence information by Edman degradation. Sequencing was performed on a Perkin-Elmer Applied Biosystems Model 494 Procise™ protein sequencer.

When it is desired to obtain internal (i.e., not N-terminal) amino acid sequence information from the protein, blotted samples of the protein may be digested with trypsin and the resulting digest fractionated by HPLC to afford individual peptides which may then be sequenced.

Specifics of the work were as follows.

N-terminal De-blocking With Pyroglutamate Aminopeptidase (PGAP)

Antibody (9A4) was separated into its constituent heavy and light chains by SDS-PAGE on a Tris-Gly 4–20% polyacrylamide gel (Novex, San Diego). It was then electroblotted onto ProBlott™ (Perkin-Elmer Applied Biosystems, Foster City, Calif.) and the bands were visualized by Ponceau S (Sigma) staining.

The membranes containing 9A4 light chain were excised and incubated for 30 min in a buffer containing 0.1 M sodium phosphate, 10 mM $Na_2EDTA$, 5 mM dithioerythritol, 5% glycerol, and 0.1% reduced Triton X-100. Pyroglutamate aminopeptidase (20 mg)(Boehringer Mannheim, Indianapolis, Ind.) was added to the vial, the contents mixed gently, and the reaction was incubated overnight at 37° C. The membranes were removed and washed extensively in water to remove all salts, detergent and enzyme. The membranes were then placed in the fied Trypsin (0.2 mg)(Promega, Madison, Wis.) was added and the bands were incubated overnight at 37° C. The resulting peptides were extracted from the membrane by washing (with 60% acetonitrile and 0.1% TFA in $H_2O$) and sonication. The peptides were separated by reverse phase-HPLC on a Vydac C18 218TP column (1.0×250 cm)(Vydac, Hesperia, Calif.). The peaks were collected visually by hand and selected peaks were analyzed by automated Edman sequencing on a Model 494 protein sequencer as above.

TABLE 10

N-terminal sequence results for 9A4 peptide fragment protein sequencing.

| Sequence data file | Sequence | |
|---|---|---|
| 9A4L_10 | DSTYSMSSTL | ($C_K$ sequence) |
| 9A4L_12 | LLIHATSNLASGVPVR | (Note 1) |
| 9A4L_13 | FSGGGSGTSYSLTISR | (Note 2) |
| 9A4L_14 | XFNR | ($C_K$ sequence) |
| 9A4L_15 | (H)NSYTCEATHK | ($C_K$ sequence) |
| 9A4L_16 | (Q)NGVLNGTSY | ($C_K$ sequence) |
| 9A4L_17 | LEIIR | (Note 3) |

Residues in parenthesis indicate tentative calls.
Note 1: This sequence corresponds to residues 52 to 67 of SEQ ID NO: 33.
Note 2: This sequence corresponds to residues 68 to 83 of SEQ ID NO: 33.
Note 3: This sequence corresponds to residues 110 to 114 of SEQ ID NO: 33.

The mature 9A4 light chain ($V_L$-$C_{kappa}$) amino acid sequence is as follows.

```
  1 QIVLTQSPVF MSASPGEKVT MTCSASSSVS YMYWYQQKPG SSPRLLIHAT SNLASGVPVR

61 FSGGGSGTSY SLTISRMEAE DAATYYCQQW RSYTRTFGGG TKLEII*RADA APTVSIFPPS

121 SEQLTSGGAS VVCFLNNFYP KDINVKWKID GSERQNGVLN SWTDQDSKDS TYSMSSTLTL

181 TKDEYERHNS YTCEATHKTS TSPIVKSFNR NEC
```

Applied Biosystems Model 494 protein sequencer (Perkin-Elmer) for N-terminal sequence analysis according to the directions provided by the manufacturer.

The heavy chain was treated in the same manner as above.

TABLE 9

N-terminal sequence results of 9A4 protein sequencing.

| Sample | Sequence data file | Sequence |
|---|---|---|
| Light chain | 9A4L_7 3-22-96 | IVLTQSPVFMSASPGEKVTM (Note 1) |
| Heavy chain | 9A4H_4 3-26-96 | IQLVQSGPELKKPGQTVKI(S) (Note 2) |

Residues in parenthesis indicate tentative calls.
Note 1: This sequence corresponds to residues 9 to 28 of SEQ ID NO: 33.
Note 2: This sequence corresponds to residues 13 to 32 of SEQ ID NO: 32.

In addition to the N-terminal sequence data obtained above, internal sequencing of the 9A4 antibody light chain was also performed, according to the method developed from Fernandez et al., *Anal. Biochem.*, 218:112–17 (1994).

Four bands corresponding to the 9A4 light chain were excised from the ProBlottm and incubated for 30 min in a buffer containing 10% acetonitrile, and 0.1% reduced Triton X-100 in 0.1 M Tris-HCl pH 8.8. Sequencing Grade Modi- Underlined amino acids have been sequenced by automated Edman sequencing (Also see table 9 above). The sequence obtained from the cloned DNA, when compared with the amino acid sequences from the fragments of the original antibody protein shown above, indicates that the gene cloned is the correct one for the 9A4 $V_L$ (comparison of sequence derived from DNA sequencing of the cloned $V_L$ (see below) and the murine $C_{kappa}$ (obtained from Kabat et al., "Sequences of Proteins of Immunological Interest, U.S. Department of Health and Human Services, NIH, 5th Edition, publication # 91-3242, 1991) with sequences obtained by Edman degradation).

Amino acid 106 above is usually a Lys residue in the J1 germline segment, but has been mutated to the Ile residue shown above for the 9A4 $V_L$. Amino acid 106 marks the end of the $V_L$ domain while amino acid 107 (Arg) marks the beginning of the $C_{kappa}$ domain.

Cloning and Determination of the $V_L$ and $V_H$ Sequences of mAb 9A4

The 9A4 hybridoma cell line was grown in HT media (Sigma) with 5% fetal calf serum (Hyclone). mRNA was extracted from a cell pellet containing $1 \times 10^7$ cells using the Pharmacia Quick Prep™ mRNA Extraction Kit (Pharmacia) as per the manufacturer's protocol. cDNA was then synthesized for both the $V_L$ and $V_H$ gene segments using Boehringer Mannheim's cDNA Kit (Indianapolis, Ind.) as per the protocol provided by the manufacturer. The oligo used in the $V_L$ cDNA reaction (named MLK) and set forth in the Sequence Listing as SEQ ID NO: 21 was specific for the murine light chain kappa region, while the oligo used in the $V_H$ cDNA reaction (named MHG) is specific for a segment in the $C_H2$ domain of the murine heavy chain gamma region. The sequence of MHG is set forth in the Sequence Listing as SEQ ID NO: 22. This oligo was designed to anneal to all 4 murine IgG isotypes, including IgG1, IgG2a, IgG2b and IgG3. There is a single base mismatch for IgG1 at nucleotide 5 of SEQ ID NO: 22, but it should be apparent to those skilled in the art that this would not prevent annealing and subsequent generation of cDNA. The oligos were synthesized by Oligos Etc. (Wilsonville, Oreg.), Genosys (The Woodlands, Tex.), or Perkin-Elmer Applied Biosystems (Foster City, Calif.).

The amino terminal amino acid sequence data was used to generate a possible oligo to isolate the correct 9A4 $V_H$ gene by PCR as follows. Based on the 20 amino acid sequence presented above for the $V_H$ amino terminal region, which corresponds to residues 13 to 32 of SEQ ID NO: 32, and assuming that the amino terminal amino acid of the mature form of the secreted antibody heavy chain was indeed a Gln residue (residue 12 of SEQ. ID. NO. 32), sequences of known antibodies were compared to that of 9A4 $V_H$ using the Kabat data base from Sequences of Proteins of Immunological Interest, Volume II, 1991. Antibody $V_H$ domains that matched the first 20 amino acids of the mature 9A4 $V_H$ included: mAb 264 (Nottenburg et al., *J. Immunol.*, 139:1718–1726 (1987)); MAbRFT2 (Heinrich et al., *J. Immunol.*, 143:3589–3597 (1989)); and MAb2H1 (Li et al., *Mol. Immunol.*, 27:303–311 (1990)). Since it is important to obtain the original DNA sequence corresponding to the amino terminus of the mature antibody, the 5' PCR oligo should be designed to anneal 5' (upstream) from the amino terminus, i.e., in the signal peptide segment. The DNA sequences of all the above 3 antibodies, with which the first 20 amino acids of the 9A4 $V_H$ was identical, had known signal peptide DNA and amino acid sequences. The DNA sequences are shown here: (Underlined nucleotides indicate differences between the sequences).

```
                                                (SEQ ID NO: 23)
    264:      5'-GG CTG TGG AAC TTG CTA TTC (SEQ ID NO: 24)
    RFT2:     5'-GG GTG TGG ACC TTG CCA TTC (SEQ ID NO: 25)
    2H1:      5'-GG GTG TGG ACC TTG CTA TTC
```

These sequences code for amino acids −11 to −17 in the signal peptides for the $V_H$s of the corresponding antibodies (see Kabat et al., supra). The chosen 5' oligo, named MHMISC, was thus designed to isolate the genuine 9A4 $V_H$. The sequence of MHMISC is set forth in the Sequence Listing as SEQ ID NO: 26.

For isolating the 9A4 $V_L$, a series of five degenerate oligo sets were designed to anneal to the leader peptide segments of known murine kappa light chains. These oligos were employed in 5 separate PCR amplifications (See below). The sequences of the 5 degenerate oligo sets were provided by The Dow Chemical Company (Midland Mich.) and are hereby acknowledged. The 5' oligo set that gave a bona fide 9A4 $V_L$ was MK3, the sequence of which is set forth in the Sequence Listing as SEQ ID NO: 27. These oligos code for residues −8 to −14 in the signal peptide.

The reverse primers for the $V_L$ and $V_H$ PCRs were designed from known sequences of the murine IgG1 heavy chain constant region (from the $C_H1$ domain), called MIGGICH1, the sequence of which is set forth in the Sequence Listing as SEQ ID NO: 28, and the constant region of the kappa light chain, called MLKN, the sequence of which is set forth in the Sequence Listing as SEQ ID NO: 29. These oligos were nested (upstream) relative to the 3' primers used in the cDNA synthesis.

The annealing segment begins at nucleotide 10 of SEQ ID NO: 29.

The 9A4 $V_H$ and $V_L$ genes were amplified by PCR using the corresponding oligos described above and 1 ng of 9A4 hybridoma cDNA. The PCR was set up using a GeneAmp® Kit with Native Taq Polymerase (Perkin Elmer) according to the manufacturer's specifications. The temperatures of denaturation, annealing, and polymerization were 94° C., 55° C., and 72° C. for 45, 45, and 60 seconds, respectively. For the $V_H$ PCR and for the $V_L$ PCR the annealing temperature was changed to 60° C. The PCR was carried out for 36 cycles plus a final polymerization cycle of 72° C. for 7 min followed by a 4° C. hold. The PCR products were sequenced to determine and verify the DNA and derived amino acid sequences of the $V_L$ and $V_H$. The oligos used for sequence determination were MK3 and MLKN for the $V_L$ and MIGG1CH1 for the $V_H$ and are set forth in the Sequence Listing as SEQ ID NOS: 27, 29, and 28, respectively.

The DNA sequences corresponding to 9A4 $V_H$ and $V_L$ are set forth in the Sequence Listing as SEQ ID NOS: 5 and 6, respectively. The derived amino acid sequences of the 9A4 $V_H$ and $V_L$ genes are set forth separately in the Sequence Listing as SEQ ID NOS: 32 and 33, respectively.

Surprisingly, the oligo MHMISC (SEQ ID NO: 26) successfully provided a $V_H$ sequence which corresponded exactly to the first 20 amino acids of the mature protein $V_H$ determined by protein sequencing of 9A4 IgG1. Immediately 3' of the 5' PCR oligo, MHMISC (SEQ ID NO: 26), the DNA sequence in the leader peptide segment of the 9A4 $V_H$ is almost identical to the corresponding segment of mAb 2H1, and is likely therefore to be derived from the same germlne $V_H$ gene as 2H1. There are only 3 differences in amino acid sequence between the 2 antibodies in the $V_H$ regions; 1 in CDR1, 1 in CDR2, and 1 in FR3. These are likely somatic mutations that have occurred during the affinity maturation process for these two antibodies and may play a role in defining the specificity and affinity of each of the antibodies for their respective targets. The 9A4 $V_H$ utilizes the murine $J_H2$ joining segment gene and codes for residues 114 (within the CDR3) to 126 of SEQ ID NO: 32.

The 9A4 variable heavy chain belongs to Kabat's Mouse Ig heavy chain Family II (The $V_H$ genes here identified were taken from the Kabat Database at http:H/immuno.bme.nwu.edu/famgroup.html). The 9A4 $V_H$ heavy chain (SEQ ID NO: 5) most closely resembles Database ID number 001246. There are only 2 differences in these 2 $V_H$ genes, one occurring in the FR1 (silent mutation), and the other in the CDR1 at amino acid position 45 (SEQ ID NO: 32) where 9A4 has an Ile and 001246 has a Met. It is most likely that both of these genes are also derived from the same germlne $V_H$.

The methods of the present invention also can be performed using $V_H$ genes in other antibodies related to the 9A4 $V_H$ germine gene, such that when the $V_H$ gene product forms a productive antibody $V_L$-$V_H$ pair with the $V_L$ of this other antibody, it binds in a manner (specificity and affinity) analogous to 9A4.

The 9A4 $V_L$ gene and derived amino acid sequences are set forth in the Sequence Listing as SEQ ID NOS: 6 and 33, respectively. The derived amino acid sequence of the 9A4 $V_L$ gene matches all the peptide fragments from protein sequencing of genuine 9A4 light chain as presented above. The 9A4 variable light chain belongs to Kabat's Mouse Kappa Family XI and is most similar to Database ID Number 006306. There are 10 nucleotide mismatches, resulting in 7 amino acid differences. Two of these differences occur in FR1, 2 in CDR2, 1 in FR3, and 2 in CDR3. Since the majority of the changes occur in the CDRs, it is most likely that these 2 genes are related by being derived from the same or at least very similar germlne $V_L$.

The methods of the present invention also can be performed using $V_L$ genes in other antibodies derived or related to the 9A4 $V_L$ germlne gene, such that when the $V_L$ gene product forms a productive antibody $V_L$-$V_H$ pair with the $V_H$ of this other antibody, it binds in a manner (specificity and affinity) analogous to 9A4.

The methods of the present invention also can be performed using antibodies where both the $V_L$ and $V_H$ are derived from the 9A4 $V_L$ and $V_H$ germlne genes, disclosed herein, such that when the $V_L$ and $V_H$ gene products form a productive $V_L$-$V_H$ pair, this other or different antibody from 9A4 essentially binds in a manner (specificity and affinity) analogous to 9A4.

We now have the basis from which to design and construct genetically engineered versions of the subject invention 9A4 antibody. Two examples are presented below, both single chain antibodies (scFv). In one case, the design is $V_H$-Linker-$V_L$-HIS-MYC tags in the vector pCANTAB6 and in the other the scFv is constructed in the opposite orientation with a different linker, that is, $V_L$-Linker-$V_H$-FLAG tag, in the vector pATDFLAG. These examples are not meant to be limiting, but to those skilled in the art, it will readily be apparent that the newly characterized $V_H$ and $V_L$ domains of 9A4 (SEQ ID NOS: 5 and 6) can be utilized in part or in whole to obtain previously described antibody types, such as Fab's, or novel configurations that utilize only some critical portion of the V domains.

Construction of 9A4 scFv ($V_H$-linker-$V_L$) in pCANTAB6

SOEing (Splicing by Overlap Extension) PCR primers were utilized to prepare for assembly of the $V_H$ and $V_L$ fragments into a scFv antibody.

Two primers were designed and obtained from Perkin Elmer for the $V_H$ region: for the 5' $V_H$ end primer an Sfi I site was added while at the 3' end for the $V_H$ primer, an overlapping sequence with the (Gly$_4$Ser)$_3$ linker was added. The 5' $V_H$ primer was called 9A4VH5CAN and the 3' $V_H$ primer was called 9A4H3CAN, which correspond to SEQ ID NOS: 34 and 35 in the Sequence Listing.

For the $V_L$, a 5' end primer with overlap into the Gly$_4$Ser linker region and a 3' primer incorporating a Not I restriction site were designed and also obtained from Perkin Elmer. The 5' primer was called 9A4VL5CAN and the 3' $V_L$ primer was called 9A4VL3CANILE, which correspond to SEQ ID NOS: 36 and 37 in the Sequence Listing.

The $V_H$ and $V_L$ DNA components were amplified by PCR and joined subsequently by an assembly, pull-through SOE-PCR step. Following the SOE-PCR reaction, a band in an agarose gel, which was identified to be ~700 bp, was excised and gel purified using the QIAquick™ Gel Purification Kit (QIAgen) as per the manufacturer's directions. The resulting DNA was digested with Sfi I and Not I and used in a ligation with the pCANTAB6 vector DNA (obtained from Cambridge Antibody Technology, Melbourne, Cambridgeshire, UK) which was also digested with the same restriction enzymes. The ligated DNA was then used to transform competent E. coli TG1 cells by electroporation. The basic protocol for generating the competent E. coli TG1 cells was as follows.

500 ml 2YT media (Bio101, La Jolla, Calif.) prewarmed to 37° C. in a 2 liter conical flask was inoculated with 2.5 ml of fresh overnight culture of TG1 cells. The cells were grown with vigorous aeration (300 rpm) at 37° C. until the OD at 600 nm was 0.2 to 0.25, usually 1–1.5 h later. The flasks were chilled for 30 min on ice, then poured into 250 ml centrifuge bottles and spun at 4,000 rpm for 15 min in a prechilled (4° C.) Sorvall centrifuge to pellet the cells. The cells were resuspended in the original volume of prechilled water, and spun again as above to pellet the cells.

The cells were resuspended in half the original volume, i.e., 250 ml, of prechilled water and left on ice for 3 min, then resuspended and spun again as above.

The cells were then resuspended in 20 ml of prechilled 10% glycerol, transferred to a prechilled 50 ml Falcon tube, left on ice for 15 min, and centrifuged at 3,500 rpm at 4° C. for 10 min in a benchtop centrifuge.

The cells were finally resuspended in 1.0–2.5 ml prechilled 10% glycerol and used directly in the electroporation step.

Ligated DNA (25–250 ng pCANTAB6-Sfi I/Not I vector with 9A4 $V_H$-L-$V_L$-Sfi I/Not I) was electroporated into the competent E. coli TG1 cells as follows.

The ligated DNA was ethanol precipitated per standard protocol. The DNA pellet was dissolved in 10 µl of sterile deionized distilled water. The DNA (up to 10% of the total cell volume) was added to 100 µl of cells and transferred to a prechilled electroporation cuvette (Biorad) and left on ice.

The electroporation Gene Pulser™ apparatus (Biorad) parameters were set to 25 µFD, 2.5 kV, and the pulse controller set to 200 ohms. The cuvette was dried with a tissue, placed in the electroporation chamber and pulsed once. Time constants in the 3.5–4.8 msec range were typically obtained. The electroporated cells were immediately diluted with 1 ml of 2YT medium supplemented with 2% glucose. The cells were transferred to a 15 ml Falcon tube and shaken at 37° C. for 1 h.

The transformed cell mixture (20–1000 µl) was plated on appropriate size agar media plates containing 2YT, 2% glucose, and 100 µg/ml ampicillin (2YTAG).

Initially, a clone was obtained (p9A4lCAT3-2) that had a 5 base insertion at the Not I site, which put the downstream sequence out-of-frame. In order to correct this, a new oligo was made called 9A4NOTFIX3, the sequence of which is set forth in the Sequence Listing as SEQ ID NO: 38.

A PCR amplification using E. coli cells containing p9A4lCAT3-2 as the target for the annealing oligos was performed using the Advantage KlenTaq™ Polymerase Mix (Clontech, Palo Alto, Calif.) as per the manufacturer's protocol. The annealing oligos (35 pmol each) were 9A4NOTFIX3 and pUC19R. The sequence of pUC19R is set forth in the Sequence Listing as SEQ ID No. 39; it anneals upstream from the Sfi I site.

The PCR cycles (in a Perkin Elmer Cetus Model 9600 thermal cycler) were set up as follows: For the first cycle, denaturation of DNA was for 1 min at 94° C., annealing for 45 s at 60° C. and polymerization for 1.5 min at 68° C. For cycles 2–31, the same temperatures and times were used, except the denaturation times were reduced to 30 sec. For the final cycle (32) the polymerization was set up for 5 min, after which time the cycler cooled the sample to 4° C. The TA cloning system. (Invitrogen) was used to clone the resulting PCR products in the plasmid pCR2.1 using the protocol suggested by the manufacturer. Twelve white colonies were screened for inserts using the oligos M13 Forward and M13 Reverse (Invitrogen) (as set forth in the Sequence Listing as SEQ. ID. NOS. 53 and 54, respectively) by PCR using KlenTaq™ Polymerase as above. Three colonies produced inserts of the correct size on agarose gel electrophoresis. One of these with the correct DNA sequence for the 9A4 and $V_H$-Linker-$V_L$ construct was chosen for further work. The DNA insert containing the scFv gene was obtained by digestion of the pCR2.1 derivative with Sfi I and Not I, purified using the QlAquick™ Gel Extraction kit and ligated with the pCANTAB6 vector digested with the same restriction enzymes. The DNA was electroporated into competent *E. coli* TG1 cells as described above and resulted in a clone named p9A4lCAT7-1 (ATCC 98593) which contained an active scFv. The DNA sequence of this 9A4 scFv is set forth in the Sequence Listing as SEQ ID NO: 7, while the amino acid sequence is set forth separately as SEQ ID NO: 40. Note that the GTG codon, beginning at position 29 of SEQ ID NO: 7 is the start codon (Met). The sequencing oligos used were pUC19R and FDTETSEQ which are set forth in the Sequence Listing as SEQ ID NOS: 39 and 41, respectively.

See the information for SEQ ID NOS: 7 and 40 in the Sequence Listing for specific features of the DNA and amino acid sequences for this scFv antibody.

The genetically engineered 9A4 $V_H$-Linker-$V_L$ format scFv antibody was expressed in *E. coli* TG1 cells, and the antibody was purified using NTA-Ni agarose (QlAgen) affinity chromatography, followed by Superdex 75 gel filtration chromatography to isolate monomer scFv species. The binding to the parental antigen of the scFv was evaluated on the BlAcore™ system (see below). *E. coli* containing the plasmid pA4lCAT7-1 has been deposited with the American Type Culture Collection as ATCC 98593.

Construction of 9A4 scFv ($V_L$-linker-$V_H$) in pATDFLAG

SOEing oligos were also prepared for PCR-SOE assembly of the $V_H$ and $V_L$ fragments in the opposite configuration, i.e., $V_L$-linker-$V_H$, relative to the example presented above involving p9A4lCAT7-1. Two primers were designed for the $V_L$-linker region: at the 5' end an Nco I site was added and at the 3' end, an overlapping sequence with the 25 amino acid linker sequence set forth in the Sequence Listing as SEQ ID NO: 42 (Pantoliano et al., *Biochemistry*, 30:10117–25 (1991)) was added. The 5' $V_L$ primer was named 9A4VL5ATD and the 3' $V_L$ primer was named 9A4VL3ATDILE. The sequences of these oligos are set forth in the Sequence Listing as SEQ ID NOS: 43 and 44, respectively.

For the $V_H$, a 5' end primer with overlap into the linker region and a 3' end PCR primer with an added Nhe I site was designed. The 5' $V_H$ primer was named 9A4VH5ATD and the 3' $V_H$ primer was named 9A4VH3ATD. The sequences of these oligos are set forth in the Sequence Listing as SEQ ID NOS: 45 and 46, respectively.

The $V_L$ and $V_H$ components were amplified by PCR. The $V_L$ and $V_H$ were then joined in the linker region by SOE-PCR using the oligos 9A4VL5ATD (SEQ ID NO: 44) and 9A4VH3ATD (SEQ ID NO: 46). DNA at the correct size, about 700 bp, was excised out from a 1% agarose gel and eluted using the QlAquick™ gel elution kit. The resulting DNA was trimmed at the ends with the restriction enzymes Nco I at the 5' end and Nhe I at the 3' end. This was ligated with the expression vector pATDFLAG (PCT WO 93/12231) treated with the same restriction enzymes. Competent *E. coli* DH5a cells were transformed with the ligation as per the manufacturer's protocol and plated on agar plates containing 20 µg/ml of chloramphenicol as the selective agent. Two of the clones that were sequenced, p9A4lF-5 and p9A4lF-69, had no PCR or construction errors. The sequencing oligos were: UNIVLSEQ-5' (SEQ ID NO: 30) and TERMSEQ(-) (SEQ ID NO: 31).

*E. coli* containing p9A4lF-5 was chosen for further work and expression of the engineered 9A4 scFv antibody. The DNA sequence of this scFv is set forth in the Sequence Listing as SEQ ID NO: 8, while the derived amino acid sequence is set forth separately as SEQ ID NO: 47. Specific features of the $V_L$-L-$V_H$-FLAG 9A4 scFv, such as signal peptide, linker, and tag locations are indicated in the Sequence Listing for SEQ ID NOS: 8 and 47. It will be obvious to those skilled in the art that the engineered antibody described could be expressed not just from *E. coli*, but from other organisms as well, including, but not limited to, *P. pastoris*, Baculovirus, Bacillus species, mammalian cells, and the like.

For expression and purification of this, scFv product from *E. coli*, 1–2, liter cultures of LB broth containing 20 µg/ml of chloramphenicol were grown overnight at 37° C. Cells were pelleted in a Sorvall centrifuge using a GS-3 rotor. In preparation for affinity chromatography using an M2 affinity column (Kodak, New Haven, Conn.) (which is specific for the FLAG epitope shown in the sequence above) the pelleted *E. coli* cells were processed either in a Tris/EDTA/sucrose media to isolate the periplasmic fraction or were sonicated (Soniprep sonicator) directly in a minimal volume of DPBS buffer. The affinity column was washed extensively with DPBS to remove any unbound materials after loading the crude scFv sample. The scFv antibody was eluted using 0.1 M glycine-HCl pH 3.1. The monomer scFv species was isolated by Superdex-75 gel filtration chromatography (Pharmacia). The antibody was judged to be homogeneous by SDS-PAGE and staining with Coomassie Brilliant Blue R-250. Antibody was quantitated spectrophotometrically at OD 280 nm, where an absorbance of 1.4 was defined to be equivalent to 1.0 mg/ml scFv, using a 1.0 cm pathlength quartz cuvette. *E. coli* containing the plasmid p9A4lF-5 was deposited with the American Type Culture Collection as ATCC-98592.

Binding to antigen was evaluated on the BlAcore™ system for both the p9A4lCAT7-1 and p9A4lF-5 scFv purified gene products as follows. A streptavidin chip was loaded with biotinylated peptide of SEQ ID NO: 14 as given in Example 1 above. Both scFv constructs were shown to bind antigen, i.e., compared to the parent 9A4 IgG which binds with a K of $1.2 \times 10^{-7}$ M, the 9A4lF-5 scFv has a K of $1.1 \times 10^{-7}$ M. For the 9A4lCAT7-1 scFv, the off-rate was $1.2 \times 10^{-3}$/sec compared to $1.76 \times 10^{-2}$/sec for 9A4 IgG (parent antibody). These data indicate that the affinity of the engineered antibodies were at least as good or better than the parent.

As evidenced by the specificity and kinetic data determined by the BlAcore™ system, the 2 engineered antibodies containing the 9A4 $V_L$ and $V_H$ domains described above have the desired characteristics for using them in the quantitative measurement assays described in Examples 3 and 4 above. Other engineered antibodies comprised of some or all of the 9A4 $V_L$ and $V_H$ disclosed herein having the affinity and specificity of the parent 9A4 antibody, would therefore be considered to be useful in the methods of the present invention.

Example 7

Preparation of the Genetically Engineered Antibodies Related to 5109

Before cloning the 5109 variable region genes, it was necessary to determine the protein sequence of portions of the variable domains of the parent 5109 antibody so that when the variable domains were cloned, it could be ascertained that the correct variable domains were indeed obtained and not other ones derived from the myeloma fusion partner or an inactive pseudogene from the B cell used in generating the hybridoma. Culture supernatant containing 5109 was generated by growing the 5109 hybridoma in roller bottles. Supernatants were adjusted to pH 7.5 with dibasic sodium phosphate and the salt concentration adjusted with 3 M sodium chloride to a final concentration of 150 mM. Filtered (0.2μ) supernatant was passed through a 15 ml bed volume of Protein G (Pharmacia) at a flow rate of 20 ml/min. After further washing the column with 150 mM NaCl solution, the antibody was eluted with 100 mM glycine pH 3.1. The antibody was isotyped using anti-sera from the Mouse Immunoglobulin Isotyping Kit (Boehringer Mannheim) and found to be an IgG1 class murine antibody with a kappa light chain constant domain.

In the present work, the heavy and light chains of mAb 5109 were separated by SDS-PAGE with the use of a reducing agent (beta-mercaptoethanol) in the sample buffer. Following electrophoresis, polypeptides in the gel were electroblotted to a PVDF membrane and detected by staining with Coomassie Brilliant Blue R-250. Bands containing the heavy and light chains of 5109 were then excised and subjected to Edman degradation. Sequencing was performed on a Perkin-Elmer Applied Biosystems Model 494 Procise™ protein sequencer as per the manufacturer's protocols. The sequences of the heavy and light chains that were obtained are shown in Table 11, and correspond to residues 1 to 40 of SEQ ID NO: 48 for the $V_H$ and to residues 1 to 39 of SEQ ID NO: 49 for the $V_L$.

TABLE 11

Results of N-terminal amino acid sequence of 5109.

| Res # | Heavy chain | Res # | Light chain |
|---|---|---|---|
| 1 | E | 1 | D |
| 2 | V | 2 | V |
| 3 | Q | 3 | V |
| 4 | L | 4 | M |
| 5 | V | 5 | T |
| 6 | E | 6 | Q |
| 7 | S | 7 | T |
| 8 | G | 8 | P |
| 9 | G | 9 | L |
| 10 | G | 10 | T |
| 11 | S | 11 | L |
| 12 | V | 12 | S |
| 13 | Q | 13 | V |
| 14 | P | 14 | T |
| 15 | G | 15 | I |
| 16 | G | 16 | G |
| 17 | S | 17 | Q |
| 18 | L | 18 | S |
| 19 | K | 19 | A |
| 20 | L | 20 | S |

TABLE 11-continued

Results of N-terminal amino acid sequence of 5109.

| Res # | Heavy chain | Res # | Light chain |
|---|---|---|---|
| 21 | S | 21 | I |
| 22 |   | 22 |   |
| 23 | A | 23 |   |
| 24 | A | 24 | K |
| 25 | S | 25 | S |
| 26 | G | 26 | S |
| 27 | F | 27 | Q |
| 28 | T | 28 |   |
| 29 | F | 29 | L |
| 30 | N | 30 | L |
| 31 | T | 31 | G |
| 32 | Y | 32 | (S) |
| 33 | G | 33 | D |
| 34 | M | 34 | (G) |
| 35 | S | 35 | L |
| 36 | W | 36 | T |
| 37 | V | 37 | Y |
| 38 | R | 38 | (L) |
| 39 | Q | 39 |   |
| 40 | T | 40 |   |

Tentative amino acids are indicated by ( ).
Note:
Position 22 in the $V_H$ and position 23 of the $V_L$ is normally Cys, and cannot be determined by Edman degradation.

Cloning and Determination of the $V_L$ and $V_H$ Sequences of mAb 5109

The 5109 hybridoma cell line was grown in HT media (Sigma) with 5% fetal calf serum (Hyclone). Cells were pelleted ($2.5 \times 10^7$ cells/pellet) and frozen at −80° C. until use. Extraction of mRNA (Oligotex™ Direct mRNA Kit; QIAGEN) was carried out according to the manufacturer's directions. cDNA was then synthesized for the $V_L$ and $V_H$ regions using Boehringer Mannheim's First-Strand cDNA Synthesis Kit. The oligo used in the $V_L$ cDNA reaction was specific for the murine light chain kappa region (MLK) while the oligo used in the $V_H$ cDNA reaction, MHG, was specific for a segment in the murine heavy chain $C_H2$ gamma region. The sequences of oligos MLK and MHG are set forth in the Sequence Listing as SEQ ID NOS: 21 and 22, respectively.

PCR primers were designed for the N-terminal sequence of the mature, secreted forms of the heavy and light chains based on the amino acid sequences that were obtained for the $V_L$ and $V_H$ by Edman degradation. The sequences were compared with the Kabat database; the 5109 $V_H$ was found to be most similar to members of Kabat subgroup IIID, while the 5109 $V_L$ was most similar to members of Kabat subgroup II.

The sequences of the 5' $V_H$ primer and 5' $V_L$ primer were named 51-09$V_H$5' NDe and 51–09$V_L$5' NDe respectively, and are set forth in the Sequence Listing as SEQ ID NOS: 50and 51.

Reverse primers were designed from known sequences of the IgG1 heavy chain constant region (to a segment in the $C_H1$ domain) and the constant region of the kappa light chain. Both of these 3' oligos are 5' (upstream) of the original oligos used to generate the cDNA. The 3' $V_H$ primer (named MIGG1CH1) and the 3' $V_L$ primer (named MULK2) are set forth in the Sequence Listing as SEQ ID NOS: 28 and 52, respectively.

The resulting PCR products for the $V_L$ and $V_H$ were ligated into pCR2.1 and representative clones were chosen for subsequent DNA sequencing. DNA sequencihg was performed on an Applied Biosystems Model 373 Stretch Sequencer and was set up and operated according to the protocols provided by the vendor. For DNA sequence determination, the Invitrogen commercial sequencing oligos M13F and M13R were used, the sequences of which are set forth in the Sequence Listing as SEQ ID NOS: 53 and 54, respectively.

The first 21 amino acids that were determined by Edman degradation for the 5109 $V_L$ and $V_H$ mature amino termini were found to be identical to the corresponding amino acid sequences derived from-the DNA sequence of the corresponding genes that were cloned by PCR.

The DNA sequences of the 5109 $V_H$ and $V_L$ domains are set forth in the Sequence Listing as SEQ ID NOS: 10 and 11, respectively. The amino acid sequences of the 5109 $V_H$ and $V_L$ are set forth separately in the Sequence Listing as SEQ ID NOS: 48 and 49, respectively. It should be noted that while the DNA, as presented, codes for the correct amino acids in the amino terminal segments of each of the $V_L$ and $V_H$ segments corresponding to the PCR annealing oligos, the exact codons for the antibody amino acid segments corresponding to these oligos, as they would have occurred in the original hybridoma DNA are not unequivocal. The 5109 $V_H$ utilized the $J_H3$ joining segment gene with 2 mutations in the codon that would otherwise code for a Thr residue (positions 328 and 330 of SEQ ID NO: 10), but in the 5109 $V_H$ is an Ala residue (position 110 of SEQ ID NO: 48).

The 5109 variable heavy chain is most related to Kabat's Mouse Ig heavy chain Family XIV and most closely resembles Database ID number 002754. There are 24 nucleotide differences between these 2 $V_H$ genes, resulting in 14 amino acid differences. It is most likely, based on this high number of differences, that these two genes are not derived from the same germlne gene. It is still possible, however, that the 2 are derived from the same germline and that both have been heavily mutated in the in vivo affinity maturation process and the resulting divergence was amplified.

The methods of the present invention also can be performed using $V_H$ genes in other antibodies related to the 5109 $V_H$ germline gene, such that when the $V_H$ gene product forms a productive antibody $V_L$-$V_H$ pair with the $V_L$ of this other antibody, it binds in a manner (specificity and affinity) analogous to 5109.

The 5109 $V_L$ utilized a J5 joining segment and codes for amino acids 102 to 112 of SEQ ID NO: 49. The CDR3 for this antibody is relatively rare because of the Cys-94 residue contained therein. The CDR3 extends from residues 94 to 102 of SEQ ID NO: 49. When 5109 single chain antibodies were engineered with a 5109 $V_L$ (see below) 2 versions were made, one with the parental Cys-94 and another with Ser substituting for Cys-94.

The 5109 $V_L$ belongs to Kabat's Mouse Kappa Family VI and is most similar to Database ID Numbers 005841, 005842, 005843, and 005844. The 4 antibodies in the database are identical in their nucleotide sequences, so a comparison with the 5109 $V_L$ can be made to all 4 of them at the same time. There are 12 nucleotide mismatches, resulting in 8 amino acid differences. One of these differences occurs in FR1, 3 in CDR1, 1 in FR2, 1 in CDR2, 1 in FR3, and 1 in CDR3. These changes occur throughout the $V_L$, but are focused on the CDRs, with 5 out of the 8 differences being in these hypervariable segments. Therefore it is most likely that these genes are related by being derived from the same or at least very similar germine $V_L$.

The methods of the present invention also can be performed using $V_L$ genes in other antibodies related to the 5109 $V_L$ germline gene, such that when the $V_L$ gene product forms a productive antibody $V_L$-$V_H$ pair with the $V_H$ of this other antibody, it binds in a manner (specificity and affinity) analogous to 5109.

The methods of the present invention also can be performed using antibodies where both the $V_L$ and $V_H$ are derived from the 5109 $V_L$ and $V_H$ germine genes, disclosed in this patent, such that when the $V_L$ and $V_H$ gene products form a productive $V_L$-$V_H$ pair, this other or different antibody from 5109 essentially binds in a manner (specificity and affinity) analogous to 5109.

Construction of 5109 scFv Engineered Antibody ($V_H$-Linker-$V_L$) in pUC19

SOEing PCR primers were utilized to prepare for assembly of the $V_H$ and $V_L$ components. All of the oligos utilized in 5109 scFv construction were synthesized in-house using a Beckman Oligo 1000M DNA synthesizer (Fullerton, Calif.). These five PCR primers, called 5109 VH5', 5109 VH3', 5109 VL5', 5109 VL3' SER and 5109 VL3' CYS are set forth in the Sequence Listing as SEQ ID NOS: 55, 56, 57, 58, and 59 respectively.

The oligo 5109 VL3' Ser (SEQ ID NO: 58) was used to change Cys-94 of SEQ ID NO: 49 to Ser-94 in the scFv construct, (corresponds to the Cys residue at position 248 of SEQ ID NO: 63) to potentially improve the stability of the resulting scFv. Another primer, 5109 VL3' Cys (SEQ ID NO: 59) was also synthesized in order to retain the original Cys sequence.

Following the SOEing reaction, DNA was amplified by PCR and the products either digested with Sfi I and Not I for subsequent ligation into expression vector pUC119 or directly ligated into the sequencing vector pCR2.1. pUC119 ligation products were transformed into DH5a competent cells while pCR2.1 ligations were transformed into InfVα' competent cells. Individual clones were screened via PCR using pUC19R and mycseq10 oligos. DNA from positive clones was submitted for sequencing.

DNA sequence was verified using an Applied Biosystems Model 373 Stretch Sequencing Unit as per the directions of the manufacturer. The following oligos were used for sequencing of potential 5109 scFv engineered antibodies ligated directly into pUC119: pUC19R, MycSeq10, Gly4Ser5', Gly4Ser3', the sequences of which are set forth in the Sequence Listing as SEQ ID NOS: 39, 60, 61, and 62, respectively.

For those 5109 DNA cassettes ligated into the pCR2.1 vector, the M13F and M13R oligos purchased from InVitrogen (SEQ ID NOS: 52 and 53) were utilized for sequence priming reactions, along with SEQ ID NOS: 61 and 62, as two internal oligos.

Clones directly ligated into pUC119 contained a large number of PCR errors. However, an acceptable clone (H55) was identified in the pCR2.1 vector. This construct was then subcloned by digesting the scFv with Sfi I and Not I and ligating into a similarly digested pUC119 vector. Clones were screened for insert by PCR amplification using pUC19R and MycSeq10 oligos (SEQ ID NOS: 39 and 60). Three clones were submitted for sequencing. One clone was identified with the desired sequence and is designated p5109CscFv7 (ATCC 98594); the DNA and derived amino acid sequences are set forth in the Sequence Listing as SEQ ID NOS: 9 and 63, respectively. Sequence features of this engineered antibody are given in SEQ ID NO: 63. In generating the 5109 scFv by PCR, a mutation (PCR error) occurred at nucleotide 738 of SEQ ID NO: 9, changing the amino acid coded for by the altered codon from valine to alanine. This corresponds to the Ala residue at position 237 of SEQ ID NO: 63 (the 5109 scFv sequence). As a conservative difference, it was considered unimportant in terms of affecting the activity of genetically engineered products and was thus allowed to be carried forward in the $V_L$ of the scFv constructs described. Of course, for those skilled in the art, it will be apparent that this PCR error could also be corrected and the original Val residue obtained at this position.

To verify that the new single chain constructs retained the binding properties of the parent molecule, the 5109 scFv was expressed in E. coli and purified.

A 2YT starter culture (50 ml) containing 100 µg/ml ampicillin and 2% glucose was inoculated with 50 µl of –80° C. glycerol stock. Cultures were incubated ON at 30° C. with shaking at 300 rpm. Each of six 2 liter flasks containing 2YT media supplemented with 100 µg/ml ampicillin and 0.1% glucose were inoculated with 5 ml of the overnight starter culture. Cultures were incubated at 30° C. until turbid and subsequently induced by adding IPTG (isopropyl B-D-thiogalactopyranoside; Boehringer Mannheim) to a final concentration of 1 mM. Cultures were grown for an additional 4 hr for production of scFv. Cells were centrifuged at 5000×g for 10 min. Cell pellets were stored at –20° C. until processed.

For scFv purification, cell pellets were resuspended in TES (0.2 M Tris-HCl, 0.5 mM EDTA, 0.5 M sucrose). Following resuspension, a 1:5 dilution of the above TES buffer containing protease inhibitors (Complete Protease Inhibitor Cocktail, Boehringer Mannheim) was added. This preparation was allowed to incubate at 4° C. for 30 min. Following incubation, cells were pelleted at 12,000×g for 15 min. $MgCl_2$ was added to the resulting supernatant to a final concentration of 5 mM. Ni-NTA agarose (QLAgen) was washed 1× in PBS, pH 7.4, containing 300 mM NaCl, 15 mM imidazole, and 0.2% Triton-X. Washed agarose was then added and the slurry was allowed to incubate for 30 min at 4° C. Ni-NTA agarose beads +scFv were then washed 4× as previously described. The scFv was then eluted in wash buffer containing 250 mM imidazole. The eluate was desalted over a NAP-25 column (Pharmacia-Biotech, Uppsala, Sweden) and concentrated using a Centriprep™ concentrator device (Amicon, Beverly, Mass.). Products were electrophoresed on SDS-PAGE and visualized by silver staining. The resulting scFv products for p5109CscFv7 (Cys) and p5109SscFvA9 (Ser) were approximately 15% and 75% pure, respectively.

Using Origen™ methodology (Technical manual, Origen™ Instrument, Igen Corporation, Gaithersburg, Md.), binding to biotinylated peptide 225 (prepared by Anaspec, Inc., and having the sequence set forth in the Sequence Listing as SEQ ID NO: 64) by the 5109 scFv species was measured. Biotinylated peptide 225 was added to 800 µg/ml streptavidin coated magnetic beads (Dynabeads™, Igen, Gaithersburg, Md.) to bring the final concentration to 10 nM and incubated for 15 minutes. The new genetically engineered scFv antibody was added to the peptide/bead solution for 30 min with shaking. The 9E10 anti-myc tag rutheny-lated mAb was added and the solution was incubated for 30 minutes, 200µl Igen assay buffer (Igen, Gaithersburg, Md.) were then added, and the ECL signal was read on the Origen™ Instrument (Igen). mAb 9E10 was generated and purified from the 9E10 cell line, which was obtained from the ATCC. The mAb was ruthenylated using the N-hydroxysuccinamide derivative Origen™ TAG-NHS Ester (Igen) according to the manufacturer's instructions. In the absence of 5109 scFv, a background signal of 2995 ECL units was obtained. Addition of the 5109 scFv Cys construct (p5109CscFv7) resulted in 536,997 ECL units. Addition of the 5109 scFv Ser construct (p5109SscFvA9) resulted in 694,253 ECL units. These results demonstrate that both 5109 scFv genetically engineered antibodies were biologically active and bound to the same collagen-related peptide fragment as mAb 5109 does. A culture of E. coli containing p5109CscFvA9 was deposited with the American Type Culture Collection as ATCC-98594.

The specificity data determined by the Origen™ technology demonstrates that the engineered antibody containing the 5109 $V_L$ and $V_H$ domains described above have the desired characteristics for use in the quantitative measurement assays described in Examples 3 and 4 above. Other engineered antibodies comprised of some or all of the 5109 $V_L$ and $V_H$ disclosed here, having the affinity and specificity of the parent 5109 antibody, would therefore be considered to be useful in practicing the methods of the present invention.

It should also be noted that engineered antibodies comprised of a combination of the 9A4 and 5109 $V_L$ and $V_H$ domains, such as a bispecific scFv dimer of the composition: 5109$V_L$-Linker-5109$V_H$-Linker-9A4$V_L$-Linker-9A4$V_H$-Tag(s) would also be useful, as the only antibody reagent in Examples 3 and 4 above. The difference would be that a single bispecific reagent could be used in a one step ELISA rather than using 9A4 and 5109 separately. To those skilled in the art, it is obvious that a number of genetic compositions comprising the subject antibodies' variable domains could be joined to make a variety of bispecific molecules and thus simplify the assays presented in Examples 3 and 4. The avidity of such molecules could be such that the overall sensitivity of the assay may also be significantly improved.

Example 8

Mutations or differences in amino acid sequences of antibodies can retain the binding properties (affinity and specificity) and therefore the utility of the parent antibody. This is demonstrated below by generating a series of mutants in the CDR3 of the 9A4 $V_H$. To those skilled in the art, it is apparent that other mutations in other regions of the same germlne $V_L$ and $V_H$ genes of both 9A4 and 5109 can give antibodies of the same or of better binding properties relative to the original antibodies disclosed in this invention.

Generation of 9A4 $V_H$ CDR3 Region Mutants

The pCANTAB6 derivative of the 9A4 scFv, namely p9A4lCAT7-1 presented in Example 6 above, was used as the starting material to generate mutants in the CDR3 segment and the Vernier residues immediately adjacent to the CDR3. The parent DNA sequence of the CDR3 $V_H$ region being targeted for mutation comprised nucleotides 383 to 409 of SEQ ID NO: 7. The derived amino acids corresponding to these nucleotides are residues 119 to 127 of SEQ ID NO: 40. The CDR3 begins at residue 121 and ends at 126. To introduce the random mutations in this area, the $V_H$ and $V_L$ regions were amplified separately by 2 PCRs. In the first PCR, oligos (obtained from Oligos Etc.) pUC19R (SEQ ID NO: 39) and 9A4MUT (SEQ ID NO: 65) were used to amplify the $V_H$ portion, where 9A4MUT was the oligo which introduced the mutations.

Nucleotides 25 to 51 in 9A4MUT (SEQ ID NO: 65) were 10% spiked. In other words, the sequence as written accounted for 90% of the nucleotide added at each position 25–51, while the other 3 nucleotides, in each position, 25 through 51, were introduced to the growing oligo chain at 3.3% each. This was accomplished by methods well known in the art of oligonucleotide synthesis. The fact that random nucleotides were indeed introduced in this defined region will be discussed below.

The second PCR utilized the 2 oligos: (also obtained from Oligos Etc.) 9A4L5 (SEQ ID NO: 66) and FDTETSEQ (SEQ ID NO: 41). This produced the Linker-$V_L$ portion up to the Not I site in p9A4lCAT7-1 at the 3' end and with overlap into the $V_H$ at the 5' end that would allow subsequent annealing and assembly with the mutated $V_H$ PCR products from the first PCR.

and electroporation was conducted as described in Example 6. Twelve separate electroporations were performed and ultimately pooled and plated. A total of 1.5×10⁶ clones were obtained and stored as a glycerol stock at −80° C. A random sampling of 12 clones indicated that 9 of them (one clone failed to give sequence data) had an insert when screened by PCR, using the oligos FDTETSEQ (SEQ ID NO: 41) and pUC19R (SEQ ID NO: 39). These inserts were purified using the QlAgen kit and the sequence in the CDR3 $V_H$ determined. The results of the sequencing data are presented below. The DNA sequence of the "Parent Sequence" is set forth in the Sequence Listing as nucleotides 383 to 409 of SEQ ID NO: 7.

| | | Number of Mutations |
|---|---|---|
| Parent sequence: | 5'- GCT AGG GGC GGT AGC CTT GAC TAC TGG -3' | — |
| 9A4MUT-1: | 5'- GCT C̲GG GGC GGT AGC CTT GAC TAC C̲GG -3' | 2 |
| 9A4MUT-3: | 5'- GCT G̲GG C̲C̲C̲ T̲GT AT̲C CTT GAT̲ TAC TGG -3' | 6 |
| 9A4MUT-4: | 5'- GCT AC̲G GGA̲ GGT AGC CTT GAC TAC TGG -3' | 2 |
| 9A4MUT-6: | 5'- GT̲T̲ T̲GG GGC GGC̲ AGC CC̲T GAC C̲AC A̲GG -3' | 6 |
| 9A4MUT-7: | 5'- GCT T̲GG GGC GGC̲ AGG̲ T̲AT̲ GAC TAC TGG -3' | 5 |
| 9A4MUT-8: | 5'- GCT ANG GT̲C A̲GT AGC CTT GAC TCC TGG -3' | 3 |
| 9A4MUT-10: | 5'- GCT AC̲G GGC T̲GT AGT̲ C̲AT GAC TAC C̲G̲C̲ -3' | 6 |
| 9A4MUT-12: | 5'- GCT AGG GGT̲ GGT AGC CTT GAC TAC TGG -3' | 1 |

The PCR was set up as follows. For the mutant $V_H$, 50 pmol of each of the oligos pUC19R (SEQ ID NO: 39) and 9A4MUT (SEQ ID NO: 65) were used in 100 μl reactions. The template DNA target was an aliquot of SNAP (Invitrogen) purified plasmid DNA-p9A4lCAT7-1. Taq Polymerase (Perkin Elmer) was used in the 30 cycle PCR. Denaturation, annealing, and polymerase reaction times and temperatures were 94° C. for 1 min, 55° C. for 1 min, and 72° C. for 2 min, respectively.

For the 30$^{th}$ cycle the polymerization reaction was extended for a total of 10 min, before cooling the reaction to 4° C. For the $V_L$, which would overlap with the $V_H$ species, PCRs were set up using both KlenTaq™ polymerase (Clontech) and Taq Polymerase (Perkin Elmer). DNA products were purified with the QlAgen gel extraction kit. The PCR assembly reaction for the mutated $V_H$ and the $V_L$ was performed using aliquots (1–2 μl) of each of the purified PCR products in a 25 cycle total/2 temperature cycling: 94° C. for 1 min, 65° C. for 4 min, and holding at 4° C. at the end. No oligos were used for this step. For the PCR pull-through of the mutated 9A4 assemblies, 5 μl of unpurified assembly reaction were used as the template and the oligos pUC19R (SEQ ID NO: 39) and FDTETSEQ (SEQ ID NO: 41) as the annealing primers. Correct size products were observed at about 900 bp and were gel purified using the QlAgen gel extraction kit. The mutated 9A4 scFv inserts were treated with Sfi I and Not I to prepare for ligation with the pCANTAB6 vector DNA cut with the same restriction enzymes. After ligation, the DNA mixture was ethanol precipitated and dissolved in 24 μl of sterile deionized distilled water. Preparation of competent *E. coli* TG1 cells The mutations in the cohort above vary in number from 1 to 6 for each clone, and they occur at various positions. The mutations are indicated in bold underline in the various clones above (N=nucleotide could not be assigned). Only 1 clone (9A4MUT-12) out of 8, checked in this random manner, gave parent amino-acid sequence. Based on the randomness of the results shown above, a good mutated library was generated. Therefore, a biotin selection was performed to find binders to peptide 040 (SEQ ID NO: 14) which is the epitope for 9A4.

Description of Biotin Sselection for Antibodies Obtained Below

An aliquot of approximately 100 μl of mutated library stock was added to 25 ml of 2YT media containing 100 μg/ml ampicillin and 2% glucose. The culture was incubated at 37° C. for approximately 60 min or until cells reached mid-log phase (OD$_{600\ nm}$=0.5 to 1.0). M13K07 helper phage (Pharmacia, Uppsala, Sweden) was then added to the culture to a concentration of 5×10⁸ pfu/ml. The helper phage were then allowed to infect the culture for 20 min at 37° C. without shaking and then for another 25 min at 37° C. with shaking at 200 rpm. The infected cells were transferred to a 50 ml conical centrifuge tube and pelleted at 3000 rpm for 10 min. Cells were resuspended in 2YT media containing 100 μg/ml ampicillin and 50 μg/ml kanamycin. This culture was transferred to a fresh 250 ml flask and incubated at 30° C. for 2 h during which time phage particles were produced. Cells were removed by centrifugation at 14,000 rpm for 2 min. Aliquots (1 ml) of phage were then blocked for 30 min at room temperature by the addition of PBS and NFDM to a final concentration of 1×PBS and 3% NFDM. This was accomplished by the addition of 200 μl of a 6×PBS, 18% NFDM solution to 1 ml of phage. Biotinylated peptide 040 (SEQ ID NO: 14) was added to the phage solution at concentrations ranging from 10 pM to 1 μM. This solution was incubated for 60 min at RT. Streptavidin-coated magnetic beads (Dynal, Oslo, Norway) were blocked at RT with end-over-end shaking in 3% NFDM in-PBS. Following incubation, the streptavidin beads were captured at the side of the tube with a magnet and the blocking solution carefully aspirated away. The blocked phage with the bound peptide was then added to the streptavidin beads and allowed to incubate at RT with end-over-end shaking for 15 min. Bead complexes were captured magnetically and unbound phage carefully aspirated away. Magnetic bound bead complexes were washed 4X with PBS containing 0.1% TW-20 and 4× with PBS alone. Following the final capture, bead complexes were resuspended in 100 μl of 100 mM triethylamine in PBS and neutralized with an equal volume of 1 M Tris pH 7.4. Mid-log phase E. coli TG1 cells (10 ml) were then infected with 100 μl of bead complexes. Infection was allowed to progress for 20 min at 37° C. without shaking and then for another 25 min at 37° C. with shaking at 200 rpm. Infected cells were then pelleted, resuspended in 500 μl of fresh 2YT media and 500 μl plated onto 243×243 mm 2YT agar plates containing 100 μg/ml ampicillin and 2% glucose. Plates were incubated overnight at 30° C. Following approximately 16 h of growth, the colonies were recovered by scraping and used to inoculate liquid cultures. The process was repeated for a minimum of two and a maximum of five rounds of selection.

Clones recovered from the biotin selection were grown, induced for production of scFv, which was purified according to the protocol outlined below.

Preparation of scFv Mutant Clones Using Hypotonic Shock Method

The culture were pelleted and resuspended in 0.8 ml ice cold TES buffer (0.2 M Tris-HCl, 0.5 nM EDTA, 0.5 M sucrose). TES (1.2 ml of ice cold 1:5 dilution) was added and the culture was incubated on ice for 30 min. The cells were pelleted at 4° C. at 14,000 rpm (30 min). The scFv supernatant was added to a fresh tube containing 10 μl of 1.0 M $MgCl_2$. NTA-agarose (200 μl) (QlAgen) was prepared by washing in a phosphate imidazole wash buffer containing 50 mM Na phosphate, pH 8.0, 500 mM NaCl, 20 mM imidazole, and 0.1% TW-20. The scFv supernatant was added to the NTA-agarose and incubated at 4° C. for approximately 30 min. The NTA-agarose with scFv was spun and 500 volumes of elution buffer was added. The elution buffer consisted of 50 mM Na phosphate, pH 8.0, 500 mM NaCl, and 250 mM imidazole. The eluate was vortexed and centrifuged to remove the NTA-agarose. The scFv supernatant was buffer exchanged by passing it over a NAP-5 column (Pharmacia), according to the manufacturer's instructions.

Measurement of off-rates for scFv Constructs

Off-rates for the scFv constructs were measured by analysis of dissociation data obtained on the BlAcore™ system (Pharmacia Biosensor) with BlAevaluation™ version 2.1 software. To obtain the data on the BlAcore™ system, streptavidin surfaces on the BlAcore™ chips were prepared as described previously in Example 1. Biotinylated peptide (SEQ ID NO: 14) was bound to the prepared streptavidin surfaces to RU densities ranging from about 2–11 RU's/surface. The lower level of derivatization would help avoid getting erroneous off-rates that could be obtained if mass transport was an issue. Purified scFv's were injected over these surfaces to allow binding of the constructs for 60 seconds. PBS buffer alone was then substituted and the dissociation of scFv was allowed to proceed for an additional 280 sec. Off-rates were calculated from these dissociation data.

TABLE 12

Summary of 9A4 CDR3 $V_H$ Mutant Sequences.
Amino acid sequences determined from the results of DNA sequencing. The parent sequence for clone ICAT7-1 corresponds to residues 118 to 127 of SEQ ID NO: 40.

| Clone | Sequence | | | | | | | | | off-rate × $10^{-2}$ $sec^{-1}$ |
|---|---|---|---|---|---|---|---|---|---|---|
| ICAT7-1 | C | A | R | G | G | S | L | D | Y | W | 0.3 |
| 15A | C | A | R | G | G | R | L | D | Y | W | 0.35 |
| 16A | C | X | R | G | G | S | L | D | L | L | 0.26 |
| 23A | C | G | R | G | R | S | L | D | Y | X | 0.26 |
| 24A | C | G | R | G | G | S | L | E | Y | W | 0.25 |
| 26A | X | X | R | G | X | S | X | E | Y | L | 0.27 |
| 28A | X | X | R | G | G | T | X | E | Y | X | 0.3 |
| 9B | C | X | R | G | G | S | F | E | Y | W | 0.32 |
| 13B | C | X | R | G | G | S | X | D | F | W | 0.26 |
| 14B | C | A | R | G | G | S | L | D | H | W | 0.27 |
| 20B | C | G | R | G | G | N | L | D | H | C | 0.28 |
| 26B | C | G | R | G | X | T | L | E | F | W | 0.34 |
| 31B | C | G | R | G | G | S | L | D | Q | X | 0.26 |
| 37B | C | G | R | G | G | T | L | D | X | X | 0.33 |
| 38B | C | G | R | G | G | S | L | D | S | C | 0.26 |
| 2C | C | G | R | G | S | S | X | D | Y | C | 0.28 |
| 5C | C | A | R | G | G | S | L | D | S | W | 0.25 |
| 9C | C | X | R | G | S | S | L | D | Y | X | 0.99 |
| 10C | C | G | R | G | G | S | L | D | Y | C | 0.94 |
| 20C | C | G | R | X | G | S | X | X | F | C | 1.29 |
| 26C | C | X | R | G | X | S | L | D | I | X | 0.95 |
| 29C | C | G | R | G | G | S | F | X | X | W | 1.04 |

TABLE 12-continued

Summary of 9A4 CDR3 V$_H$ Mutant Sequences.
Amino acid sequences determined from the results of DNA sequencing. The parent
sequence for clone ICAT7-1 corresponds to residues 118 to 127 of SEQ ID NO: 40.

| Clone | Sequence | | | | | | | | | off-rate × 10$^{-2}$ sec$^{-1}$ |
|---|---|---|---|---|---|---|---|---|---|---|
| 8D   | C | A | R | G | G | S | L | D | N | W | 1.04 |
| 16D  | C | X | R | G | G | T | L | D | Y | W | 1.14 |
| 17D  | C | X | X | G | R | S | L | E | X | W | 1.07 |
| 20D  | C | X | R | G | X | T | L | X | Y | W | 1.02 |
| 18E  | C | A | R | G | G | S | L | D | V | W | 1.4 |
| 13G  | C | G | R | G | G | S | L | D | N | W | 1.03 |
| 17G  | C | X | R | G | G | S | L | D | F | W | 1.03 |
| 1H   | C | X | R | G | G | S | L | D | H | W | 1.17 |
| 4H   | C | X | R | G | G | S | L | X | V | W | 1.03 |
| 1J   | C | A | R | G | G | X | I | D | V | W | 1.09 |
| IF-5 | C | A | R | G | G | S | L | D | Y | W | 0.48 |

Note:
Clones ICAT 7-1 and IF-5 above show CDR3 regions having the parent sequence.

It is apparent from the data presented above that changes can be made in the amino acid sequence of the parent antibody while still retaining binding to the target. While differences in the off-rate of the antibodies presented above are within an order of magnitude, by targeting different regions of the antibody V$_H$ or V$_L$ for mutation, or finding different antibodies obtained by immunization which have $V_L$ and/or $V_H$ domains derived from the same germlne $V_L$ and $V_H$ genes as 9A4 or 5109, one may discover antibodies with variable or enhanced binding properties relative to the parental antibodies disclosed in Examples 6 and 7 cited above.

Example 9

Description of a Sandwich Assay Optimized for Urine Samples

When testing patient biological fluids for the presence of TIINE fragments, it is preferred to use urine as the test biological media. Urine is extremely easy to collect, and the collection is done in a non-invasive manner. In addition, the epitope should be at a higher concentration in the urine than in the blood. Most importantly, urine is less likely than blood to contain proteins that inhibit the assay. Thus, it is important to develop a test protocol that optimizes the measurement of TIINE fragments in urine.

In a presently preferred protocol, mAb 5109 is used as the capture antibody, and mAb 9A4 as the detection antibody. It is preferred to use each mAb in these roles, insofar as 9A4 is able to bind weakly to fragments derived from types I and III collagen in addition to the desired type II collagen fragments. Since types I and III are present in the human body in significant excess to type II collagen, fragments of types I and III are present in great excess in the urine as compared to type II fragments (approximately 1,000-fold excess, see Kivirikko, *Int. Rev. Connect. Tissue Res.*, 5:93–163 (1970)). Thus, even though 9A4 binds more strongly to type II, it still binds significantly to types I and III in urine, largely due to the presence of excess amounts of these other collagen fragments.

It has also been discovered that unknown components of urine can interfere with the assay results, yielding inaccurate readings. In an effort to reduce this effect, it has been determined that the control samples making up the standard curve are preferably made from a serially diluted stock solution of concentrated TIINE fragments (preferably peptide 131, SEQ ID NO:67) diluted in pooled control urine. Pooled control urine is a mix of urine specimens from multiple subjects, in which each samples has been previously determined to contain extremely low, preferably immeasurably low, levels of TIINE fragments. By diluting the control TIINE peptide in pooled control urine, the effects caused by proteins or other components of the urine will be recreated in the control curve, and yield a more accurate curve for the test samples.

In an additional step to reduce the spurious effects caused by urine, magnetic beads are used immediately prior to analysis on the Origen™ analyzer to remove non-specifically binding materials during the assay. After the control and test samples have been incubated with the antibodies (including the biotinylated capture antibody), magnetic streptavidin beads are added, and a magnet is used to hold the beads inside the test tube while the fluid is removed. The beads are then resuspended in a buffer solution before measurement of the signal generated by the detection antibody.

For optimal antibody binding to the TIINE fragments, it is preferred that the assay buffer maintains a pH of about 7.5. Published protocols for use of the Ordgen™ system use assay buffer with 10 mM Tris pH 7.5. After attempts to analyze urine specimens were found to be less than optimal, it was determined that 10 mM was an insufficient concentration of Tris to maintain the pH at about 7.5. Testing determined that the optimal concentration of Tris is between about 50 to about 250 mM, while a concentration of about 100 mM is presently most preferred. In the presently preferred embodiment, the assay buffer is TTBN-100, which consists of 100 mM Tris pH 7.4, 1% Tween-20, 1% BSA, and 140 mM NaCl. Any buffer that maintains the samples at an appropriate pH and doesn't otherwise interfere with the results may be substituted.

It is important to have the proper concentration of antibodies in order to yield an accurate measurement of the amount of TIINE fragments present in a sample. A preferred concentration of 9A4 is between about 10 to about 30 $\mu$g/ml, with a concentration of about 20 $\mu$g/ml being presently most preferred. A preferred concentration of 5109 is between about 5 to about 20 $\mu$g/ml, with a concentration of about 10 $\mu$g/ml being presently most preferred. Finally, the standard curve for the TIINE assay is linear in a defined range. Typically, this range will be between about 1.3 ng/ml (i.e., about 20 fmol per reaction) to about 42.5 ng/ml (i.e., about 625 fmol per reaction). As such, control samples containing known amounts of TIINE are preferably prepared with concentrations ranging from about 1.3 to about 42.5 ng/ml TIINE fragments. Unknown test samples are preferably tested in duplicate, at full concentration, and if needed, diluted in pooled control urine at various levels, so that it is likely that at least one concentration of each test sample will fall within the linear portion of the control curve.

In a preferred assay, the capture antibody is biotinylated and bound to a magnetic streptavidin bead after incubation with the sample. The Origen™ system from IGEN is a presently preferred method of measuring signal from the detection antibody. When this methodology was first used, the washed magnetic beads were being resuspended in the Origen™ assay buffer. It has surprisingly been discovered that resuspension of the beads in this buffer can lead to instability of the antibody sandwich complex, and drift in the assay results. This concern may be overcome by either rapid testing of the samples (which is often impractical), or by use of a different resuspension buffer that promotes stability of the antibody sandwich complex. Any buffer that promotes stability and provides accurate measurement of the detection antibody signal may be used for resuspending the magnetic beads. It has been determined that both TTBN-100 and DPBS serve this purpose well, with DPBS being the presently most preferred resuspension buffer.

The Origen™ electrochemiluminescence technology utilizes an extremely stable ruthenium metal chelate that participates in a luminescent reaction in the presence of tripropylamine (TPA) upon the application of an electric potential. Paramagnetic beads act as the solid phase and facilitate rapid assay kinetics. The bead/complex is transferred through a flow cell and captured magnetically on an electrode. Voltage is then applied and the level of luminescence measured. The Origen™ system allows one to form the antigen-antibody complexes in a liquid phase. This method allows for more rapid binding kinetics, and therefore shorter incubation times. The wash steps characteristic of solid-phase ELISA assays are significantly reduced by this method.

A surprising development of the use of the Origen™ system and the various methodology improvements developed therewith (and described and claimed herein) is an improvement in the detection of all forms of type II collagen peptides. There exists a natural variation in type II collagen peptides at position 774. Within a given individual, some of their type II collagen contains a proline at position 774, while the remainder of their type II collagen contains a hydroxyproline residue at this position due to post translational modification. The prior ELISA based assay methods did not detect these different peptides with equal efficiency. However, the assay as described in the present Example works equally effectively on either peptide. This same equivalence in detection can be also obtained by using proximity assays in which labeled 9A4 is utilized as the detection antibody.

The presently preferred assay is as follows. Each control or test sample was analyzed directly or diluted in control urine to yield the desired final concentration of analyte. 50 µl of each test or control sample was combined with 25 µl of Antibody Mixture, and incubated at RT for 1 hour. The Antibody Mixture consists of ruthenylated 9A4 at 20 µg/ml and biotinylated 5109 at 10 µg/ml in TTBN-100. 25 µl of magnetic streptavidin beads at 600 µg/ml in TTBN-100 were added, and incubation continued for 20 min. A magnet was used to hold the beads against the side of the container, and a pipette used to withdraw essentially all of the fluid. The beads were resuspended in 300 µl of DPBS, and results were determined using the OrigenM system from IGEN according to the manufacturers directions.

Although this method provides reliable, highly reproducible measurements, it is anticipated that that any sandwich immunoassay technique, not requiring extensive washing steps, could be developed to yield similar results using this pair of binding and detection antibodies (5109 and 9A4). Washing steps need to be minimized because the 9A4 monoclonal antibody is a low affinity binder ($1.7 \times 10^{-7}$ M). To increase throughput and automate the assay, the assay is presently being modified for use with the Advantage System (Nichols, San Juan Capistrano, Calif.). In this embodiment of the assay, the 5109 antibody is still biotinylated, however the detection antibody, 9A4, is labeled with acridinium ester. The specimens will be incubated simultaneously with both antibodies. After an initial incubation period streptavidin-coated magnetic particles will be added to the reaction mixture followed by a second incubation. The acridinium ester will be triggered to emit light by the addition of hydrogen peroxide and an alkaline solution. This treatment causes the oxidization of the product; the subsequent return to ground state results in the emission of light which is quantitated in 2 seconds and expressed in relative light units (RLU) by the system luminometer. The amount of bound label is directly proportional to the concentration of the type II collagen. Likewise, a TIINE assay could be developed using scintillation proximity in which the 5109 mAb was bound to SPA beads and the 9A4 mAb was labeled with [$^{125}$I] with the bound TIINE determined by counting in a B scintillation counter. A TIINE assay could also be envisioned using any number of radioactive or enzymatic calorimetric endpoints.

Example 10

Measurement of TIINE Fragments in Osteoarthritis Patients

Using an assay similar to that described in example 9, the urinary levels of TIINE fragments were measured in both osteoarthritis patients and control patients (Table 13). It was shown that elevated levels of TIINE fragments were found in the osteoarthritis patients, as compared to the controls. Intrapatient variability of TIINE levels over time in individuals with stable disease obtained from spot urine specimens was approximately 25%. Elevated TIINE levels among the osteoarthritis patients was associated with more severe disease as indicated by radiographic evidence of joint space narrowing and Kellgren scoring (Table 14).

TABLE 13

Comparison of TIINE levels in normal and OA subjects
Distribution of Type II Collagen (TIINE)

|  | Controls (under 40) | Controls (Age-matched) | OA |
|---|---|---|---|
| N | 20 | 33 | 126 |
| Range | 256–916 | 250–4845 | 773–9700 |
| Mean | 449 | 1066 | 2006 |
| Median | 336 | 900 | 1609 |
| P value | ←0.048→|←<0.0001→ | | |
| | ←<0.0001→ | | |

TABLE 14

Comparison between TIINE values and indices of OA
Correlation With Baseline X-rays

|  | First Sample (N = 47) | Second Sample (N = 33) |
|---|---|---|
| Likert Score | R = 0.40 (p = 0.006) | R = 0.30 (p = 0.087) |
| Knee Misalignment | R = 0.25 (p = 0.090) | R = 0.24 (p = 0.176) |
| Kellgren Score | R = 0.30 (p = 0.0390) | R = 0.38 (p = 0.029) |

In additional studies, immunohistochemistry was performed on cartilage samples from osteoarthritis patients and control patients using the 9A4 antibody. It was shown that the cartilage from osteoarthritis patients was stained by 9A4, while cartilage from control patients was not. This indicates that there is no significant amount of exposed neoepitope in the healthy cartilage, while the diseased cartilage does contain a significant amount of exposed neoepitope. This is hypothesized to be the result of collagenase degradation in the osteoarthritis patients.

Figure 4:
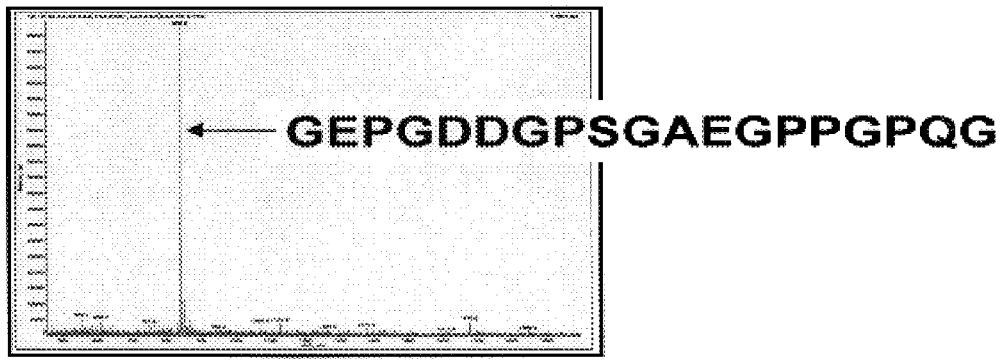
FIG. 4 is a mass spectrograph showing that the assay method was actually capturing TUNE fragments.

As in all protein detection assays, one must ascertain that the species being detected is truly the protein of interest. Specificity of urinary TIINE fragments present in samples used in this Example were confirmed by purifying protein from the samples through a 5109 affinity column followed by mass spectrometry analysis of the fractions (FIG. 4).

Example 11

Measurement of TIINE Fragments in Rheumatoid Arthritis Patients

Figure 5:
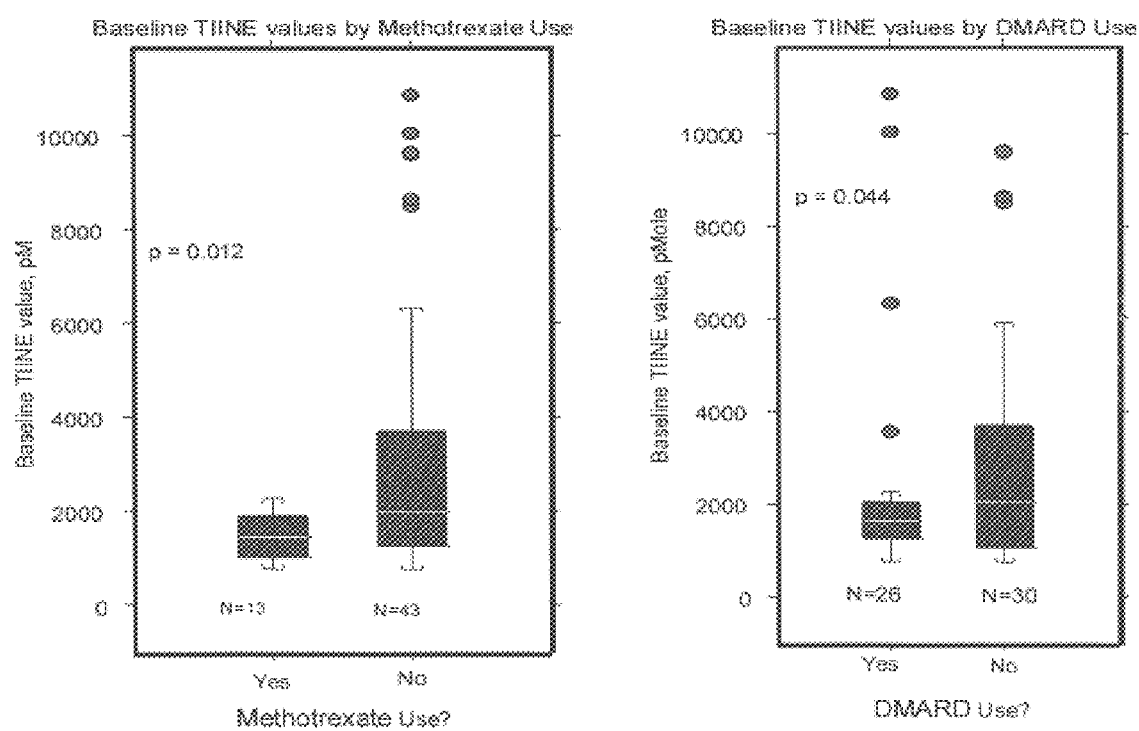
FIG. 5 is a pair of graphs comparing the TIINE levels measured by the invention methods in patients undergoing treatment with methotrexate, corticosteroids, or NSAIDs only.

The monoclonal antibodies 9A4 and 5109 were utilized in an electrochemiluminescence assay to allow the specific detection of the MMP-1, -8, and -13 type II collagen cleavage neoepitope. The levels of urinary TIINE were monitored in studies of patients with rheumatoid arthritis and control individuals. Sequential specimens were analyzed from over 150 individuals with moderate RA, with baseline, 6-month, and 2-year X-ray results available on many of the subjects. Results from retrospective analysis of urine samples from patients treated with methotrexate or corticosteroids were compared to those undergoing standard NSAID treatment alone (FIG. 5).

Figure 6:
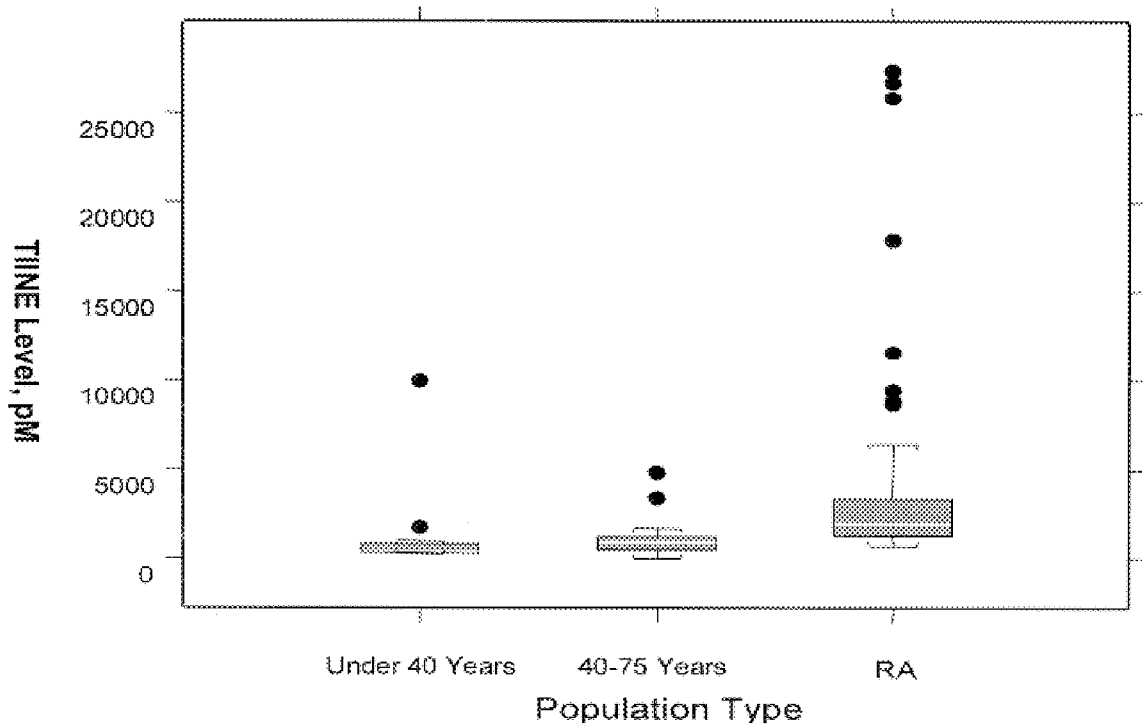
FIG. 6 is a graph demonstrating the TIINE levels measured by the invention methods in control populations and in populations suffering from rheumatoid arthritis.

Median TIINE levels in rheumatoid arthritis patients are almost twice as high as observed for the control population, with variability in spot urinary TIINE levels of approximately 25% (FIG. 6). Median TIINE levels observed from individuals undergoing methotrexate treatment were 30% percent lower than NSAID users. TIINE values correlated with several measures of rheumatoid arthritis disease status including swollen and painful joint count and Physician's Global Assessment. Furthermore, when TIINE levels were compared to X-ray scores, this marker was observed to correlate with, and predict, worsening disease status (Table 15). These results indicate that this marker is associated with disease pathogenesis, stage, and is reasonably expected to be predictive of disease outcome.

TABLE 15

TIINE LEVELS CORRELATE WITH DISEASE SEVERITY
MEASURES IN SHORT AND TERM RA STUDIES

Three Week Study

| | Spearman Correlations | |
|---|---|---|
| variable | BASELINE | 3 WEEKS |
| CRP | 0.45 (p = 0.0005) | 0.42 (p = 0.0016) |
| Painful Joints | 0.17 (p = 0.2053) | 0.27 (p = 0.0469) |
| Swollen Joints | 0.21 (p = 0.1141) | 0.42 (p = 0.0014) |
| Physician Global | 0.30 (p = 0.0264) | 0.25 (p = 0.0753) |

Methotrexate inverse correlation with TIINE level (p = 0.012)

Two Year Study

| Baseline | 6 month TIINE | 2 year TIINE |
|---|---|---|
| Erosions | 1 year X-ray value | Change to 2 year X-ray value |
| Joint Space Narrowing | Change to 1 year X-ray value | |

*p values < 0.05

High Collagen Scores are Predictive of High X-ray Scores and Positive Changes (Worsening) in X-ray Scores.

What is claimed is:

1. A method for monitoring urine for type II collagen fragments, said method comprising:
   a) contacting said urine with a capture antibody, wherein said capture antibody binds specifically to type II collagen fragments, to the substantial exclusion of any binding to type I or III collagen fragments;
   b) contacting said urine with a detection antibody, wherein said detection antibody binds specifically to collagenase-generated collagen fragments, wherein said fragments comprise the sequences set forth in SEQ ID NO:1 or SEQ ID NO:2; and
   c) detecting the amount of type II collagen fragments bound to said capture and detection antibodies.

2. A method according to claim 1 wherein said capture and detection antibodies are monoclonal antibodies.

3. A method according to claim 1 wherein said detection antibody has a $V_H$ sequence at least 95% homologous to that set forth in SEQ ID NO: 32, and a $V_L$ sequence at least 95% homologous to that set forth in SEQ ID NO: 33.

4. A method according to claim 1 wherein said detection antibody has the same CDRs as the $V_H$ sequence set forth in SEQ ID NO: 32, and the same CDRs as the $V_L$ sequence set forth in SEQ ID NO: 33.

5. A method according to claim 1 wherein said capture antibody binds to the sequences set forth in SEQ ID NOS: 3 and 4.

6. A method according to claim 5 wherein said capture antibody has a $V_H$ sequence at least 95% homologous to that set forth in SEQ ID NO: 48, and a $V_L$ sequence at least 95% homologous to that set forth in SEQ ID NO: 49.

7. A method according to claim 5 wherein said capture antibody has the same CDRs as the $V_H$ sequence set forth in SEQ ID NO: 48, and the same CDRs as the $V_L$ sequence set forth in SEQ ID NO: 49.

8. A method according to claim 1 wherein said contacting steps a) and b) occur simultaneously.

9. A method according to claim 8 wherein after said contacting steps, and prior to said detecting step, said capture antibody is immobilized onto a magnetic material.

10. A method according to claim 9 wherein said capture antibody is biotinylated, and said magnetic material is a magnetic streptavidin bead.

11. A method according to claim 9 wherein prior to said detecting step a majority of unbound materials are separated from said immobilized capture antibody.

12. A method according to claim 11 wherein said immobilized capture antibodies are resuspended in a buffered solution prior to said detecting step c).

13. A method according to claim 1 wherein said contacting steps a) and b) occur sequentially.

14. A method according to claim 13 wherein after said contacting step a), and prior to said contacting step b), said capture antibody is immobilized onto a magnetic material.

15. A method according to claim 14 wherein said capture antibody is biotinylated, and said magnetic material is a magnetic streptavidin bead.

16. A method according to claim 14 wherein prior to said contacting step b) a majority of unbound materials are separated from said immobilized capture antibody.

17. A method according to claim 16 wherein said immobilized capture antibodies are resuspended in a buffered solution prior to said detecting step c).

18. A method according to claim 1 wherein said capture antibody is present in said contacting step a) at a concentration of between about 5 to about 20 µg/ml.

19. A method according to claim 18 wherein said capture antibody is present in said contacting step a) at a concentration of about 10 µg/ml.

20. A method according to claim 1 wherein said detection antibody is present in said contacting step b) at a concentration of between about 10 to about 30 µg/ml.

21. A method according to claim 20 wherein said detection antibody is present in said contacting step b) at a concentration of about 20 µg/ml.

22. A method according to claim 1 wherein said detecting step is performed by detecting the result of an enzymatic reaction, an electrochemical signal, an optical signal, a radioactive signal, a fluorescent signal or through a scintillation proximity assay (SPA).

23. A method according to claim 1 wherein said detecting step is performed by measuring electrochemiluminescence, luminescence or light emitted and read by a β scintillation counter.

24. A method according to claim 1 wherein said contacting steps a) and b) are performed in a buffer comprising Tris pH 7.4 at a concentration of between 50 and 250 mM, Tween-20 at a concentration of between 0.5 and 2.0%, BSA at a concentration of between 0.5 and 2.0%, and NaCl at a concentration of between 100 and 200 mM.

25. A method according to claim 1 comprising the further steps of:
   d) contacting a series of control samples with said capture antibody;
   e) contacting said control samples with said detection antibody; and
   f) detecting the amount of type II collagen fragments in said control samples bound to said capture and detection antibodies.

26. A method according to claim 25 wherein said control samples comprise known amounts of type II collagen fragments diluted in control urine.

27. A method according to claim 1 comprising a further step of removing unbound detection antibody after said contacting step b) and before said detecting step c).

28. A kit for monitoring urine for type II collagen fragments, said kit comprising:

a) a capture antibody, wherein said capture antibody binds specifically to type II collagen fragments, to the substantial exclusion of any binding to type I or III collagen fragments;

b) a detection antibody, wherein said detection antibody binds specifically to collagenase-generated collagen fragments, wherein said fragments comprise the sequences set forth in SEQ ID NO:1 or SEQ ID NO:2;

c) a container; and d) instructions describing a method of using said first antibody and said second antibody to monitor biological media for type II collagen fragments.

29. A kit according to claim 28, wherein said detection antibody has a $V_H$ sequence at least 95% homologous to that set forth in SEQ ID NO: 32, and a $V_L$ sequence at least 95% homologous to that set forth in SEQ ID NO: 33, and said capture antibody has a $V_H$ sequence at least 95% homologous to that set forth in SEQ ID NO: 48, and a $V_L$ sequence at least 95% homologous to that set forth in SEQ ID NO: 49.

30. A kit according to claim 28, wherein said detection antibody has the same CDRs as the $V_H$ sequence set forth in SEQ ID NO: 32, and the same CDRs as the $V_L$ sequence set forth in SEQ ID NO: 33, and said capture antibody has the same CDRs as the $V_H$ sequence set forth in SEQ ID NO: 48, and the same CDRs as the $V_L$ sequence set forth in SEQ ID NO: 49.

31. A kit according to claim 28, said kit further comprising:

e) a positive control fluid comprising control urine containing a known amount of type II collagen fragments; and f) a dilution fluid comprising control urine for diluting samples being tested with said kit.

32. A method of diagnosing a patient for a disease state associated with the degradation of type II collagen, said method comprising the step of detecting the presence of atypically large amounts of type II collagen fragments in urine collected from said patient, wherein said fragments are detected using a detection antibody active against the sequences set forth in SEQ ID NOS: 1 and 2.

33. A method according to claim 32, wherein said disease state is osteoarthritis or rheumatoid arthritis.

34. A method of performing a clinical trial to evaluate a drug believed to be useful in treating a disease state associated with the degradation of type II collagen, said method comprising:

a) measuring the level of type II collagen fragments in urine collected from a set of patients;

b) administering said drug to a first subset of said patients, and a placebo to a second subset of said patients;

c) repeating step a) after the administration of said drug or said placebo; and d) determining if said drug is reducing the amount of type II collagen fragments present in said urine of said first subset of patients to a degree that is statistically significant as compared to any reduction occurring in said second subset of patients, wherein a statistically significant reduction indicates that said drug is useful in treating said disease state.

35. A method according to claim 34, wherein said disease state is osteoarthritis or rheumatoid arthritis.

* * * * *